US011456073B2

(12) United States Patent
Davis et al.

(10) Patent No.: US 11,456,073 B2
(45) Date of Patent: Sep. 27, 2022

(54) SYSTEMS AND METHODS FOR CGM-BASED BOLUS CALCULATOR FOR DISPLAY AND FOR PROVISION TO MEDICAMENT DELIVERY DEVICES

(71) Applicant: DexCom, Inc., San Diego, CA (US)

(72) Inventors: Anna Leigh Davis, Cardiff, CA (US); Scott M. Belliveau, San Diego, CA (US); Esteban Cabrera, Jr., San Diego, CA (US); Alexandra Elena Constantin, San Diego, CA (US); Rian Draeger, San Francisco, CA (US); Peter Galuardi, San Diego, CA (US); Hari Hampapuram, San Diego, CA (US); Matthew Lawrence Johnson, Encinitas, CA (US); Apurv Ullas Kamath, San Diego, CA (US); Katherine Yerre Koehler, Solana Beach, CA (US); Aarthi Mahalingam, San Diego, CA (US); Gary A. Morris, La Jolla, CA (US); Philip Thomas Pupa, San Diego, CA (US); Peter C. Simpson, Cardiff, CA (US); Brian Christopher Smith, San Marcos, CA (US); Tomas C. Walker, Henderson, NV (US)

(73) Assignee: Dexcom, Inc., San Diego, CA (US)

(*) Notice: Subject to any disclaimer, the term of this patent is extended or adjusted under 35 U.S.C. 154(b) by 0 days.

(21) Appl. No.: 15/699,940

(22) Filed: Sep. 8, 2017

(65) Prior Publication Data
US 2018/0075201 A1 Mar. 15, 2018

Related U.S. Application Data

(63) Continuation of application No. 15/699,792, filed on Sep. 8, 2017.

(Continued)

(51) Int. Cl.
*G16H 40/63* (2018.01)
*G06F 21/44* (2013.01)
(Continued)

(52) U.S. Cl.
CPC .............. *G16H 40/63* (2018.01); *G06F 21/44* (2013.01); *G06F 21/602* (2013.01);
(Continued)

(58) Field of Classification Search
CPC ........ G16H 20/17; G16H 20/30; G16H 10/60; G16H 40/67; G16H 50/30; G16H 80/00;
(Continued)

(56) References Cited

U.S. PATENT DOCUMENTS 6,923,763 B1    8/2005   Kovatchev et al.
7,025,425 B2    4/2006   Kovatchev et al.
(Continued)

FOREIGN PATENT DOCUMENTS

JP      2002297771 A     10/2002
KR      20150097731 A     8/2015
(Continued)

OTHER PUBLICATIONS

A. Kawaguchi, S. Russell and Guoliang Qian, "Security issues in the development of a wireless blood-glucose monitoring system," 16th IEEE Symposium Computer-Based Medical Systems, 2003. Proceedings., 2003, pp. 102-107, doi: 10.1109/CBMS.2003. 1212774. (Year: 2003).*

(Continued)

*Primary Examiner* — Evangeline Barr
(74) *Attorney, Agent, or Firm* — Patterson + Sheridan, LLP

(57)  ABSTRACT

Disclosed are systems and methods for secure and seamless set up and modification of bolus calculator parameters for a bolus calculator tool by a health care provider (HCP). In one (Continued)

aspect, a method for enabling HCP set up of a bolus calculator includes providing a server accessible by both an HCP and a patient; upon login by the HCP, displaying, or transmitting for display, a fillable form, the fillable form including one or more fields for entry of one or more bolus calculator parameters; receiving data from the fillable form, the data corresponding to one or more bolus calculator parameters; and upon login by the patient, transmitting data to a device associated with the patient, the transmitted data based on the received data, where the transmitted data corresponds to one or more of the bolus calculator parameters in a format suitable for entry to a bolus calculator.

25 Claims, 35 Drawing Sheets

Related U.S. Application Data

(60) Provisional application No. 62/385,808, filed on Sep. 9, 2016.

(51) Int. Cl.
| | |
|---|---|
| *G16H 80/00* | (2018.01) |
| *G16H 40/67* | (2018.01) |
| *G16H 50/30* | (2018.01) |
| *G06F 21/62* | (2013.01) |
| *A61M 5/142* | (2006.01) |
| *G16H 20/60* | (2018.01) |
| *A61M 5/172* | (2006.01) |
| *G16H 20/17* | (2018.01) |
| *G16H 10/60* | (2018.01) |
| *G16H 10/20* | (2018.01) |
| *G06F 21/60* | (2013.01) |
| *G16H 20/30* | (2018.01) |
| *G16H 20/70* | (2018.01) |

(52) U.S. Cl.
CPC ......... *G06F 21/6245* (2013.01); *G16H 10/20* (2018.01); *G16H 10/60* (2018.01); *G16H 20/17* (2018.01); *G16H 40/67* (2018.01); *G16H 50/30* (2018.01); *G16H 80/00* (2018.01); *A61M 5/14248* (2013.01); *A61M 5/1723* (2013.01); *A61M 2005/14208* (2013.01); *A61M 2205/3553* (2013.01); *A61M 2205/50* (2013.01); *A61M 2230/201* (2013.01); *G16H 20/30* (2018.01); *G16H 20/60* (2018.01); *G16H 20/70* (2018.01)

(58) Field of Classification Search
CPC .. G06F 21/44; G06F 21/6245; A61M 5/1723; A61M 2230/201; A61M 2005/14208; A61M 2205/3553
See application file for complete search history.

(56) References Cited

U.S. PATENT DOCUMENTS

| | | | |
|---|---|---|---|
| 7,374,935 B2 | 5/2008 | Pellicer et al. | |
| 7,591,801 B2 | 9/2009 | Brauker et al. | |
| 7,874,985 B2 | 1/2011 | Kovatchev et al. | |
| 8,226,556 B2 | 7/2012 | Hayes et al. | |
| 8,538,703 B2 | 9/2013 | Kovatchev et al. | |
| 8,562,587 B2 | 10/2013 | Kovatchev et al. | |
| 8,585,593 B2 | 11/2013 | Kovatchev et al. | |
| 8,808,228 B2 | 8/2014 | Brister et al. | |
| 8,922,352 B2 | 12/2014 | Tsui et al. | |
| 9,398,869 B2 | 7/2016 | Kovatchev et al. | |
| 9,430,022 B2 | 8/2016 | Kovatchev et al. | |
| 9,452,258 B2 | 9/2016 | Dobbles et al. | |
| 9,463,277 B2 | 10/2016 | Dobbles et al. | |
| 9,750,438 B2 | 9/2017 | Kovatchev et al. | |
| 10,369,281 B2 | 8/2019 | Yodfat et al. | |
| 2008/0154513 A1 | 6/2008 | Kovatchev et al. | |
| 2008/0220403 A1 | 9/2008 | Marling et al. | |
| 2008/0312512 A1 | 12/2008 | Brukalo et al. | |
| 2009/0171589 A1 | 7/2009 | Koovatchev et al. | |
| 2010/0179768 A1 | 7/2010 | Kovatchev et al. | |
| 2010/0198520 A1 | 8/2010 | Breton et al. | |
| 2010/0249561 A1 | 9/2010 | Patek et al. | |
| 2010/0268304 A1* | 10/2010 | Matos | G16H 40/63 607/60 |
| 2010/0292556 A1* | 11/2010 | Golden | G16H 40/67 600/364 |
| 2012/0004512 A1 | 1/2012 | Kovatchev et al. | |
| 2012/0078067 A1 | 3/2012 | Kovatchev et al. | |
| 2012/0232520 A1 | 9/2012 | Sloan et al. | |
| 2012/0245556 A1 | 9/2012 | Kovatchev et al. | |
| 2013/0116649 A1 | 5/2013 | Breton et al. | |
| 2013/0268764 A1* | 10/2013 | Valdes | G06F 21/64 713/178 |
| 2013/0317753 A1 | 11/2013 | Kamen et al. | |
| 2013/0345663 A1 | 12/2013 | Agrawal et al. | |
| 2014/0012117 A1 | 1/2014 | Mensinger et al. | |
| 2014/0149329 A1 | 5/2014 | Shaw | |
| 2014/0180203 A1 | 6/2014 | Budiman et al. | |
| 2014/0181959 A1* | 6/2014 | Li | G06F 21/32 726/19 |
| 2014/0200426 A1 | 7/2014 | Taub et al. | |
| 2014/0288494 A1 | 9/2014 | Brister et al. | |
| 2014/0310296 A1* | 10/2014 | Stivoric | G06Q 30/0242 707/758 |
| 2014/0324445 A1 | 10/2014 | Carlsgaard et al. | |
| 2014/0325065 A1* | 10/2014 | Birtwhistle | H04L 47/70 709/225 |
| 2015/0018633 A1 | 1/2015 | Kovatchev et al. | |
| 2015/0141912 A1 | 5/2015 | Estes | |
| 2015/0151050 A1* | 6/2015 | Estes | A61M 5/172 604/500 |
| 2015/0190098 A1 | 7/2015 | Patek et al. | |
| 2015/0205947 A1* | 7/2015 | Berman | A61B 5/14532 726/16 |
| 2015/0238694 A1 | 8/2015 | Steil et al. | |
| 2016/0004813 A1 | 1/2016 | Kovatchev et al. | |
| 2016/0038675 A1* | 2/2016 | Estes | G06F 19/00 604/506 |
| 2016/0063191 A1 | 3/2016 | Vesto et al. | |
| 2016/0117481 A1 | 4/2016 | Booth et al. | |
| 2016/0132660 A1 | 5/2016 | Barajas et al. | |
| 2016/0171183 A1 | 6/2016 | Breton et al. | |
| 2016/0232322 A1* | 8/2016 | Mensinger | A61B 5/7275 |
| 2016/0331310 A1 | 11/2016 | Kovatchev et al. | |
| 2017/0053100 A1 | 2/2017 | Neftel | |
| 2017/0053552 A1 | 2/2017 | Zhong et al. | |
| 2017/0056591 A1 | 3/2017 | Breton et al. | |
| 2017/0098037 A1 | 4/2017 | Agassi et al. | |
| 2018/0075200 A1 | 3/2018 | Davis et al. | |
| 2018/0075202 A1 | 3/2018 | Davis et al. | |
| 2019/0099551 A1 | 4/2019 | Yodfat et al. | |
| 2019/0252071 A1 | 8/2019 | Davis et al. | |

FOREIGN PATENT DOCUMENTS

| | | | |
|---|---|---|---|
| WO | WO 2005-082436 | 9/2005 | |
| WO | WO-2006079124 A2 * | 7/2006 | ......... G06F 19/3481 |
| WO | WO 2008-101172 | 8/2008 | |
| WO | WO 2009-048462 | 4/2009 | |
| WO | 2010019919 A1 | 2/2010 | |
| WO | WO 2010-111660 | 9/2010 | |
| WO | WO-2015191562 A1 | 12/2015 | |
| WO | WO-2016001922 A1 | 1/2016 | |
| WO | WO 2016-025874 | 2/2016 | |
| WO | WO 2016-040927 | 3/2016 | |
| WO | 2016069475 A1 | 5/2016 | |
| WO | WO 2016-133879 | 8/2016 | |

(56) References Cited

FOREIGN PATENT DOCUMENTS

| WO | WO 2016-201120 | 12/2016 |
|----|----------------|---------|
| WO | WO 2017-132663 | 8/2017  |

OTHER PUBLICATIONS

Pesl et al. 2016. IEEE J Biomed HealthInformatics 20(1):11-17. An Advanced: Bolus Calculator for Type 1 Diabetes: System Architecture and Usability Results (doi: 10.1109/JBHL.2015/2464088).

Pesl et al. 2014, A Mobile-Based Advanced Bolus Calculator for Diabetes Management (poster). 8$^{th}$ Intl Conf on Advanced Technologies and Treatments for Diabetes, Paris, France, Feb. 18-21, 2014.

Pesl et al. 2015. Acceptability of a Patient and Clinical Platform of an Advanced Bolus Calculator for Type 1 Diabetes (ABC4D) (poster and abstract). Diabetes Technology U Therapeutics 17:A129 (Abstract 292).

Scheiner 2015. Practical CGM: A Guide to Improving Outcomes through Continuous Glucose Monitoring. Chapter 2, pp. 17-34, American Diabetes Association, Inc., Alexandria, VA.

Walsh et al. 2014. J. Diabetes Science & Technology 8(1):170-178. Confusion regarding duration of insulin action: a potential source for major insulin does errors by bolus calculators.

Office Action for Canadian Application No. 3,029,272 dated Aug. 28, 2020, 5 pages.

International Preliminary Report on Patentability for Application No. PCT/US2017/050688 dated Mar. 21, 2019, 8 pages.

International Search Report and Written opinion for Application No. PCT/US2017/050688 dated Nov. 17, 2017, 8 pages.

Partial Supplementary European Search Report for Application No. 17849614.7 dated Feb. 27, 2020, 13 pages.

Extended European Search Report for Application No. 117849614.7 dated Jun. 26, 2020, 11 pages.

Office Action for Canadian Application No. 3,029,272 dated Jun. 11, 2021, 3 pages.

Office Action for Canadian Application No. 3,075,124, dated May 25, 2021, 3 pages.

\* cited by examiner

SYSTEMS AND METHODS FOR CGM-BASED BOLUS CALCULATOR FOR DISPLAY AND FOR PROVISION TO MEDICAMENT DELIVERY DEVICES

CROSS REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/699,792, filed on Sep. 8, 2017, which claims the benefit of U.S. Provisional Application No. 62/385,808, filed Sep. 9, 2016. Each of the aforementioned applications is incorporated by reference herein in its entirety, and each is hereby expressly made a part of this specification.

TECHNICAL FIELD

The present disclosure relates generally to continuous monitoring of analyte values received from an analyte sensor system. More particularly, the present disclosure is directed to systems, methods, apparatuses, and devices, for health care provider involvement in the set up and optimization of medicament calculators and delivery devices.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is not only unlikely that a diabetic will take a timely SMBG value, but will not know if his blood glucose value is going up (higher) or down (lower), due to limitations of conventional methods.

Consequently, a variety of non-invasive, transdermal (e.g., transcutaneous) and/or implantable electrochemical sensors are being developed for continuously detecting and/or quantifying blood glucose values. Continuous glucose monitors have been increasing in popularity as an easy way to monitor glucose levels. In the past, patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

One potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and software applications (apps) executing on smart phones, some users prefer to avoid having to carry a dedicated display. Instead, some users prefer to monitor their glucose levels using a dedicated software app executing on their mobile computing device, such as a smart phone, tablet or wearable device like a smart watch or smart glasses.

SUMMARY

Systems and methods according to present principles include ways in which users and healthcare professional(s) (HCPs) may securely communicate, usually over a wireless network, and particularly where the HCP is prescribing insulin to the patient, i.e., as part of a bolus calculator parameter set up or as part of a pump setup. For example, the systems and methods may provide for bolus calculator set up where secure communications are arranged between an HCP and a user, and using secure transmissions via a network that result in the desired functionality, e.g., setting up the bolus calculator. The systems and methods generally take advantage of the ubiquitous smart phone usage by users, and the systems and methods may take advantage of data determined by various sensors, including continuous glucose monitoring. The systems and methods generally provide analysis and calculation for display as part of a bolus calculator, and/or for provision of calculated data to a medicament delivery device to allow dosing by a user. Such medicament delivery devices may include, e.g., pumps, pens, and so on. In many implementations, the results of bolus calculator calculations may at least partially control a medical device such as a medicament delivery device, such as a pump or pen.

The ways provided may be unique to the situation encountered by different HCPs, e.g., may take account of the amount of time they may have available to spend with the patient, which may be either short or long. The different HCPs may include, e.g., endocrinologists, family practice doctors, certified diabetes educators, nurses, followers, and even other users. As the ways differ, the same may be provided with different amounts of information about the patient, e.g., followers may just get a glucose value, while endocrinologists may get analyzed pattern graphs, and so on.

In addition, by automatically providing different amounts of information, data, to different types of providers, the machine providing such data run significantly more efficiently, and this factor can also have significant effects on battery life, wear and tear, and so on. Moreover, the display of such data may be automatically configured to fit on the display screen size available, altering the user interface in an automatic manner to accommodate the differing amounts and types of data to be displayed.

The systems and methods relate not only to initial set up, but can also be used to update parameters and to send updated parameters to a user, either for direct and automatic modification of bolus calculator parameters or to allow the user to modify the parameters manually. In another implementation, the modifications can be downloaded and proposed to be automatically applied to the bolus calculator, but require confirmation by the user prior to actual modification of the parameters.

Systems and methods according to present principles do not generally only review past data in a retrospective fashion to determine the success or failure of a user's treatment of their diabetes. Using systems and methods described, a "give and take" can be enabled between the user, who is generating the data, and the doctor, who is reviewing the data and analyzing the same in concert with the patient. In the same way, the doctor can provide more significant and meaningful, as well as more frequent, updates to bolus calculator parameters as may be needed, to "hone in" on a best set of parameters or to determine the best set of parameters for a given situation of the patient, e.g., weekends versus weekdays. In this way, systems and methods according to present principles solve the technical problem of user devices having sub optimal bolus calculator parameters, and in solves these problems in a technical way, by allowing the back-and-forth communications which were previously unheard of in this context.

In some cases, insurance can allow an HCP to be reimbursed for the initial meeting and set up of the bolus calculator, even if the setup is done remotely. In the same way, transmission of an updated set of parameters, along with an optional HCP patient consultation, can give rise to another billing event. Updates of parameters can emanate not only from automatic algorithms, which are expected to be the most common source of such updates, but also from users. For example, if a user is habitually dosing one unit more than the bolus calculator suggests, and the user is getting satisfactory results, the bolus calculator parameters may be updated to automatically increase the dosing. In some cases, a notification of a suggested update may be sent to the HCP for confirmation and approval.

In one technique, an HCP bolus calculator setup app could be provided to an HCP, e.g., via an invitation link (sent by text, email, etc., or via techniques noted above with respect to the flowcharts described below) from the patient user to the HCP, that would provide an interface for the HCP to set up bolus calculator parameters specific to the patient user and provide them back to the patient user's device for integration in the patient's bolus calculator. Using systems and methods according to present principles, a CGM enabled bolus calculator may be provided. Such provides a bolus calculator that is informed by various CGM aspects, including glucose trends. An HCP may be enabled to unlock the bolus calculator feature as well as to specify calculator parameters. The bolus calculator functionality may be disabled, e.g., when the CGM is connected to a pump, such that the pump calculator may take precedence over the CGM bolus calculator. Meal entry for the bolus calculator may be made "fuzzy", so that a user may more conveniently enter a meal size as small, average, or large. Parameters for these different meal sizes may be prescribed by the HCP during setup. Third party food database apps may be employed as inputs to the bolus calculator, with the input capable of being confirmed by the user, and the user may further be afforded the ability to override such values. The CGM app may further be enabled to compute IOB for MDI users within the context of the bolus calculator.

Generally, data from third party apps may be validated and/or authenticated prior to usage in a bolus calculator app. For example, the values may be 'grayed out' and not used in calculations until such time as the user confirms their accuracy. The bolus calculator app or functionality may allow user input of meal event data, e.g., entered carbs, and/or automatically pull meal event data from third-party applications, e.g., via Apple Healthkit. In this way, for example, when the user accesses their bolus calculator, recently entered carbs may be presented to them and the user may choose to use this amount in the bolus calculation, or to use a different value, e.g., taking into account a food soon to be eaten. In some cases the CGM app will not be able to validate the accuracy of carb estimates in other meal database applications, and may inform the user of that risk upon initial use.

In a first aspect, a method is provided for enabling health care provider (HCP) set up of a bolus calculator, including: a) providing a server accessible by both an HCP and a patient; b) upon login by the HCP, displaying, or transmitting for display, a fillable form, the fillable form including one or more fields for entry of one or more bolus calculator parameters; c) receiving data from the fillable form, the data corresponding to one or more bolus calculator parameters; and d) upon login by the patient, transmitting data to a device associated with the patient, the transmitted data based on the received data, where the transmitted data corresponds to one or more of the bolus calculator parameters in a format suitable for entry to a bolus calculator.

Implementations may include one or more of the following. The transmitting data to a device associated with the patient may include transmitting the data to an app associated with a bolus calculator. The app may be a continuous glucose monitoring (CGM) app, such as one running on a smart phone or on a dedicated CGM device. The transmitting data may further include encrypting the transmitted data with a patient encryption key. The method may further include, prior to the encrypting, uploading a patient encryption key. The transmitted data may be a copy of the received data. The method may further include, on the device associated with the patient, receiving the transmitted data and automatically modifying bolus calculator parameters using the transmitted data. The method may further include, upon an unsuccessful login by the HCP, causing the display of an HCP account creation screen. The method may further include, upon an unsuccessful login by the patient, causing the display of a patient account creation screen. The method may further include, upon login by the patient, causing display of a warning screen, whereby the patient may be warned against bolus calculator set up without involvement of an HCP. The method may further include, upon login by the HCP, retrieving one or more parameters relevant to the bolus calculator set up from a medicament delivery device or a user account associated with a medicament delivery device.

A first portion of the bolus calculator parameters may be from the transmitted data, and a second portion of the bolus calculator parameters may be from the medicament delivery device or the user account associated with a medicament delivery device. The method may further include accessing a database of medicament delivery devices, and generating a textual version of the parameters according to a medicament delivery device associated with the patient. The transmitting data to the patient may include transmitting a textual version of parameters relevant to a bolus calculator set up. The patient login may be enabled at least in part by a code, the code entered by the patient, the code received by the patient from the HCP. The code may also be created by the HCP when the HCP associates a new patient with an HCP user account. The HCP login may be enabled at least in part by a code, the code entered by the HCP, the code received by the HCP from the patient. The code may be created by the patient when the patient associates an HCP with a patient user account. Upon creation of the code, a time window may be instantiated during which the HCP may be enabled to make changes to the bolus calculator settings/parameters. The method may further include receiving a confirmation message from the patient following a display of the transmitted data on a display associated with the patient, and upon receipt of the confirmation message, transmitting final data to the display associated with the patient, to a bolus calculator app, or to a CGM app incorporating bolus calculator functionality. The method may further include receiving a modification message from the patient following a display of the transmitted data on a display associated with the patient, whereby the patient is enabled to request a modification of the HCP-entered bolus calculator parameters. The method may further include transmitting a notification to the HCP of the requested modification. Upon receipt of confirmation from the HCP of the requested modification, the method may further include transmitting final data to a display associated with the patient or to a bolus calculator app.

The bolus calculator settings/parameters may include a basal rate, and may further be confined by guard rails or safe ranges. A messaging/email service may be accessed, upon the occurrence of a change in bolus, from the HCP to the patient, or from the patient to the HCP, upon the occurrence of a change in bolus. The method may further include determining or detecting a bolus calculator parameter/setting change triggering event, and in response to the determining or detecting, transmitting a notification to the HCP about the event. Multiple bolus calculator parameters/setting change triggering events may be determined or detected, and the method may further include prioritizing or ranking the triggering events before transmitting the notification to the HCP. The method may further include transmitting a subset of the prioritized or ranked events to the HCP. Where the bolus calculator parameters/setting change triggering event include a detected pattern, the pattern detected may be via an analysis of CGM traces. The pattern may be one that is remediable by a change in bolus calculator parameters/settings. The pattern may be, e.g., one of nighttime lows or post-prandial highs. The bolus calculator parameters/setting change triggering event may include an atypical glucose response. The method may further include receiving a modification to bolus calculator parameters/settings, and transmitting the modification to the device associated with the patient. The modification may adjust a basal rate or a bolus calculator parameters/setting.

The triggering event may include detection of at least occasional departures in delivered insulin boluses as compared to calculated bolus values. The departures may be are of the same sign and the value, and/or the departure values may be within a common range. The transmitting data may include transmitting using a Bluetooth communications protocol or using a near field communications protocol. The method may further include performing a bolus calculation at least in part based on the transmitted data. The method may further include receiving additional data, and also performing the bolus calculation at least in part based on the additional data. The receiving additional data may include receiving additional data from an external app or from user entry. The additional data may be received from an external app, and the method may further include authenticating or validating the app or the additional data prior to use in the bolus calculation. The additional data may be received from an external app, and the method may further include prompting a user for confirmation prior to using the additional data in the bolus calculation. The additional data may be received from user entry, and the user entry may be in a categorized or fuzzy form. The receiving additional data may include receiving additional data from a continuous glucose monitoring system. The additional data may include trend data or glucose rate of change data.

The method may further include transmitting the transmitted data, or data based on the transmitted data, to a medicament delivery device. The medicament delivery device may be a pump or a pen, or a bolus calculator app associated with the pump or pen. The bolus calculator parameters entered by the HCP may be specific to a range of time within a day. The bolus calculator parameters entered by the HCP may be specific to weekdays versus weekends. The form may be displayed to the HCP with pre-populated data. The pre-populated data may be obtained from user account data. The pre-populated data may be obtained from data associated with a medicament delivery device. The method may further include receiving edits to the pre-populated data, and creating the transmitted data based on the edited pre-populated data. The method may further include, on the device associated with the patient, receiving the transmitted data and displaying an approval prompt on a user interface of the device, and upon acceptance of the approval prompt, automatically modifying bolus calculator parameters using the transmitted data.

In a second aspect, a method is provided for continuous glucose monitoring, configured for secure communications between an HCP and a patient, including: a. receiving first data from a form on a web app, the data pertaining to bolus calculator parameters and/or settings, the data associated with a patient user account, a session of the web app associated with an HCP user account; b. performing a first transforming of the received first data into second data, the second data in a form operable to be entered into a bolus calculator app; c. performing a second transforming of the second data into secured second data, where the secured second data can only be used by a device associated with the patient user account; and d. transmitting the secured second data to the patient user account, or making accessible the secured second data from the patient user account.

Implementations may include one or more of the following. The second data may be in a form operable to be automatically transmitted into storage or memory on a device running the bolus calculator app. The device may be a smart phone or a dedicated device, and the bolus calculator app may be a standalone app or a bolus calculator functionality within a continuous glucose monitoring app. The second data may be in a form operable to be entered by a user into storage or memory on a device running the bolus calculator app. The device may be a smart phone or a dedicated device, and the bolus calculator app may be a standalone app or a bolus calculator functionality within a continuous glucose monitoring app. The second transforming may include an encryption step. The encryption step may encode the second data with a patient encryption key, the patient encryption key associated with the patient user account. The transmitting may include transmitting the secured second data to a device associated with the patient user account, and the device may be configured to use the secured second data in a bolus calculator. The method may further include causing a display of the secured second data on a device linked to the patient user account. The method may further include receiving confirmation or approval from the patient of the displayed secured second data. The method may further include receiving a request for modification from the patient of the displayed secured second data. The method may further include forwarding the request for modification to the HCP user account.

In a third aspect, a method is provided for continuous analyte monitoring, configured for interoperability with one or more third-party applications, including: a. running a continuous glucose monitoring (CGM) app on a first device, the CGM app in communications with a CGM sensor through sensor electronics, the sensor electronics coupled to the sensor and transmitting data to the first device; b. receiving data in the CGM app from another app, the data received through an API, the received data operable to provide bolus calculation to a user of their diabetic state, the received data operable to provide the bolus calculation when used in combination with data from the CGM sensor in the providing of the bolus calculation; and c. prior to using the received data, attempting to authenticate the data, and if the authentication is successful, using the received data in combination with sensor data to provide the bolus calculation, and if the authentication is not successful, then not using the received data to provide the bolus calculation.

Implementations may include one or more of the following. The first device may be a smart phone or a dedicated continuous glucose monitor. The attempting to authenticate may include comparing a timestamp on the received data to a timestamp on sensor data, or comparing a timestamp on the received data to a time of receiving the data according to a clock on the first device. The other app may be one running on a second device. The second device may be a medicament delivery device including a pump or pen. The second device may be a wearable fitness sensor. The authenticating may include determining if the app is a trusted app by comparing a certificate associated with the app to a list of trusted certificates stored on the first device. The received data may include exercise data or meal data. The received data may include population data from a database. The method may further include, prior to using the received data, displaying the received data for confirmation by a user on a user interface of the first device, and upon successful confirmation, using the received data in the bolus calculation. The continuous glucose monitoring app may include bolus calculator functionality, the other app may be running on a medicament delivery device incorporating bolus calculator functionality, and the method may further include automatically disabling the bolus calculator functionality in the continuous glucose monitoring app upon detecting that the other app incorporates bolus calculator functionality. The authentication may include determining a first identification of a user associated with the continuous glucose monitoring app, and determining a second identification of a user associated with the other app, and determining if the first and second identifications pertain to the same user.

In a fourth aspect, an application is provided that is configured to execute on a mobile device, comprising: a first input configured to receive signal data from a continuous indwelling analyte sensor and transmitter; a second input configured to receive signal data corresponding to subject patient data and/or patient population data; and instructions configured to employ the first and second inputs to calculate a bolus value, wherein the second input is employed to provide settings and/or parameters for a bolus calculator, and wherein the first input is employed to provide current patient analyte concentration values to be applied to a function at least in part determined by the settings and/or parameters to calculate the bolus value.

Implementations may include one or more of the following. The application may further comprise one or more inputs for one or more third party applications, wherein the instructions are further configured to calculate the bolus value based additionally on the inputs for the third party applications. The application may further comprise instructions for receiving the signal data from the continuous indwelling analyte sensor and for calculating and displaying a clinical value of the analyte concentration. The application may further comprise instructions for calibrating the received signal data. The instructions for calibrating the received signal data may use only the signal data itself, or may use the signal data along with other external data. The instructions may be further configured to transmit the calculated bolus value to a medicament delivery device. The instructions may be further configured to, if the mobile device is in signal data communication with a medicament delivery device having a bolus calculator, suspend the calculation of a bolus value. The instructions may be further configured to receive signal data corresponding to subject patient data and/or patient population data in a secure manner from a health care practitioner server.

In a fifth aspect, an application is provided that is configured to execute on a server, comprising: first instructions configured to receive data about a subject user and to setup a subject user account; a first input configured to receive sensor data from a device associated with a subject user; second instructions configured to analyze data from the first input and determine if bolus calculator parameters and/or settings on the subject user device are optimal; third instructions configured to, if the parameters and/or settings on the subject user device are not optimal, transmit a signal to a health care practitioner portal associated with the server, or to the subject user device, cause a modification of the parameters and/or settings.

Implementations may include one or more of the following. The third instructions may be further configured to display a prompt on the portal and to receive a modified one or more parameters and/or settings from a health care practitioner. The third instructions may be further configured to encrypt or secure the modified parameters and/or settings prior to transmission to the subject user device. The second instructions may be further configured to determine if bolus calculator parameters and/or settings on the subject user device are optimal by detecting if a bolus calculator parameter/setting change triggering event has occurred.

In further aspects and embodiments, the above method features of the various aspects are formulated in terms of a system as in various aspects, configured to carry out the method features. Any of the features of an embodiment of any of the aspects, including but not limited to any embodiments of any of the first through fifth aspects referred to above, is applicable to all other aspects and embodiments identified herein, including but not limited to any embodiments of any of the first through fifth aspects referred to above. Moreover, any of the features of an embodiment of the various aspects, including but not limited to any embodiments of any of the first through third aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through fifth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through fifth aspects referred to above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further aspects of the present disclosure will be more readily appreciated upon review of the detailed description of the various disclosed embodiments, described below, when taken in conjunction with the accompanying figures.

Figure 1A:
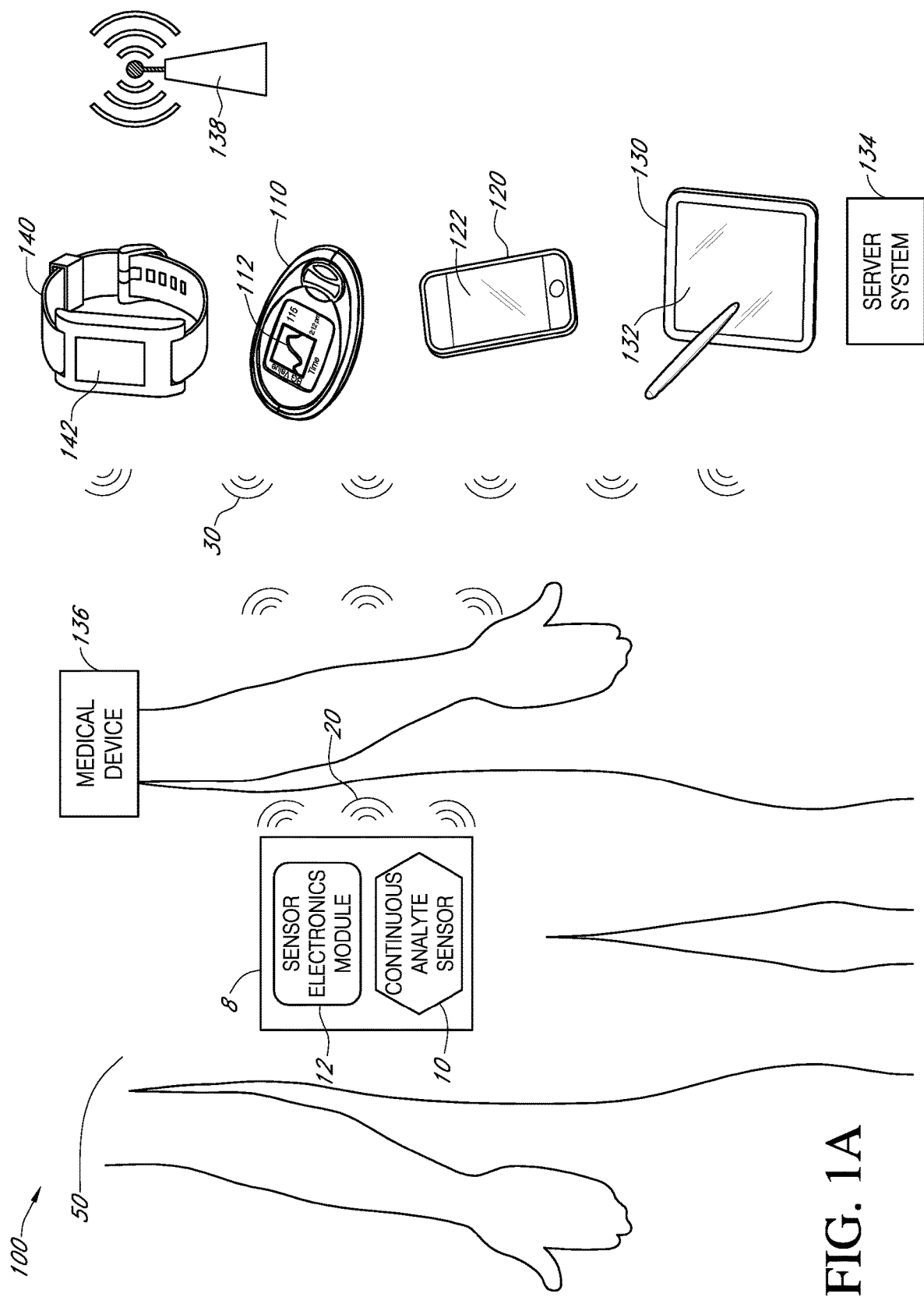
FIG. 1A illustrates aspects of an example system for that may be used in connection with implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure may be practiced with modification or alteration, and that the disclosure may be limited only by the claims and the equivalents thereof.

DETAILED DESCRIPTION

Besides continuous glucose monitors, another device used by diabetics is a bolus calculator (BC), which is a tool that helps patients determine how much insulin is needed to sufficiently manage their glucose levels, particularly around events such as meals, activity, and sleep. For example, a bolus calculator can determine a specific amount of insulin to "bolus" to cover after a meal, e.g., to correct for a potentially high glucose level. Determining one's insulin dose is an essential yet complicated task that diabetic patients should perform to accurately calculate an appropriate dose of insulin and to administer the calculated dose safely. Generally, bolus calculators involve a three-part calculation based on insulin on board (IOB), carbohydrate coverage, and correction factors. Automating the complicated arithmetic used for insulin dose calculations reduces the burden of mental math for patients, minimizes mistakes, and helps patients achieve better glucose control.

Drawbacks exist to current bolus calculators, however. For example, as opposed to users on pumps, multiple daily injection therapy (MDI) patients typically do not have access to an FDA-approved bolus calculator. In more detail, while bolus calculators are available on insulin pumps, there is a lack of available FDA-approved bolus calculators for MDI patients, who generally employ a CGM-only system configuration or a system configuration using CGM-with-insulin pen. As a result of the lack of availability, MDI users often bolus qualitatively, e.g., guessing their dose, rather than quantitatively determining their dose based on data. Moreover, many MDI users generally do not or cannot consider IOB in their dosing decisions.

Another drawback is that there are many unapproved bolus calculator apps, but virtually none have received good reviews.

Whether for pump patients or for MDI users, in order to provide a safely-used bolus calculator, assistance and input by a healthcare professional (HCP) is essential, if not required. Such HCPs include, e.g., endocrinologists, family physicians, internists, general practice physicians, nurses, certified diabetic educators, and so on. However, for certain types of HCPs, time during patient visits is limited, and HCPs may not have access to resources to effectively set up a patient user's bolus calculator on a patient device such as a smartphone. Moreover, HCPs may not feel comfortable using the patient's device due to liability or other concerns. As a consequence, many BCs are not set up properly.

While a significant amount of prior art has been developed in the context of bolus calculators, particularly among pump manufacturers, the same is generally related to calculations and dosing on the basis of SMBG measurements, not continuous glucose monitoring measurements, nor on the many important properties and information derivable there from. Moreover, pump setup is in many ways different from bolus calculator set up.

Embodiments of the present disclosure are directed to systems, methods, and devices for enabling HCP set up of medicament calculators, including for the results of such calculations to be transmitted to medicament delivery devices. In various deployments described herein, the analyte data is glucose data generated by a glucose sensor system configured to connect to display devices and the like. Implementing aspects of the present disclosure, as described in detail herein, may provide for safe and convenient set up of medicament calculators and medicament delivery devices, including bolus calculators and insulin delivery devices such as pens and pumps. In particular, such aspects of the disclosure relate to, for example, set up of bolus calculator parameters by a physician which are then transmitted to patients, e.g., their smart phones and pumps. Systems and methods according to present principles provide for convenient usage, not just for patients but also for HCPs, ensuring use by both.

Systems and methods according to present principles include ways in which users and healthcare professional(s) may securely communicate, usually over a wireless network, and particularly where the HCP is prescribing insulin to the patient, i.e., as part of a bolus calculator parameter set up or as part of a pump setup. For example, the systems and methods may provide for bolus calculator set up where secure communications are arranged between an HCP and a user, and using secure transmissions via a network that result in the desired functionality, e.g., setting up the bolus calculator. The systems and methods generally take advantage of the ubiquitous smart phone usage by users, and the systems and methods may take advantage of data determined by various sensors, including continuous glucose monitoring. The systems and methods generally provide analysis and calculation for display as part of a bolus calculator, and/or for provision of calculated data to a medicament delivery device to allow dosing by a user. Such medicament delivery devices may include, e.g., pumps, pens, and so on.

The ways provided may be unique to the situation encountered by different HCPs, e.g., may take account of the amount of time they may have available to spend with the patient, which may be either short or long. The different HCPs may include, e.g., endocrinologists, family practice doctors, certified diabetes educators, nurses, followers, and even other users. As the ways differ, the same may be provided with different amounts of information about the patient, e.g., followers may just get a glucose value, while endocrinologists may get analyzed pattern graphs, and so on.

The systems and methods relate not only to initial set up, but can also be used to update parameters and to send updated parameters to a user, either for direct and automatic modification of bolus calculator parameters or to allow the user to modify the parameters manually. In another implementation, the modifications can be downloaded and proposed to be automatically applied to the bolus calculator, but require confirmation by the user prior to actual modification of the parameters.

Systems and methods according to present principles do not generally only review past data in a retrospective fashion to determine the success or failure of a user's treatment of their diabetes. Using systems and methods described, a "give and take" can be enabled between the user, who is generating the data, and the doctor, who is reviewing the data and analyzing the same in concert with the patient. In the same way, the doctor can provide more significant and meaningful, as well as more frequent, updates to bolus calculator parameters as may be needed, to "hone in" on a best set of parameters or to determine the best set of parameters for a given situation of the patient, e.g., weekends versus weekdays.

In some cases, for example, insurance can allow an HCP to be reimbursed for the initial meeting and set up of the bolus calculator, even if the setup is done remotely. In the same way, transmission of an updated set of parameters, along with an optional HCP patient consultation, can give rise to another billing event. Updates of parameters can emanate not only from automatic algorithms, which are expected to be the most common source of such updates, but also from users. For example, if a user is habitually dosing one unit more than the bolus calculator suggests, and the user is getting satisfactory results, the bolus calculator parameters may be updated to automatically increase the dosing. In some cases, a notification of a suggested update may be sent to the HCP for confirmation and approval.

In one technique, for example, an HCP bolus calculator setup app could be provided to an HCP, e.g., via an invitation link (sent by text, email, etc., or via techniques noted above with respect to the flowcharts described below) from the patient user to the HCP, that would provide an interface for the HCP to set up bolus calculator parameters specific to the patient user and provide them back to the patient user's device for integration in the patient's bolus calculator. Using systems and methods according to present principles, a CGM enabled bolus calculator may be provided. Such provides a bolus calculator that is informed by various CGM aspects, including glucose trends. An HCP may be enabled to unlock the bolus calculator feature as well as to specify calculator parameters. In some implementations, the bolus calculator functionality may be disabled, e.g., when the CGM is connected to a pump, such that the pump calculator may take precedence over the CGM bolus calculator. Meal entry for the bolus calculator may be made "fuzzy", so that a user may more conveniently enter a meal size as small, average, or large. Parameters for these different meal sizes may be prescribed by the HCP during setup. Third party food database apps may be employed as inputs to the bolus calculator, with the input capable of being confirmed by the user, and the user may further be afforded the ability to override such values. The CGM app may further be enabled to compute IOB for MDI users within the context of the bolus calculator.

Generally, data from third party apps may be validated and/or authenticated prior to usage in a bolus calculator app. For example, the values may be 'grayed out' and not used in calculations until such time as the user confirms their accuracy. The bolus calculator app or functionality may allow user input of meal event data, e.g., entered carbs, and/or automatically pull meal event data from third-party applications, e.g., via Apple Healthkit. In this way, for example, when the user accesses their bolus calculator, recently entered carbs may be presented to them and the user may choose to use this amount in the bolus calculation, or to use a different value, e.g., taking into account a food soon to be eaten. In some cases the CGM app will not be able to validate the accuracy of carb estimates in other meal database applications, and may inform the user of that risk upon initial use.

The details of some example embodiments of the systems, methods, and devices of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

Overview

In some embodiments, a system is provided for continuous measurement of an analyte in a host. The system may include: a continuous analyte sensor configured to continuously measure a concentration of the analyte in the host, and a sensor electronics module physically connected to the continuous analyte sensor during sensor use. In certain embodiments, the sensor electronics module includes electronics configured to process a data stream associated with an analyte concentration measured by the continuous analyte sensor, in order to generate sensor information that includes raw sensor data, transformed sensor data, and/or any other sensor data, for example. The sensor electronics module may further be configured to generate sensor information that is customized for respective display devices, such that different display devices may receive different sensor information.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, and/or reaction products. In some implementations, the analyte for measurement by the methods or devices is glucose. However, other analytes are contemplated as well, including but not limited to: acarboxyprothrombin; acetoacetic acid; acetone; Acetyl CoA; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; ketone bodies; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, isoprene (2-methyl-1,3-butadiene), *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, Flavivirus (for example deer tick, dengue fever, Powassan, West Nile, yellow fever, or Zika virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain implementations. The analyte can be naturally present in the biological fluid, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon, ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA), and intermediaries in the Citric Acid Cycle.

Alerts

In certain embodiments, one or more alerts are associated with a sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g., an alert may be based on sensor data from both a glucose sensor and a temperature sensor). For example, a hypoglycemic alert may include alert conditions indicating a minimum required trend in the host's glucose level that must be present before triggering the alert. The term "trend", as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In certain embodiments, each of the alerts is associated with one or more actions that are to be performed in response to triggering of the alert. Alert actions may include, for example, activating an alarm, such as displaying information on a display of the sensor electronics module or activating an audible or vibratory alarm coupled to the sensor electronics module, and/or transmitting data to one or more display devices external to the sensor electronics module. For any delivery action that is associated with a triggered alert, one or more delivery options define the content and/or format of the data to be transmitted, the device to which the data is to be transmitted, when the data is to be transmitted, and/or a communication protocol for delivery of the data. Alerts may also result in a bolus calculator parameter/setting modification trigger being activated, and a consequent signal being generated and transmitted to an HCP server, as described in greater detail below.

In certain embodiments, multiple delivery actions (each having respective delivery options) may be associated with a single alert such that displayable sensor information having different content and formatting, for example, is transmitted to respective display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module in response to triggering of a common alert. Advantageously, the sensor electronics module is not tied to a single display device, rather it is configured to communicate with a plurality of different display devices directly, systematically, simultaneously (e.g., via broadcasting), regularly, periodically, randomly, on-demand, in response to a query, based on alerts or alarms, and/or the like.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system is configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more display devices within communication range of the sensor electronics module and to wirelessly communicate sensor information (e.g., a data package including displayable sensor information, one or more alarm conditions, and/or other alarm information) thereto. Accordingly, the display device is configured to display at least some of the sensor information and/or alarm the host (and/or care taker), where the alarm mechanism is located on the display device.

In some embodiments, the sensor electronics module is configured to provide one or a plurality of different alarms via the sensor electronics module and/or via transmission of a data package indicating an alarm should be initiated by one or a plurality of display devices (e.g., sequentially and/or simultaneously). In certain embodiments, the sensor electronics module merely provides a data field indicating that an alarm conditions exists and the display device, upon reading the data field indicating the existence of the alarm condition, may decide to trigger an alarm. In some embodiments, the sensor electronics module determines which of the one or more alarms to trigger based on one or more alerts that are triggered. For example, when an alert trigger indicates severe hypoglycemia, the sensor electronics module can perform multiple actions, such as activating an alarm on the sensor electronics module, transmitting a data package to a monitoring device indicating activation of an alarm on the display, and transmitting a data package as a text message to a care provider. As an example, a text message can appear on a custom monitoring device, cell phone, pager device, and/or the like, including displayable sensor information that indicates the host's condition (e.g., "severe hypoglycemia").

In some embodiments, the sensor electronics module is configured to wait a time period for the host to respond to a triggered alert (e.g., by pressing or selecting a snooze and/or off function and/or button on the sensor electronics module and/or a display device), after which additional alerts are triggered (e.g., in an escalating manner) until one or more alerts are responded to. In some embodiments, the sensor electronics module is configured to send control signals (e.g., a stop signal) to a medical device associated with an alarm condition (e.g., hypoglycemia), such as an insulin pump, where the stop alert triggers a stop of insulin delivery via the pump.

In some embodiments, the sensor electronics module is configured to directly, systematically, simultaneously (e.g., via broadcasting), regularly, periodically, randomly, on-demand, in response to a query (from the display device), based on alerts or alarms, and/or the like transmit alarm information. In some embodiments, the system further includes a repeater such that the wireless communication distance of the sensor electronics module can be increased, for example, to 10, 20, 30, 50 75, 100, 150, or 200 meters or more, where the repeater is configured to repeat a wireless communication from the sensor electronics module to the display device located remotely from the sensor electronics module. A repeater can be useful to families having children with diabetes. For example, to allow a parent to carry, or place in a stationary position, a display device, such as in a large house where the parents sleep at a distance from the child.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, where a failed attempt at communication with and/or alarming with a first display device triggers an attempt at communication with and/or alarming with a second display device, and so on. In one example embodiment, the sensor electronics module is configured to search for and attempt to alarm a host or care provider sequentially using a list of display devices, such as: (1) a default display device or a custom analyte monitoring device; (2) a mobile phone via auditory and/or visual methods, such as, text message to the host and/or care provider, voice message to the host and/or care provider, and/or 911); (3) a tablet; (4) a smart watch or bracelet; and/or (5) smart glasses or other wearable display device.

Depending on the embodiment, one or more display devices that receive data packages from the sensor electronics module are "dummy displays", where they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may include software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, tablets, PDAs, PCs and the like).

In some embodiments, certain display devices may be in direct wireless communication with the sensor electronics module, but intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, where the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, where the receiver enables direct wireless communication when substantive processing of the sensor information does not occur. In certain embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In certain embodiments, one or more display devices include built-in authentication mechanisms, where authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. This may be referred to in some cases as two-way authentication.

In some embodiments, one or more display devices are configured to query the sensor electronics module for displayable sensor information, where the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how sensor information is obtained.

In some embodiments, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with embodiments disclosed herein.

In general, a plurality of display devices (e.g., a custom analyte monitoring device (which may also be referred to as an analyte display device), a mobile phone, a tablet, a smart watch, a reference analyte monitor, a drug delivery device, a medical device and a personal computer) may be configured to wirelessly communicate with the sensor electronics module. The plurality of display devices may be configured to display at least some of the displayable sensor information wirelessly communicated from the sensor electronics module. The displayable sensor information may include sensor data, such as raw data and/or transformed sensor data, such as analyte concentration values, rate of change information, trend information, alert information, sensor diagnostic information and/or calibration information, for example.

Analyte Sensor

With reference to FIG. 1A, in some embodiments, analyte sensor 10 includes a continuous analyte sensor, for example, a subcutaneous, transdermal (e.g., transcutaneous), or intravascular device. In some embodiments, such a sensor or device can analyze a plurality of intermittent blood samples. While the present disclosure includes embodiments of glucose sensors, such embodiments may be used for other analytes as well. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. According to one example embodiment described below, an implantable glucose sensor may be used. However, it should be understood that the devices and methods described herein can be applied to any device capable of detecting a concentration of glucose and providing an output signal that represents the concentration of glucose (e.g., as a form of analyte data).

In certain embodiments, analyte sensor 10 is an implantable glucose sensor, such as described with reference to U.S. Pat. No. 6,001,067 and U.S. Patent Publication No. US-2005-0027463-A1. In embodiments, analyte sensor 10 is a transcutaneous glucose sensor, such as described with reference to U.S. Patent Publication No. US-2006-0020187-A1. In embodiments, analyte sensor 10 is configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007. In embodiments, the continuous glucose sensor includes a transcutaneous sensor such as described in U.S. Pat. No. 6,565,509 to Say et al., for example. In embodiments, analyte sensor 10 is a continuous glucose sensor that includes a subcutaneous sensor such as described with reference to U.S. Pat. No. 6,579,690 to Bonnecaze et al. or U.S. Pat. No. 6,484,046 to Say et al., for example. In embodiments, the continuous glucose sensor includes a refillable subcutaneous sensor such as described with reference to U.S. Pat. No. 6,512,939 to Colvin et al., for example. The continuous glucose sensor may include an intravascular sensor such as described with reference to U.S. Pat. No. 6,477,395 to Schulman et al., for example. The continuous glucose sensor may include an intravascular sensor such as described with reference to U.S. Pat. No. 6,424,847 to Mastrototaro et al., for example.

Figure 2A:
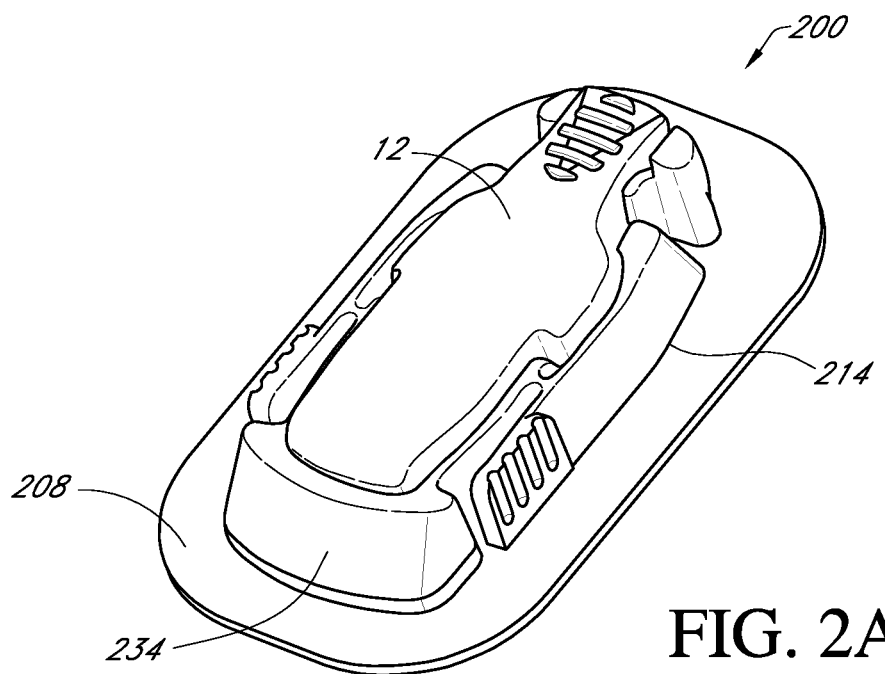
FIG. 2A is a perspective view of an example enclosure that may be used in connection with implementing embodiments of an analyte sensor system.
Figure 2B:
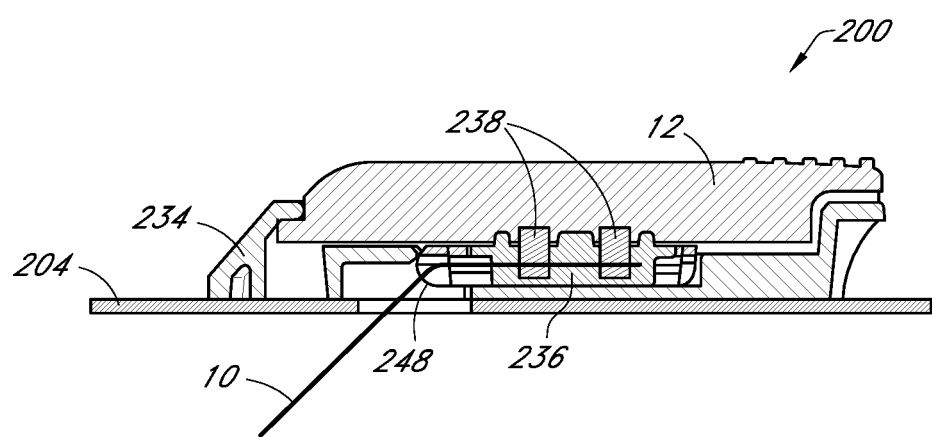
FIG. 2B is a side view of an example enclosure that may be used in connection with implementing embodiments of an analyte sensor system.

FIGS. 2A and 2B are perspective and side views of enclosure 200 that may be used in connection with implementing embodiments of analyte sensor system 8, according certain aspects of the present disclosure. Enclosure 200 includes mounting unit 214 and sensor electronics module 12 attached thereto in certain embodiments. Enclosure 200 is shown in a functional position, including mounting unit 214 and sensor electronics module 12 matingly engaged therein. In some embodiments, mounting unit 214, also referred to as a housing or sensor pod, includes base 234 adapted for fastening to a host's or user's skin. Base 234 can be formed from a variety of hard or soft materials, and can include a low profile for minimizing protrusion of the device from the host during use. In some embodiments, base 234 is formed at least partially from a flexible material, which may provide numerous advantages over other transcutaneous sensors, which, unfortunately, can suffer from motion-related artifacts associated with the host's movement when the host is using the device. Mounting unit 214 and/or sensor electronics module 12 can be located over the sensor insertion site to protect the site and/or provide a minimal footprint (utilization of surface area of the host's skin).

In some embodiments, a detachable connection between mounting unit 214 and sensor electronics module 12 is provided, which enables improved manufacturability, namely, the potentially relatively inexpensive mounting unit 214 can be disposed of when refurbishing or maintaining analyte sensor system 8, while the relatively more expensive sensor electronics module 12 can be reusable with multiple sensor systems. In some embodiments, sensor electronics module 12 is configured with signal processing (programming), for example, configured to filter, calibrate, and/or execute other algorithms useful for calibration and/or display of sensor information. However, an integral (non-detachable) sensor electronics module can be configured.

In some embodiments, contacts 238 are mounted on or in a subassembly hereinafter referred to as contact subassembly 236 configured to fit within base 234 of mounting unit 214 and hinge 248 that allows contact subassembly 236 to pivot between a first position (for insertion) and a second position (for use) relative to mounting unit 214. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, contacts 238 are formed from a conductive elastomeric material, such as a carbon black elastomer, through which sensor 10 extends.

With further reference to FIGS. 2A and 2B, in certain embodiments, mounting unit 214 is provided with adhesive pad 208, disposed on the mounting unit's back surface and includes a releasable backing layer. Thus, removing the backing layer and pressing at last a portion of base 234 of mounting unit 214 onto the host's skin adheres mounting unit 214 to the host's skin. Additionally or alternatively, an adhesive pad can be placed over some or all of analyte sensor system 8 and/or sensor 10 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2A and 2B are described in more detail with reference to U.S. Pat. No. 7,310,544, which is incorporated herein by reference in its entirety. Configurations and arrangements can provide water resistant, waterproof, and/or hermetically sealed properties associated with the mounting unit/sensor electronics module embodiments described herein.

Various methods and devices that are suitable for use in conjunction with aspects of some embodiments are disclosed in U.S. Patent Publication No. US-2009-0240120-A1, which is incorporated herein by reference in its entirety for all purposes.

Example Configurations

Referring again to FIG. 1A, system 100 that may be used in connection with implementing aspects of an analyte sensor system is depicted. In some cases, system 100 may be used to implement various systems described herein. System 100 in embodiments includes analyte sensor system 8 and display devices 110, 120, 130, and 140, according to certain aspects of the present disclosure. Analyte sensor system 8 in the illustrated embodiment includes sensor electronics module 12 and continuous analyte sensor 10 associated with the sensor electronics module 12. Sensor electronics module 12 may be in wireless communication (e.g., directly or indirectly) with one or more of display devices 110, 120, 130, and 140. In embodiments, system 100 also includes medical device 136 and server system 134. Sensor electronics module 12 may also be in wireless communication (e.g., directly or indirectly) with medical device 136 and server system 134. In some examples, display devices 110-140 may also be in wireless communication with the server system 134 and/or the medical device 136.

In certain embodiments, sensor electronics module 12 includes electronic circuitry associated with measuring and processing the continuous analyte sensor data, including prospective algorithms associated with processing and calibration of the sensor data. Sensor electronics module 12 can be physically connected to continuous analyte sensor 10 and can be integral with (non-releasably attached to) or releasably attachable to continuous analyte sensor 10. Sensor electronics module 12 may include hardware, firmware, and/or software that enables measurement of levels of the analyte via a glucose sensor. For example, sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor.

Sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes.

Referring again to FIG. 1A, display devices 110, 120, 130, and/or 140 are configured for displaying (and/or alarming) the displayable sensor information that may be transmitted by sensor electronics module 12 (e.g., in a customized data package that is transmitted to the display devices based on their respective preferences). Each of display devices 110, 120, 130, or 140 can include a display such as a touchscreen display 112, 122, 132, /or 142 for displaying sensor information and/or analyte data to a user and/or receiving inputs from the user. For example, a graphical user interface may be presented to the user for such purposes. In some embodiments, the display devices may include other types of user interfaces such as voice user interface instead of or in addition to a touchscreen display for communicating sensor information to the user of the display device and/or receiving user inputs. In some embodiments, one, some, or all of the display devices is configured to display or otherwise communicate the sensor information as it is communicated from the sensor electronics module (e.g., in a data package that is transmitted to respective display devices), without any additional prospective processing required for calibration and real-time display of the sensor data.

Figure 1B:
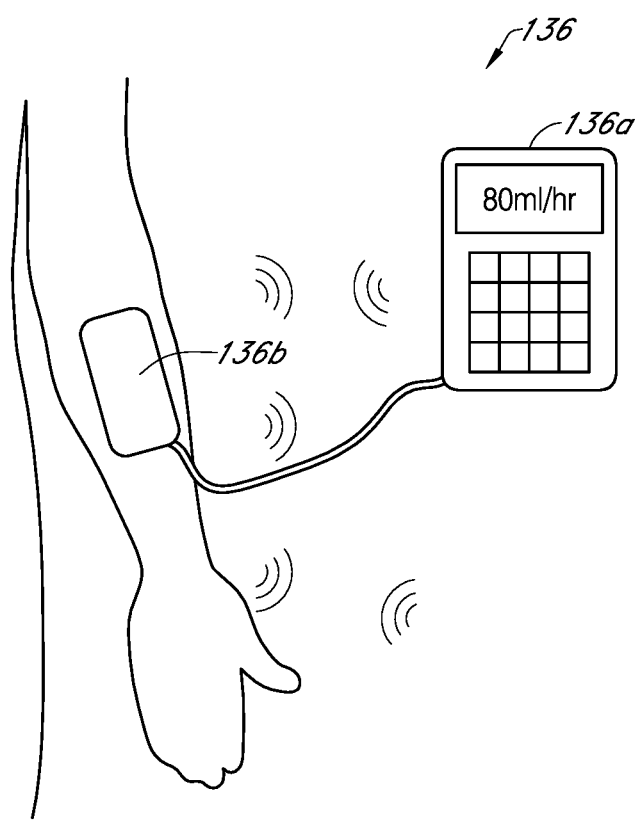
FIG. 1B illustrates aspects of an example system that may be used in connection with implementing embodiments of the disclosure.

Medical device 136 may be a passive device in example embodiments of the disclosure. For example medical device 136 may be an insulin pump for administering insulin to a user, as shown in FIG. 1B. For a variety of reasons, it may be desirable for such an insulin pump to receive and track glucose values transmitted from analyte sensor system 8. One reason is to provide the insulin pump a capability to suspend or activate insulin administration when a glucose value falls below a threshold value. One solution that allows a passive device (e.g., medical device 136) to receive analyte data (e.g., glucose values) without being bonded to analyte sensor system 8 is to include the analyte data in the advertisement messages transmitted from analyte sensor system 8. The data included in the advertisement messages can be encoded so that only a device that has the identification information associated with analyte sensor system 8 can decode the analyte data. In some embodiments, the medical device 136 includes a sensor apparatus 136b, e.g., attachable or wearable by the user, in wired or wireless communication with a dedicated monitor or display apparatus 136a to process sensor data and/or display data from the sensor apparatus 136a and/or receive input for operation of the sensor apparatus and/or data processing.

With further reference to FIG. 1A, the plurality of display devices may include a custom display device specially designed for displaying certain types of displayable sensor information associated with analyte data received from sensor electronics module 12 (e.g., a numerical value and an arrow, in some embodiments). Analyte display device 110 is an example of such a custom device. In some embodiments, one of the plurality of display devices is smartphone, such as mobile phone 120 based on an Android, iOS or other operating system, and configured to display a graphical representation of the continuous sensor data (e.g., including current and historic data). Other display devices can include other hand-held devices, such as tablet 130, smart watch 140, medical device 136 (e.g., an insulin delivery device or a blood glucose meter), and/or a desktop or laptop computer.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1A, a plurality of different display devices can be in direct wireless communication with a sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

As further illustrated in FIG. 1A, system 100 may also include wireless access point (WAP) 138 that may be used to couple one or more of analyte sensor system 8, the plurality display devices, server system 134, and medical device 136 to one another. For example, WAP 138 may provide Wi-Fi and/or cellular connectivity within system 100. Near Field Communication (NFC) may also be used among devices of system 100. Server system 134 may be used to collect analyte data from analyte sensor system 8 and/or the plurality of display devices, for example, to perform analytics thereon, generate universal or individualized models for glucose levels and profiles, and so on. One implementation of the server system 134 may be employed to receive bolus calculator trigger events from user mobile devices, and/or to determine the same from received user sensor signal data.

Figure 3A:
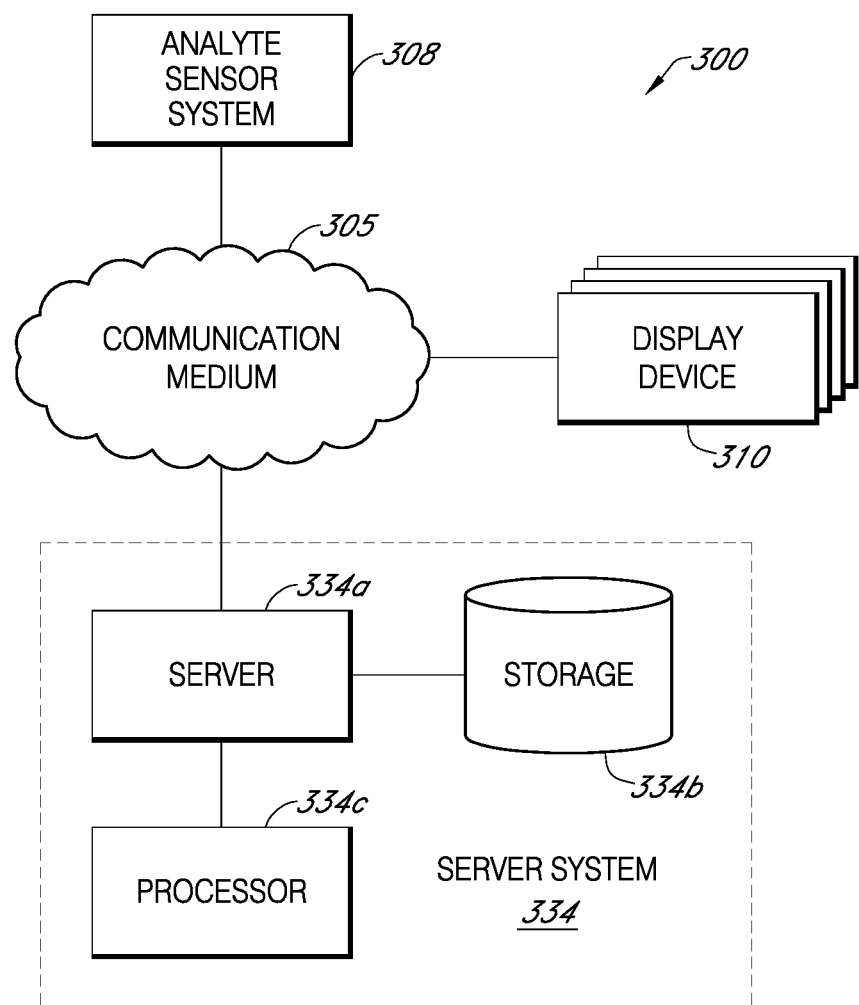
FIG. 3A illustrates aspects of an example system that may be used in connection with implementing embodiments of the disclosure.

Referring now to FIG. 3A, system 300 is depicted. System 300 may be used in connection with implementing embodiments of the disclosed systems, methods, and devices. By way of example, the various below-described components of FIG. 3A may be used to provide wireless communication of glucose data, for example between an analyte sensor system and a plurality of display devices, medical devices, servers and so on, such as those shown in FIG. 1A.

As shown in FIG. 3A, system 300 may include analyte sensor system 308 and one or more display devices 310. Additionally, in the illustrated embodiment, system 300 includes server system 334, which in turn includes server 334a coupled to processor 334c and storage 334b. Analyte sensor system 308 may be coupled to display devices 310 and/or server system 334 via communication medium 305, such as to, e.g., communicate sensor data which may be employed to determine if a bolus calculator parameter or setting requires modification.

As will be described in detail herein, analyte sensor system 308 and display devices 310 may exchange messaging via communication medium 305, and communication medium 305 may also be used to deliver analyte data to display devices 310 and/or server system 334. As alluded to above, display devices 310 may include a variety of electronic computing devices, such as, for example, a smartphone, tablet, laptop, wearable device, etc. Display devices 310 may also include analyte display device 110 and medical device 136. Here, it will be noted that a GUI of display device 310 may perform such functions as accepting user input and displaying menus as well as information derived from analyte data. The GUI may be provided by various operating systems known in the art, such as, for example, iOS, Android, Windows Mobile, Windows, Mac OS, Chrome OS, Linux, Unix, a gaming platform OS (e.g., Xbox, PlayStation, Wii), etc. In various embodiments, communication medium 305 may be based on one or more wireless communication protocols such as Bluetooth, Bluetooth Low Energy (BLE), ZigBee, Wi-Fi, 802.11 protocols, Infrared (IR), Radio Frequency (RF), 2G, 3G, 4G, etc., and/or wired protocols and media.

In various embodiments, the elements of system 300 may be used to perform various processes described herein and/or may be used to execute various operations described herein with regard to one or more disclosed systems and methods. Upon studying the present disclosure, one of skill in the art will appreciate that system 300 may include multiple analyte sensor systems, communication media 305, and/or server systems 334.

As mentioned, communication medium 305 may be used to connect or communicatively couple analyte sensor system 308, display devices 310, and/or server system 334 to one another or to a network, and communication medium 305 may be implemented in a variety of forms. For example, communication medium 305 may include an Internet connection, such as a local area network (LAN), a wide area network (WAN), a fiber optic network, internet over power lines, a hard-wired connection (e.g., a bus), and the like, or any other kind of network connection. Communication medium 305 may be implemented using any combination of routers, cables, modems, switches, fiber optics, wires, radio (e.g., microwave/RF links), and the like. Further, communication medium 305 may be implemented using various wireless standards, such as Bluetooth®, BLE, Wi-Fi, 3GPP standards (e.g., 2G GSM/GPRS/EDGE, 3G UMTS/CDMA2000, or 4G LTE/LTE-U), etc. Upon reading the present disclosure, one of skill in the art will recognize other ways to implement communication medium 305 for communications purposes.

Server 334a may receive, collect, or monitor information, including analyte data and related information, from analyte sensor system 308 and/or display device 310, such as input responsive to the analyte data or input received in connection with an analyte monitoring application running on analyte sensor system or display device 310. In such cases, server 334a may be configured to receive such information via communication medium 305. This information may be stored in storage 334b and may be processed by processor 334c. For example, processor 334c may include an analytics engine capable of performing analytics on information that server 334a has collected, received, etc. via communication medium 305. In embodiments, server 334a, storage 334b, and/or processor 334c may be implemented as a distributed computing network, such as a Hadoop® network, or as a relational database or the like.

Server 334a may include, for example, an Internet server, a router, a desktop or laptop computer, a smartphone, a tablet, a processor, a module, or the like, and may be implemented in various forms, including, for example, an integrated circuit or collection thereof, a printed circuit board or collection thereof, or in a discrete housing/package/rack or multiple of the same. In embodiments, server 334a at least partially directs communications made over communication medium 305. Such communications include the delivery and/or messaging (e.g., advertisement, command, or other messaging) and analyte data. For example, server 334a may process and exchange messages between analyte sensor system 308 and display devices 310 related to frequency bands, timing of transmissions, security, alarms, and so on. Server 334a may update information stored on analyte sensor system 308 and/or display devices 310, for example, by delivering applications thereto. Server 334a may send/receive information to/from analyte sensor system 308 and/ or display devices 310 in real time or sporadically. Further, server 334a may implement cloud computing capabilities for analyte sensor system 308 and/or display devices 310.

Figure 3B:
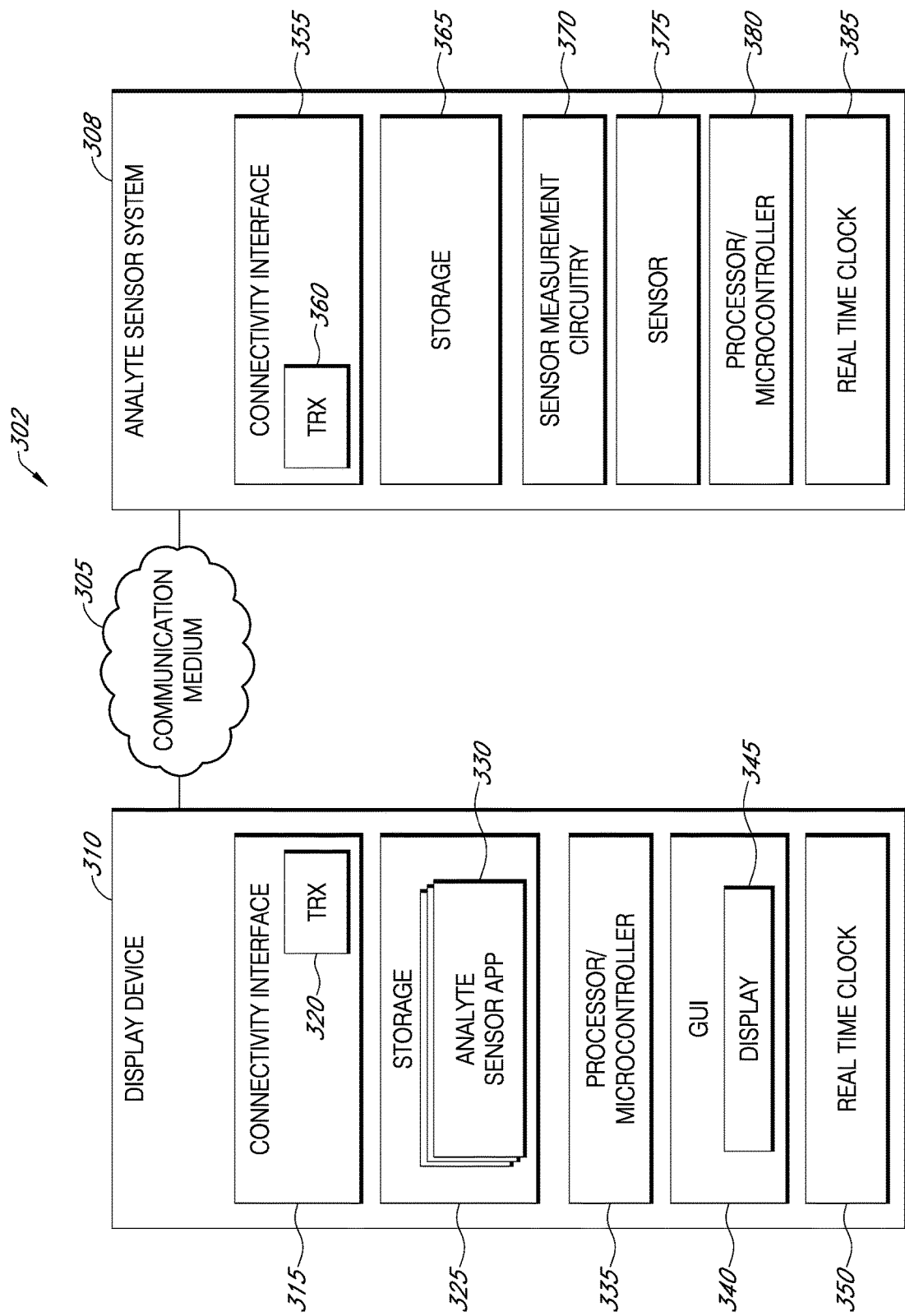
FIG. 3B illustrates aspects of an example system that may be used in connection with implementing embodiments of the disclosure.

FIG. 3B depicts system 302, which includes examples of additional aspects of the present disclosure that may be used in connection implementing an analyte sensor system. As illustrated, system 302 may include analyte sensor system 308. As shown, analyte sensor system 308 may include analyte sensor 375 (e.g., which may also be designated with the numeral 10 in FIG. 1A) coupled to sensor measurement circuitry 370 for processing and managing sensor data. Sensor measurement circuitry 370 may be coupled to processor/microprocessor 380 (e.g., which may be part of item 12 in FIG. 1A). In some embodiments, processor 380 may perform part or all of the functions of the sensor measurement circuitry 370 for obtaining and processing sensor measurement values from sensor 375. Processor 380 may be further coupled to a radio unit or transceiver 320 (e.g., which may be part of item 12 in FIG. 1A) for sending sensor data and receiving requests and commands from an external device, such as display device 310, which may be used to display or otherwise provide the sensor data (or analyte data) to a user. As used herein, the terms "radio unit" and "transceiver" are used interchangeably and generally refer to a device that can wirelessly transmit and receive data. Analyte sensor system 308 may further include storage 365 (e.g., which may be part of item 12 in FIG. 1A) and real time clock (RTC) 380 (e.g., which may be part of item 12 in FIG. 1A) for storing and tracking sensor data.

As alluded to above, wireless communication protocols may be used to transmit and receive data between analyte sensor system 308 and the display device 310 via communication medium 305. Such wireless protocols may be designed for use in a wireless network that is optimized for periodic and small data transmissions (that may be transmitted at low rates if necessary) to and from multiple devices in a close range (e.g., a personal area network (PAN)). For example, one such protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing overhead) to reduce power consumption. In some embodiments, burst broadcasting schemes (e.g., one way communication) may be used. This may eliminate overhead required for acknowledgement signals and allow for periodic transmissions that consume little power.

The protocols may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as Wi-Fi, Bluetooth and Bluetooth Low Energy (BLE). The wireless protocol may operate in various frequency bands such as an open ISM band such as 2.4 GHz. Furthermore, to reduce power usage, the wireless protocol may adaptively configure data rates according to power consumption.

With further reference to FIG. 3B, system 302 may include display device 310 communicatively coupled to analyte sensor system 308 via communication medium 305. In the illustrated embodiment, display device 310 includes connectivity interface 315 (which in turn includes transceiver 320), storage 325 (which in turn stores analyte sensor application 330 and/or additional applications), processor/microprocessor 335, graphical user interface (GUI) 340 that may be presented using display 345 of display device 310, and real time clock (RTC) 350. A bus (not shown here) may be used to interconnect the various elements of display device 310 and transfer data between these elements.

Display device 310 may be used for alerting and providing sensor information or analyte data to a user, and may include a processor/microprocessor 335 for processing and managing sensor data. Display device 310 may include display 345, storage 325, analyte sensor application 330, and real time clock 350 for displaying, storing, and tracking sensor data. Display device 310 may further include a radio unit or transceiver 320 coupled to other elements of display device 310 via connectivity interface 315 and/or a bus. Transceiver 320 may be used for receiving sensor data and for sending requests, instructions, and/or data to analyte sensor system 308. Transceiver 320 may further employ a communication protocol. Storage 325 may also be used for storing an operating system for display device 310 and/or a custom (e.g., proprietary) application designed for wireless data communication between a transceiver and display device 310. Storage 325 may be a single memory device or multiple memory devices and may be a volatile or non-volatile memory for storing data and/or instructions for software programs and applications. The instructions may be executed by processor 335 to control and manage transceiver 320.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, processor 335, 380 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver 320, 360.

Components of analyte sensor system 308 may require replacement periodically. For example, analyte sensor system 308 may include an implantable sensor 375 that may be attached to a sensor electronics module that includes sensor measurement circuitry 370, processor 380, storage 365, and transceiver 360, and a battery (not shown). Sensor 375 may require periodic replacement (e.g., every 7 to 30 days). The sensor electronics module may be configured to be powered and active for much longer than sensor 375 (e.g., for three to six months or more) until the battery needs replacement. Replacing these components may be difficult and require the assistance of trained personnel. Reducing the need to replace such components, particularly the battery, significantly improves the convenience and cost of using analyte sensor system 308, including to the user. In some embodiments, when a sensor electronic module is used for the first time (or reactivated once a battery has been replaced in some cases), it may be connected to sensor 375 and a sensor session may be established. As will be further described below, there may be a process for initially establishing communication between display device 310 and the sensor electronics module when the module is first used or re-activated (e.g., the battery is replaced). Once display device 310 and sensor electronics module have established communication, display device 310 and the sensor electronics module may periodically and/or continuously be in communication over the life of several sensors 375 until, for example, the battery needs to be replaced. Each time sensor 375 is replaced, a new sensor session may be established. The new sensor session may be initiated through a process completed using display device 310 and the process may be triggered by notifications of a new sensor via the communication between the sensor electronics module and display device 310 that may be persistent across sensor sessions.

Analyte sensor system 308 typically gathers analyte data from sensor 375 and transmits the same to display device 310. Data points regarding analyte values may be gathered and transmitted over the life of sensor 375 (e.g., in the range of 1 to 30 days or more). New measurements may be transmitted often enough to adequately monitor glucose levels. Rather than having the transmission and receiving circuitry of each of analyte sensor system 308 and display device 310 continuously communicating, analyte sensor system 308 and display device 310 may regularly and/or periodically establish a communication channel between them. Thus, analyte sensor system 308 can in some cases communicate via wireless transmission with display device 310 (e.g., a hand-held computing device, medical device, or proprietary device) at predetermined time intervals. The duration of the predetermined time interval can be selected to be long enough so that analyte sensor system 308 does not consume too much power by transmitting data more frequently than needed, yet frequent enough to provide substantially real-time sensor information (e.g., measured glucose values or analyte data) to display device 310 for output (e.g., via display 345) to a user. While the predetermined time interval is every five minutes in some embodiments, it is appreciated that this time interval can be varied to be any desired length of time.

With continued reference to FIG. 3B, as shown, connectivity interface 315 interfaces display device 310 to communication medium 305, such that display device 310 may be communicatively coupled to analyte sensor system 308 via communication medium 305. Transceiver 320 of connectivity interface 315 may include multiple transceiver modules operable on different wireless standards. Transceiver 320 may be used to receive analyte data and associated commands and messages from analyte sensor system 308. Additionally, connectivity interface 315 may in some cases include additional components for controlling radio and/or wired connections, such as baseband and/or Ethernet modems, audio/video codecs, and so on.

Storage 325 may include volatile memory (e.g., RAM) and/or non-volatile memory (e.g., flash storage), may include any of EPROM, EEPROM, cache, or may include some combination/variation thereof. In various embodiments, storage 325 may store user input data and/or other data collected by display device 310 (e.g., input from other users gathered via analyte sensor application 330). Storage 325 may also be used to store volumes of analyte data received from analyte sensor system 308 for later retrieval and use, e.g., for determining trends and triggering alerts. Additionally, storage 325 may store analyte sensor application 330 that, when executed using processor 335, for example, receives input (e.g., by a conventional hard/soft key or a touch screen, voice detection, or other input mechanism), and allows a user to interact with the analyte data and related content via GUI 340, as will be described in further detail herein.

In various embodiments, a user may interact with analyte sensor application 330 via GUI 340, which may be provided by display 345 of display device 310. By way of example, display 345 may be a touchscreen display that accepts various hand gestures as inputs. Application 330 may process and/or present analyte-related data received by display device 310, according to various operations described herein, and present such data via display 345. Additionally, application 330 may be used to obtain, access, display, control, and/or interface with analyte data and related messaging and processes associated with analyte sensor system 308, as is described in further detail herein.

Application 330 may be downloaded, installed, and initially configured/setup on display device 310. For example, display device 310 may obtain application 330 from server system 334, or from another source accessed via a communication medium (e.g., communication medium 305), such as an application store or the like. Following installation and setup, application 330 may be used to access and/or interface with analyte data (e.g., whether stored on server system 334, locally from storage 325, or from analyte sensor system 308). By way of illustration, application 330 may present a menu that includes various controls or commands that may be executed in connection with the operating of analyte sensor system 308 and one or more display devices 310. Application 330 may also be used to interface with or control other display devices 310, for example, to deliver or make available thereto analyte data, including for example by receiving/sending analyte data directly to the other display device 310 and/or by sending an instruction for analyte sensor system 308 and the other display device 310 to be connected, etc., as will be described herein. In some implementations, application 330 may interact with other application(s) of the display device to retrieve or provide relevant data, e.g., such as other health data.

Analyte sensor application 330 may include various code/functional modules, such as, for example, a display module, a menu module, a list module, and so on as will become clear in light of the description of various functionalities herein (e.g., in connection with disclosed methods). These modules may be implemented separately or in combination. Each module may include computer-readable media and have computer-executable code stored thereon, such that the code may be operatively coupled to and/or executed by processor 335 (which, e.g., may include a circuitry for such execution) to perform specific functions (e.g., as described herein with regard to various operations and flow charts etc.) with respect to interfacing with analyte data and performing tasks related thereto. As will be further described below, a display module may present (e.g., via display 345) various screens to a user, with the screens containing graphical representations of information provided by application 330. In further embodiments, application 330 may be used to display to the user an environment for viewing and interacting with various display devices that may be connectable to analyte sensor system 308, as well as with analyte sensor system 308 itself. Sensor application 330 may include a native application modified with a software design kit (e.g., depending on the operating system) in order to carry out the functionalities/features described herein.

Referring again to FIG. 3B, display device 310 also includes processor 335. Processor 335 may include processor sub-modules, including, by way of example, an applications processor that interfaces with and/or controls other elements of display device 310 (e.g., connectivity interface 315, application 330, GUI 340, display 345, RTC 350, etc.). Processor 335 may include a controller and/or microcontroller that provides various controls (e.g., interfaces with buttons and switches) related to device management, such as, for example, lists of available or previously paired devices, information related to measurement values, information related to network conditions (e.g., link quality and the like), information related to the timing, type, and/or structure of messaging exchanged between analyte sensor system 308 and display device 310, and so on. Additionally, the controller may include various controls related to the gathering of user input, such as, for example, a user's finger print (e.g., to authorize the user's access to data or to be used for authorization/encryption of data, including analyte data), as well as analyte data.

Processor 335 may include circuitry such as logic circuits, memory, a battery and power circuitry, and other circuitry drivers for periphery components and audio components. Processor 335 and any sub-processors thereof may include logic circuits for receiving, processing, and/or storing data received and/or input to display device 310, and data to be transmitted or delivered by display device 310. Processor 335 may be coupled by a bus to display 345 as well as connectivity interface 315 and storage 325 (including application 330). Hence, processor 335 may receive and process electrical signals generated by these respective elements and thus perform various functions. By way of example, processor 335 may access stored content from storage 325 at the direction of application 330, and process the stored content for display and/or output by display 345. Additionally, processor 335 may process the stored content for transmission via connectivity interface 315 and communication medium 305 to other display devices 310, analyte sensor system 308, or server system 334. Display device 310 may include other peripheral components not shown in detail in FIG. 3B.

In further embodiments, processor 335 may further obtain, detect, calculate, and/or store data input by a user via display 345 or GUI 340, or data received from analyte sensor system 308 (e.g., analyte sensor data or related messaging), over a period of time. Processor 335 may use this input to gauge the user's physical and/or mental response to the data and/or other factors (e.g., time of day, location, etc.). In various embodiments, the user's response or other factors may indicate preferences with respect to the use of certain display devices 310 under certain conditions, and/or the use of certain connection/transmission schemes under various conditions, as will be described in further detail herein.

It should be noted at this juncture that like-named elements as between display device 310 and analyte sensor system 308 may include similar features, structures, and/or capabilities. Therefore, with respect to such elements, the description of display device 310 above may in some cases be applied to analyte sensor system 308.

CGM-Based Bolus Calculator

As noted above, it is generally important to obtain HCP input as to parameters used in bolus calculators, as well as in related (and sometimes connected) devices such as medicament delivery devices. Generally, where HCPs are in signal communication with patients, such as via wired or wireless networks, certain safety and security features should be provided to ensure that prescriptions are delivered to the correct patient and that any given patient's prescription is maintained in confidentiality.

Desirable and/or useful features for systems in which HCPs are involved in bolus calculator set up include an encrypted system, including, e.g., an encrypted email system, to allow back-and-forth communications between the HCP and the patient, for the communication of bolus calculator parameters including data files comprising the same. It is further important to allow and enable integration into an electronic medical record (EMR). It is further important to enable multiple points of verification such that an HCP is ensured they are working on the correct patient's file.

Generally, patient reports, e.g., a PDF of a 14 day report, may be configured to be uploaded directly to the EMR and printable for review by the HCP. Using the signal communications enabled as are described in greater detail below, the HCP may be informed if the patient is staying high or is having a hypoglycemic event. Patients may select whether to be reminded about their medication or not. The home screen of the patient's device may show trends, a blood glucose value, whether or not the patient is in range, high and low thresholds (usually set by the HCP) events with date/time stamps, e.g., indications of meals, exercise, sleep, statistics, including to allow the comparison of one day against another, and so on. Patients can be enabled using the systems to easily figure out for themselves "cause-and-effect", based on what they see on their home screen, and in this way the patient may be enabled (and derive confidence from) figuring out what affects their blood sugar by themselves.

Reports provided to an HCP may include an indication of average blood glucose, average A1c, frequency of hypoglycemic events, percentages of time in range and out of range (including whether the time out of range is above or below the target range), results overlaid on top of each other to illustrate trends, posted events pertaining to nutrition, stress, activity, exercise, sleep, illness, infections, and so on. An electronic report having various levels of detail about the above-noted aspects may be exported, e.g., in PDF format, to the HCPs EMR for the patient. The report is generally available shortly after the HCP has reviewed the same with the patient, so information may be grouped in the report so as to be highlighted. For example, information that is most critical to making a decision for the patient may be highlighted or placed in the report so as to be immediately available.

Returning to the secure communications of BC/drug delivery parameters, it is important to facilitate not only the communication of initial parameters but also to facilitate the update of bolus calculator and drug delivery parameters determined by the system and transmitted to the patient's bolus calculator, such updated parameters being responsive to the patient's dose-response metrics assessed after initial set up and/or previous updates. In many implementations, systems and methods according to present principles take advantage of specific inputs, such as CGM data, which was not available in prior bolus calculators and pump set up routines. Certain third-party data may also be employed in bolus calculator set up. Finally, insulin data, if available, may also be employed, depending upon implementation.

Systems and methods according to present principles provide software, hardware, algorithms, and workflow processes for an HCP to set up a personalized bolus calculator, particularly on a CGM system, safely and efficiently. The disclosed systems and methods provide intelligent and efficient methods for the initial set up of the bolus calculator parameters for the bolus calculator tool by the HCP, including, e.g., the setup of carbohydrate counts for basic meals like a small/medium/large breakfast, lunch, or dinner. The disclosed systems and methods also provide methods for HCPs to initially set parameters such as insulin-to-carb ratio (ICR), glucose targets and thresholds, insulin action times, so as to safely enable the operation of the bolus calculator by the patients/users. The bolus calculator app (or CGM app with bolus calculator tool) can provide warning statements in the bolus calculator menu prior to initial set up, informing the user of the dangers and risks in setting up the bolus calculator without help from their HCP, e.g., without implementation of the HCP set up methods. The disclosed systems and methods further provide a bolus calculator tool that can be implemented through software, e.g., such as a feature in a dedicated continuous glucose monitoring application, although the same can also operate as an independent application that integrates with a dedicated CGM application. In one exemplary implementation, it has been found useful to operate the bolus calculator as functionality provided as part of a CGM app. The bolus calculator tool is generally informed by CGM trend parameters so as to calculate and determine an insulin bolus.

In this regard it is noted that it is generally safer for patients to make dosing decisions on CGM with the help of a bolus calculator that takes into account trend information, such as may be available via CGM. The challenge is making safe bolus calculators available to patients, as now the same are generally limited to pump users, and none include trend adjustments. Doctors have only a few minutes during appointments to access a website and handle an unlocking mechanism, so the same may choose not to enable patients' bolus calculators at all if the setup process is too difficult. Currently there are many poorly done, error prone through lack of software validation, non-FDA-approved bolus calculator apps available that a patient may choose, instead of safe, but difficult to access, properly-configured bolus calculators.

As will be further described below, specific implementations of the systems and methods according to present principles also allow for secure handling of configurations/parameters/settings files for the bolus calculator. In addition, specific implementations also provide ways to integrate a bolus calculator app or functionality with third-party applications, e.g., such that the bolus calculator functionality is further informed by data received by third-party applications.

In the discussion below of HCP set up of bolus calculator/drug delivery parameters, it is noted that an HCP could attempt to manually enter the parameters onto the user's device, e.g., smart phone. However, such non-automatic data entry is fraught with concerns, including HCP liability, the extremely limited time an HCP generally has with the patient, as well as the lack of data measured by a CGM during the short time the HCP has with the patient, this last aspect leading to the result that the HCP generally has no information on which to base a suggested set of parameters. Multiple technological barriers thus prevent HCP manual entry, and thus give rise to the importance of automatic ways of transferring HCP knowledge into a user's bolus calculator and/or drug delivery system, such automatic ways incurring other needs, including security and privacy. Such incurred other needs also give rise to new potential efficiencies in the system, including the use of cloud servers in communication with HCP portals, the cloud servers also in communication with apps on patient devices.

Figure 4:
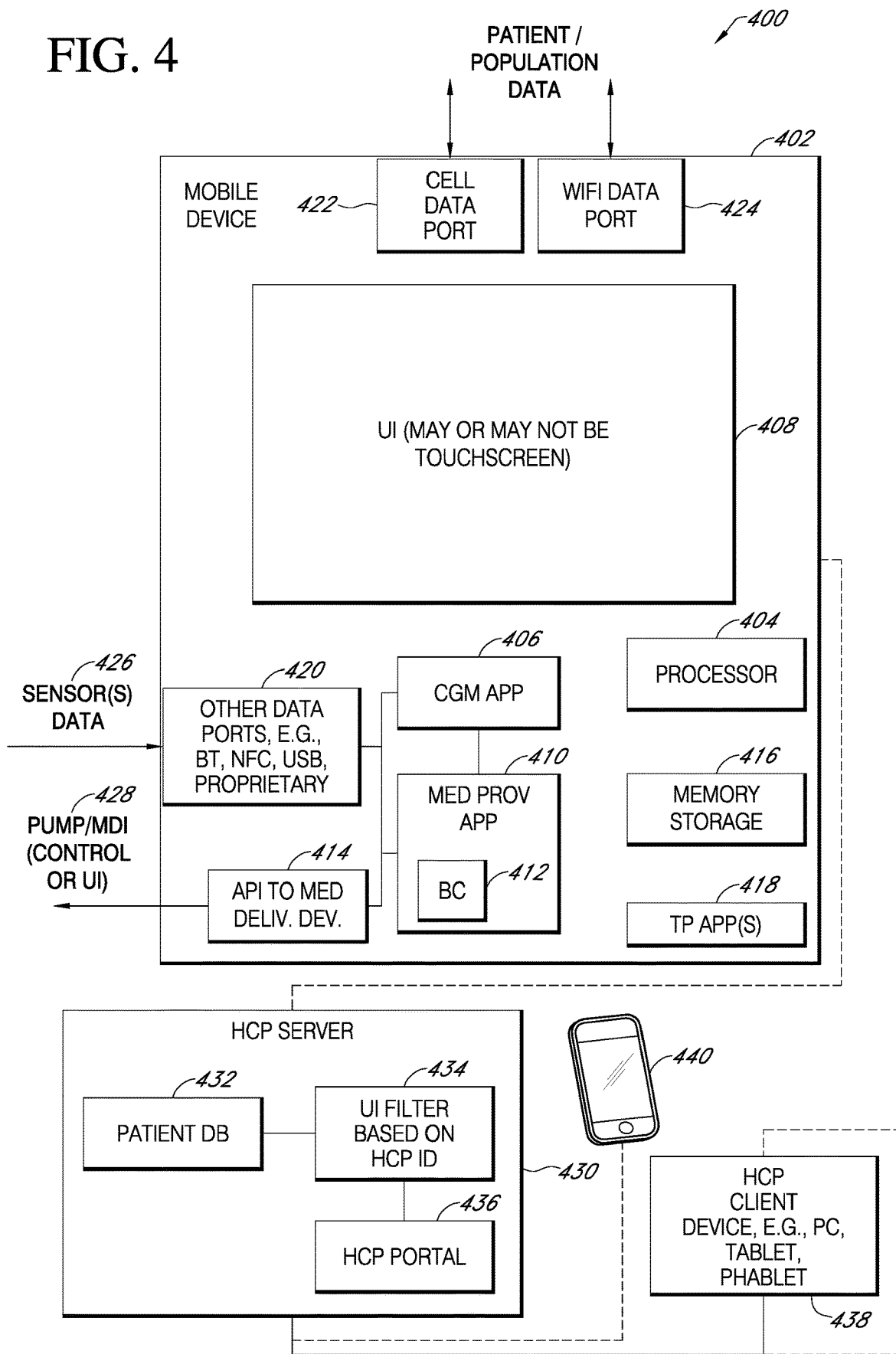
FIG. 4 illustrates more detailed aspects of an example system that may be used in connection with implementing embodiments of the disclosure.

FIG. 4 schematically illustrates a system 400 for accomplishing present principles, in one implementation. A mobile device 402 is illustrated, the mobile device in many cases being a smart phone of a user/patient, but which may also be a dedicated device. The mobile device 402 includes a processor 404, the processor for providing calculation and analysis aspects. A CGM application 406 is situated within the mobile device 402, the same generally being downloadable from a server, e.g., the Android or Apple App Store, and the CGM app 406 is generally instantiated by instructions residing on non-transitory media within the mobile device 402. For example, flash memory or other storage devices 416 may be employed, and the CGM app loaded into RAM memory at runtime. A medicament provision app 410 is also shown, and the same may include (or may be embodied by) a bolus calculator 412. The medicament provision app uses data from the CGM app 406 as well as other data (described below) to provide bolus calculator functionality, as well as, in some implementations, to provide signals to drive a pump or other medicament delivery device 428. The signals may be provided through an API 414, and the signals may be sent to a pump or other medicament delivery device including an MDI device, e.g., an insulin pen.

The CGM app could be part of the medicament provision app, or vice versa, or the same apps may be separate but communicate by a suitable API.

Data may be received from one or more third-party apps 418 (such as may be measured by sensors and stored and/or processed by the third-party app), and the same loaded into memory for processing by the processor 404 as part of bolus calculator or drug delivery calculations. Such third-party apps may include those tracking nutrition, fitness, activity, sleep, meals, heart rate, stress or the like. Accordingly, such apps may receive data from sensors including heart rate sensors, skin conductivity sensors, user input devices including cameras and keyboards/touchscreens, accelerometers, location tracking sensors including GPS, geolocation devices and apps, and the like.

Besides through third-party apps, data may be received in the mobile device 402 through data ports 420, which may serve as an entry port for data from sensors 426 (or for non-sensor data). Data ports 420 include one or more ports for receiving signals by Bluetooth®, near field communications (NFC), USB, as well as through proprietary interfaces.

The mobile device 402 may include a display 408, which can serve as a user interface where the same is embodied by a touchscreen. Data may be received in the mobile device 402 by the ports 420 described below, as well as from (and to) a cellular data port 422 and/or a Wi-Fi data port 424.

The mobile device 402 communicates with an HCP server 430, which may also be a cloud-based server to which the HCP also connects, e.g., by an HCP user account session. The HCP server 430 generally includes a patient database 432, and an HCP portal 436. The HCP portal 436 can access the patient database 432 and may further securely receive a list of patients by way of a filter 434 based on the HCP identification. Other aspects of HCP identification and filtering are described below. One or more HCP client devices may access the HCP server 430 through the HCP portal 436. Two HCP client devices are shown in FIG. 4: an HCP client device 438 such as a PC, tablet, phablet, or the like, as well as an HCP mobile device 440.

In one system and method according to present principles, an application may be configured to execute on the user mobile device. The application may include a first input configured to receive signal data from a continuous indwelling analyte sensor and transmitter. A second input may also be employed, which is configured to receive signal data corresponding to subject patient data and/or patient population data. The application may also include instructions configured to employ the first and second inputs to calculate a bolus value, where the second input is employed to provide settings and/or parameters for a bolus calculator, and where the first input is employed to provide current patient analyte concentration values to be applied to a function at least in part determined by the settings and/or parameters to calculate the bolus value.

The third party apps may have their own inputs, and the application may further include instructions for receiving the signal data from the continuous indwelling analyte sensor and for calculating and displaying a clinical value of the analyte concentration, e.g., via various calibration routines. The instructions may be further configured to transmit the calculated bolus value to a medicament delivery device.

Systems and methods according to present principles also contemplate an application configured to execute on a server. This server application may include first instructions configured to receive data about a subject user and to set up a subject user account. A first input may be configured to receive sensor data from a device associated with a subject user. Second instructions may be employed, which are configured to analyze data from the first input and determine if bolus calculator parameters and/or settings on the subject user device are optimal, e.g., by determining if a bolus calculator meter/setting change triggering event has occurred. If the settings are not optimal, one or more of the instructions, e.g., the third instructions, may be configured to transmit a signal to a health care practitioner portal associated with the server, or to the subject user device, to cause a modification of the parameters and/or settings.

Figure 5:
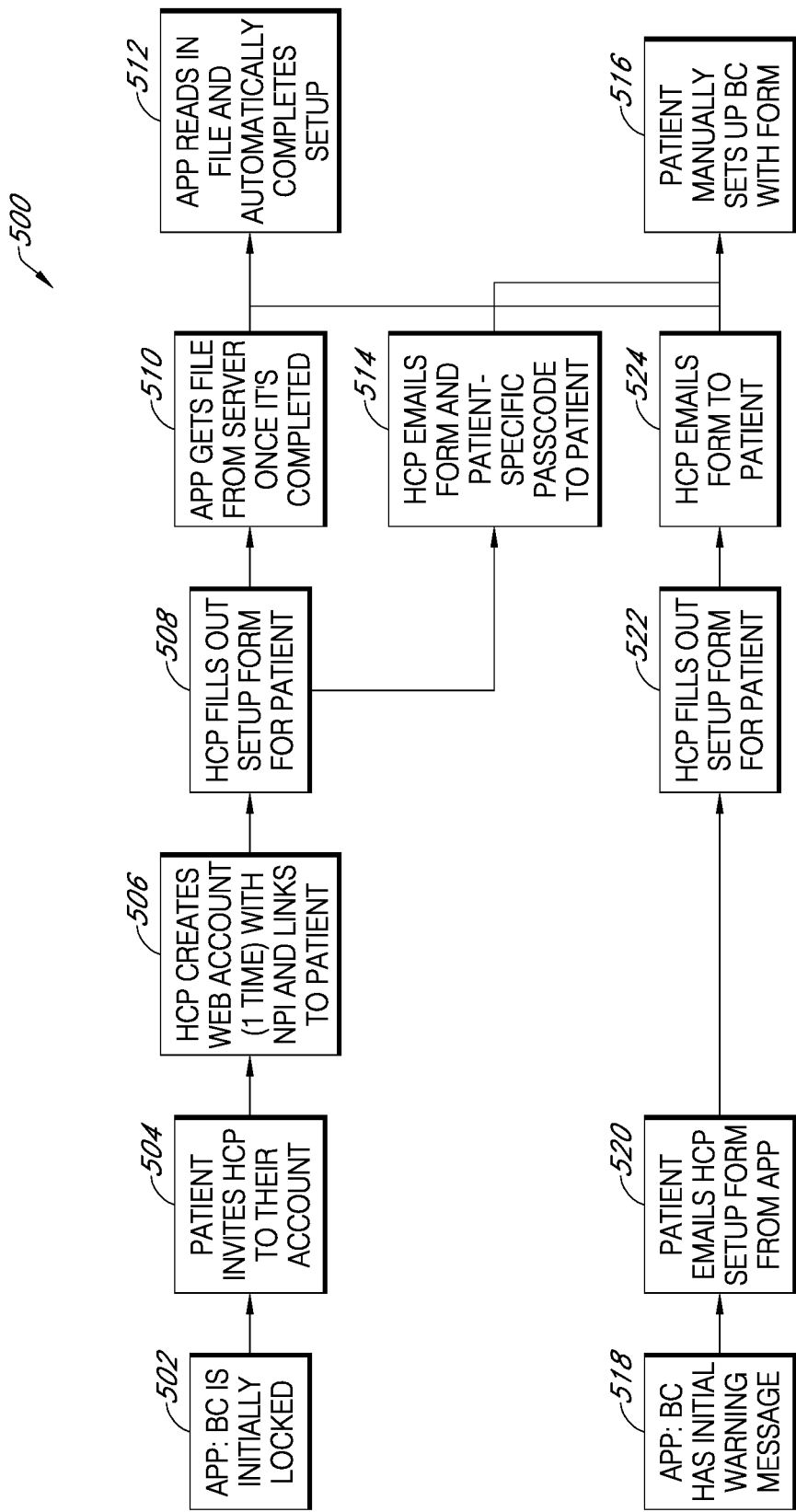
FIG. 5 illustrates a flowchart of an implementation of a method according to present principles.

FIG. 5 illustrates a flowchart 500 of a first implementation of a system and method for at least partially involving an HCP in the set up of a bolus calculator of a user. A particular advantage of the method of FIG. 5 is that the HCP need not have any knowledge about the particularities of a specific user device.

In a first step the bolus calculator is initially locked by the application (step 502). A patient may then invite the HCP to their account (step 504). Such an invitation may be sent through the cloud server noted above. The HCP then creates an account with the cloud server, if one has not already been created, e.g., a web account, and the same is linked to the patient (step 506). Generally the HCP need only create one web account and the same may be linked to a number of patients.

These steps provide strict enforcement that the HCP must be involved in the setup. Such is a particularly safe implementation, but causes a greater burden on the HCP and may be frustrating for users who may have already been trained on the setup of a bolus calculator.

Once both the patient and the HCP are connected through the cloud server, the HCP may fill out a form for the patient, the form including settings/parameters about the bolus calculator (step 508). The bolus calculator app receives the file from the cloud server once the form is completed and a file created with the appropriate parameters from the form (step 510). Alternatively, the HCP may email the form to the patient (step 514). For example, the parameters may be stored in the form, and the data file with the form information protected with a passcode. Upon entry of the passcode, the patient may access the parameters, open the bolus calculator app, and manually set up the bolus calculator app with the data from the form (step 516). Alternatively, the app may read in the file and automatically complete the bolus calculator set up (step 512). In this latter way, in which the bolus calculator app is unlocked upon receipt of the parameters from the HCP, set up is made easier and transcription errors eliminated. However, the patient may lose the potential training of manual set up, and the same may, in some cases, pose a higher cyber security risk.

In a different implementation, the app may not be locked, but the bolus calculator may provide an initial warning message to the patient of the dangers of bolus calculator set up without HCP involvement (step 518). In this method, the patient may email their HCP a setup form, which may be transmitted in some cases from the app itself (step 520). The HCP then fills out the setup form for the patient (step 522), and the HCP transmits the form back to the patient (step 524). As before, the patient then manually sets up their bolus calculator using the data from the form (step 516). Variations from other embodiments may also be seen here, including where set up parameters are automatically entered into a bolus calculator app (or suitably configured functionality within a CGM app).

Variations will be understood, and the variations may provide simpler or more complicated set up options.

Figure 6A:
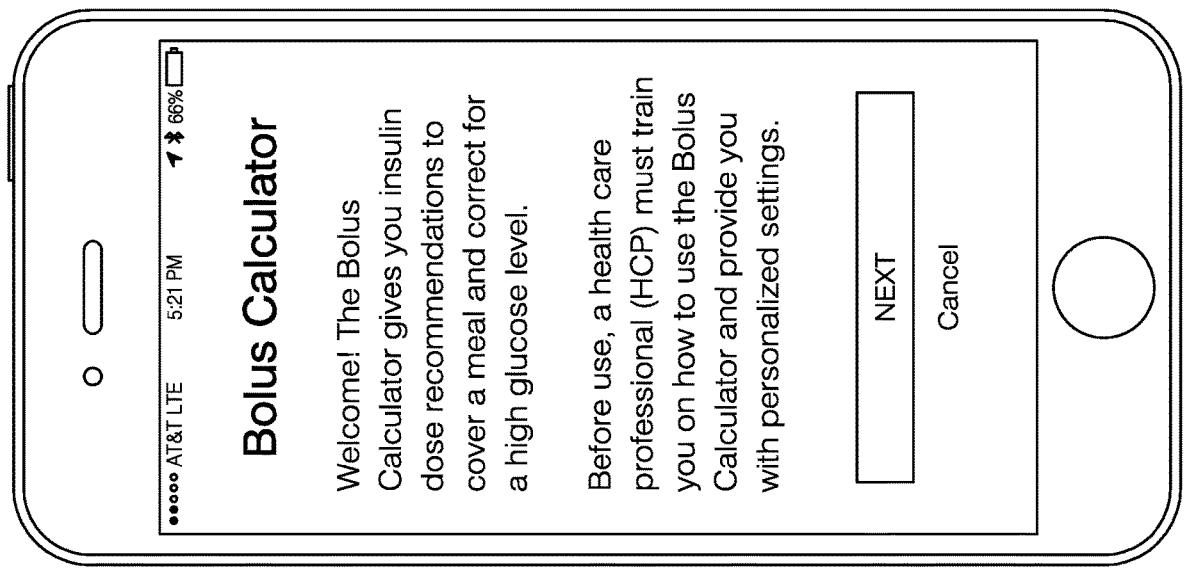
FIGS. 6A-6C illustrate steps according to present principles in which a bolus calculator application may be unlocked.
Figure 6B:
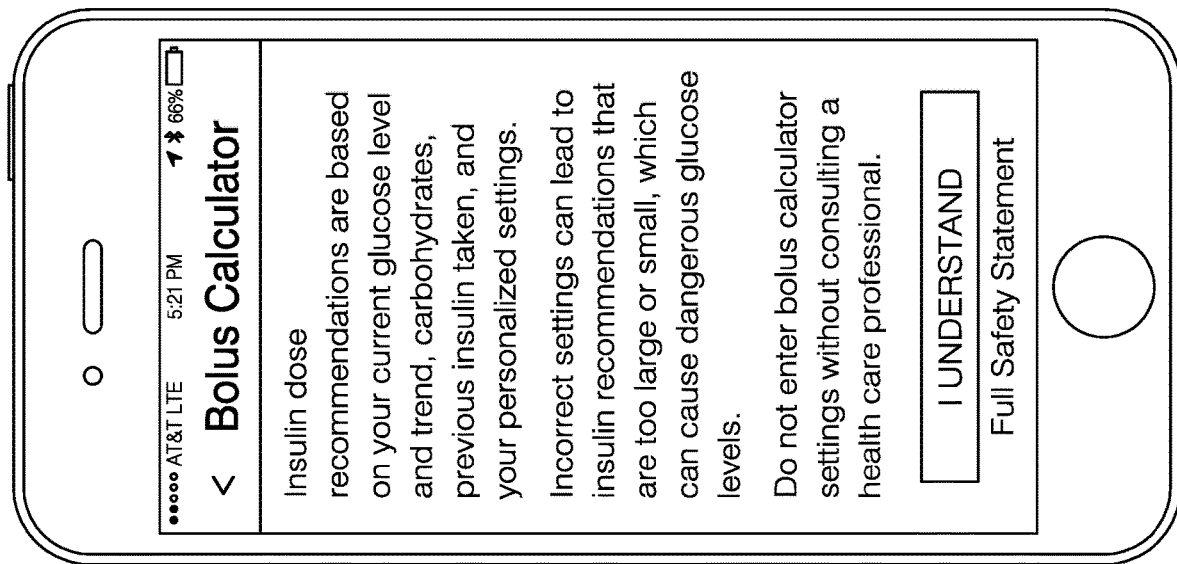
Figure 6C:
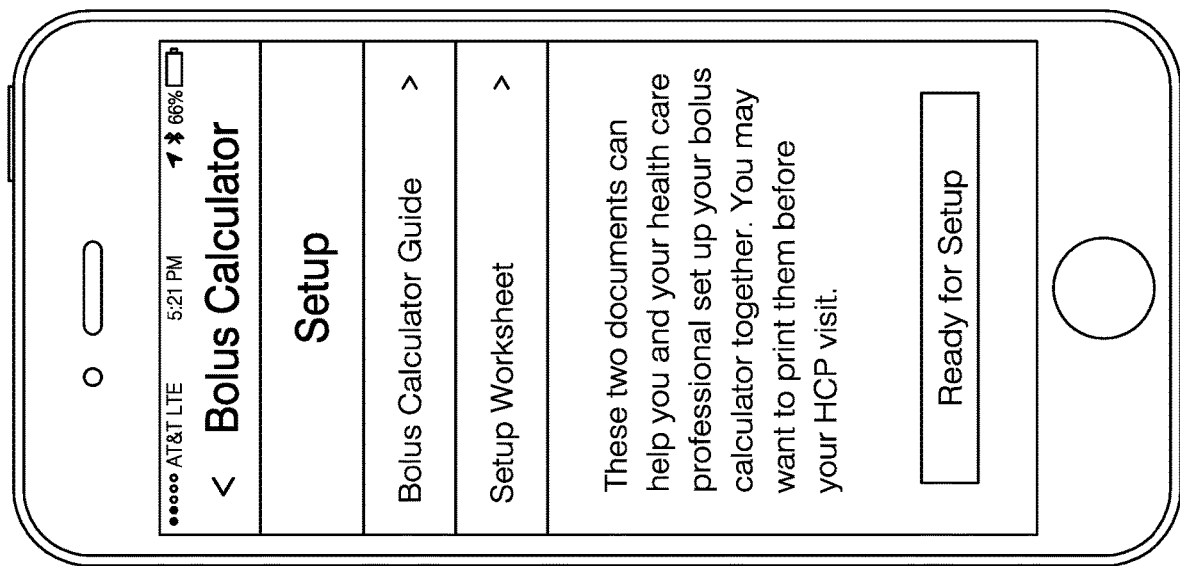

For example, and referring to FIGS. 6A-6C, for a particularly simple set up method without an unlocking step, a user may, on their app, open a bolus calculator menu. The bolus calculator menu may inform the user that it is unsafe to set up their bolus calculator without help from their HCP. The user may then click that they understand, and access may be granted to the app. The system may display a screen that shows a clinician website location, where the same further includes a set up worksheet and a user guide. The user may be advised to printout a worksheet for their next HCP visit. The user may even be provided with an activatable button that states "ready to set up bolus calculator". Similarly, the HCP may provide a website that describes the bolus calculator and contains set up information, e.g., a set up worksheet and set up instructions. Back on the app, the user may click "ready to set up bolus calculator". The user may see an additional confirmation screen asking them to confirm that they have worked with an HCP to get set up parameters. Upon clicking "I understand", the user may enter a setup wizard for the bolus calculator, and may transcribe settings from their worksheet.

As another example, for a simple unlocking method, on the app, a user may open a bolus calculator menu and view a message that it is unsafe to set up and use a bolus calculator without assistance from an HCP. However, a field may be provided for an HCP to enter an unlock code. On a website, the HCP, knowing their patient is setting up a bolus calculator, may enter in desired data to set up a new patient. The HCP may enter their own name and national provider identifier (NPI) number. The server may check that the NPI number has the correct number of digits (e.g., 10) and is all numbers (and may perform other checks). The HCP may be required to click a legal statement saying a certification such as "I certify that I am a healthcare professional authorized to provide health care services to patients." Upon submission of the certification, the HCP may be taken to a page that has a set up worksheet and user instructions, and may be told to print the set up worksheet. The HCP can click a button to get a unique, single use, unlock code for the patient and there may be a location to write the code on the set up worksheet.

On the app, the user or HCP enters the single use unlock code, and waits for server confirmation of validity. Upon determining that the code is valid, the user/HCP enters the setup wizard for the bolus calculator and can transcribe settings from the HCP provided worksheet.

In the above system and method, novice users are deterred from unsafely setting up bolus calculator parameters without help from an HCP. If the user actively pursues set up, then they are making an informed decision to use the CGM bolus calculator unsafely. As the individual CGM user still has to enter their own set up parameters manually, they could not be fooled by someone pretending to be a doctor; they would need to be pretending to be a doctor themselves.

A number of more detailed methods of providing HCP set up are now described.

Referring to FIGS. 7A-7E, HCP setup of a bolus calculator is described, the bolus calculator provided as part of a CGM app. In this implementation, an HCP request access to a patient's account, and the HCP obtains a user ID from the patient. A form with set up parameters is filled out online and is digitally sent to the patient. In summary, an HCP sets up an account for a bolus calculator, where such access and set up generally requires authentication such as an NPI code and/or a secondary confirmation. The HCP requests access to the user account. If the patient accepts HCP permission request, the HCP sets up the appropriate parameters. The HCP confirms the parameters and the patient information and sends the file with the parameters to the CGM app. The patient and the CGM app receive the update, and accept the parameters in the GCM app.

In more detail, a physician may begin the process at a login/sign-up screen (step 701). If the user is not an HCP, then they generally cannot perform this step, and thus a message may be displayed indicating they cannot continue (step 702). In response to the sign-up query (step 703), if the HCP indicates that they have not already signed up, they may be prompted to enter their NPI code (step 704), and may further undergo a secondary confirmation of various type (step 705). If they have proven that they are an HCP, (step 706), then they may continue to the creation of a user name (step 707) and password (step 708). If not, a message may be displayed indicating that they cannot continue (step 702).

If the HCP continues, the same may be prompted to enter their email (step 709), and may begin setting up a bolus calculator for a new patient (step 710). Where the HCP has already signed up, they may simply enter their login credentials (step 711).

The system and method according to present principles may then prompt the HCP to indicate if they are setting up a bolus calculator for a new patient (step 710). If yes, the HCP may move on to an "adding new patients" branch. If not, the system may display patients already added (step 712), and the HCP may be prompted as to whether they wish to view settings for patients already added, e.g., who may already have bolus calculators enabled (step 713). In this case, the HCP may select a patient (step 714).

The HCP may be prompted for, or the system may simply indicate, if the patient has a bolus calculator enabled or otherwise set up (step 715). If yes, the patient's bolus calculator settings may be displayed (step 716), and if necessary missing settings may be highlighted. The HCP may choose to edit settings (step 717), and if so desired, the parameters may in some cases be edited. The editing may occur within "guard rails" (step 718). For example, limits or ranges may be set for what the HCP can enter as parameters. Such "guardrails" may be determined based on a patient's weight, history, age, BMI, and so on.

Such parameters may be confirmed by the HCP prior to sending to the patient (step 719). If the HCP does not confirm the edited parameters, the HCP may re-edit the same (step 718). Once the HCP does confirm the parameters, then the HCP may be notified that the updated settings will be sent to the patient (step 720). In this case the patient bolus calculator settings may be displayed, along with an indication that the system is "WAITING FOR PATIENT" to accept changes (step 721).

The patient may then select whether to accept the changes (step 722). If yes, the edited bolus calculator settings may be displayed to the HCP (step 716). If the patient does not accept the changes, then the patient may be asked if proposed changes to the edited parameters are desired (step 723). If the patient does not send back proposed changes, then the HCP may be notified that the patient denied the changes and did not send proposed changes (step 724). Again the process may resume at step 716, with the display of the patient bolus calculator (unchanged) setting.

However, if the patient does send back proposed changes, then the HCP may be notified that the patient denied the changes and sent back proposed changes (step 726). The HCP may be prompted to approve the proposed changes (step 727). If the HCP does not accept the proposed changes, then the HCP may be presented with a screen to edit the parameters, e.g., within the guardrails (step 718). However, if the HCP approves the proposed changes, then a notification screen may be provided to the HCP that the approved settings will be updated in the patient's bolus calculator (step 728). The patient may be notified that their proposed changes were accepted and their bolus calculator updated (step 729).

Returning to step 710, if the HCP is setting up a bolus calculator for a new patient, then the HCP may be provided with a screen prompting whether a patient ID is needed (step 730). The HCP may be prompted as to whether they have the patient's ID (step 731). If not, the HCP may request the ID from the patient via, e.g., email, text, the CGM app, or other messaging service (step 732). Once the patient's ID is obtained, the HCP may enter the patient ID (step 733). Various information may be employed to correctly identify the patient, including their name and date of birth, and such may be displayed such that the HCP can confirm the patient identity (step 734), again so that settings can be confirmed to be for the correct patient.

The HCP may then be prompted as to whether the correct patient is displayed and identified (step 735). If, using the displayed information, the HCP determines that the correct patient has not been identified, the process may restart at step 730. If, however, the correct patient is identified, then the HCP may add the patient (step 736).

The HCP may be prompted as to whether the patient is a pump user (step 737). If yes, certain of the bolus calculator parameters may be pre-populated (step 738) based on pump bolus calculator settings. Again, missing settings may be highlighted for HCP input, and in this case the HCP may supply the missing settings or edit pre-populated settings (step 739). In this case, the HCP may be requested to confirm the sending of the settings to the patient (step 740). Where the HCP confirms that the settings can be sent, flow may proceed at step 720. If the HCP does not confirm that the settings can be sent to the patient, then the system may display pre-populated settings that can be edited (step 741). The HCP may be prompted to edit the pre-populated settings (step 742 and if they choose to do so, then the parameters may be edited, e.g., within the guardrails (step 718), and flow may proceed from step 718. If the HCP chooses to not edit the default settings in step 742, then flow may proceed at step 740.

Returning to step 737, if the patient is not a pump user, then the HCP may be prompted as to whether they wish to enable/set up the patient's bolus calculator (step 743). If they do not wish to do so at this time, flow may pass to a display of patients already added (step 712). If the HCP does wish to enable/set up the patient's bolus calculator in step 743, then flow may pass to the display of pre-populated settings that can be edited (step 741).

In all of these cases, values can be pre-populated to reduce the data entry burden and further to preselect a rationale, both the rationale and the settings capable of being sent to the user. The rationale may be employed to advise the user as to why the particular settings have been chosen for them.

In the above-described implementation, the HCP may be enabled to define safe ranges for the parameter values for individual patients, rather than device specific safety ranges, such values providing better bolus calculator settings than device based ones. Individual patient parameters may be set up, and the patient may moreover be trained to have the ability to modify these values later.

Certain advantages to the method of FIGS. 7A-7E include that only the HCP enters values, thus reducing or eliminating transcription errors. In addition, the HCP is generally always involved in the setup. Disadvantages include that the patient may not always be involved during the HCP conversation for bolus parameters. In addition, bolus values are available on the cloud, although various safety and security measures may be taken. In addition, there is a possibility that the HCP selects the incorrect patient, although this risk may be mitigated through use of identifying data such as name and date of birth as well as patient confirmation on the telephone.

In a particular use case, certain bolus calculator parameters/values, or ranges of such values, can be pre-approved for direct import. In a related implementation, values authorized to be used with the bolus calculator can be imported, with unauthorized values being rejected. Where the user has a pump that has already been set up, bolus calculator values from the pump can be imported. For example, values may be automatically imported into the HCP server when the HCP is setting up appropriate parameters. Fields that are missing may be highlighted for the HCP to enter manually. HCPs or users can optionally adjust parameters pertaining to trends independently. For example, the trends calculated need not necessarily be linked to the bolus calculator in the pump, but may rather be tied to trends measured and determined by a CGM app.

Figure 7A:
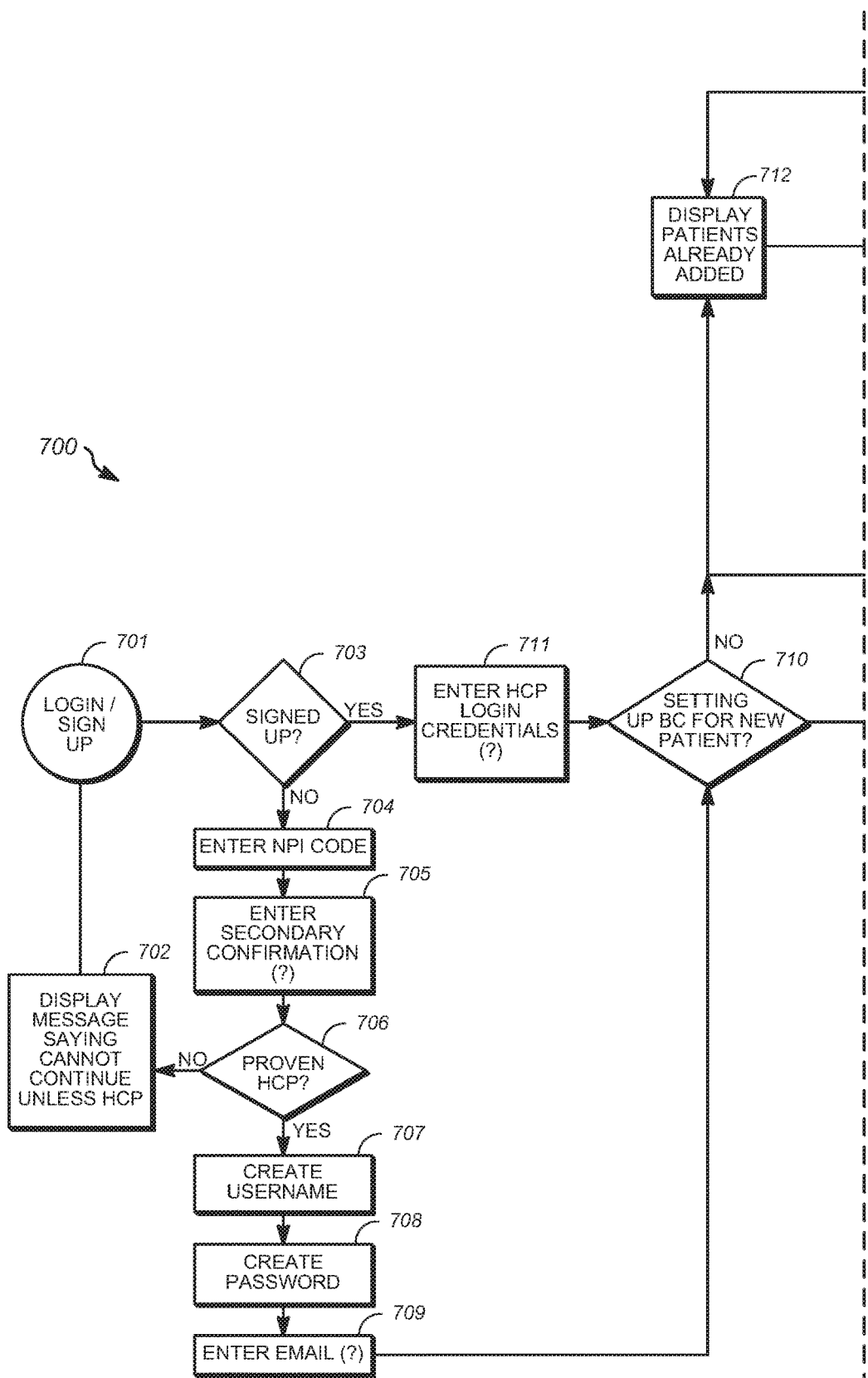
FIGS. 7A-7E illustrate a flowchart of another implementation of a method according to present principles.
Figure 7B:
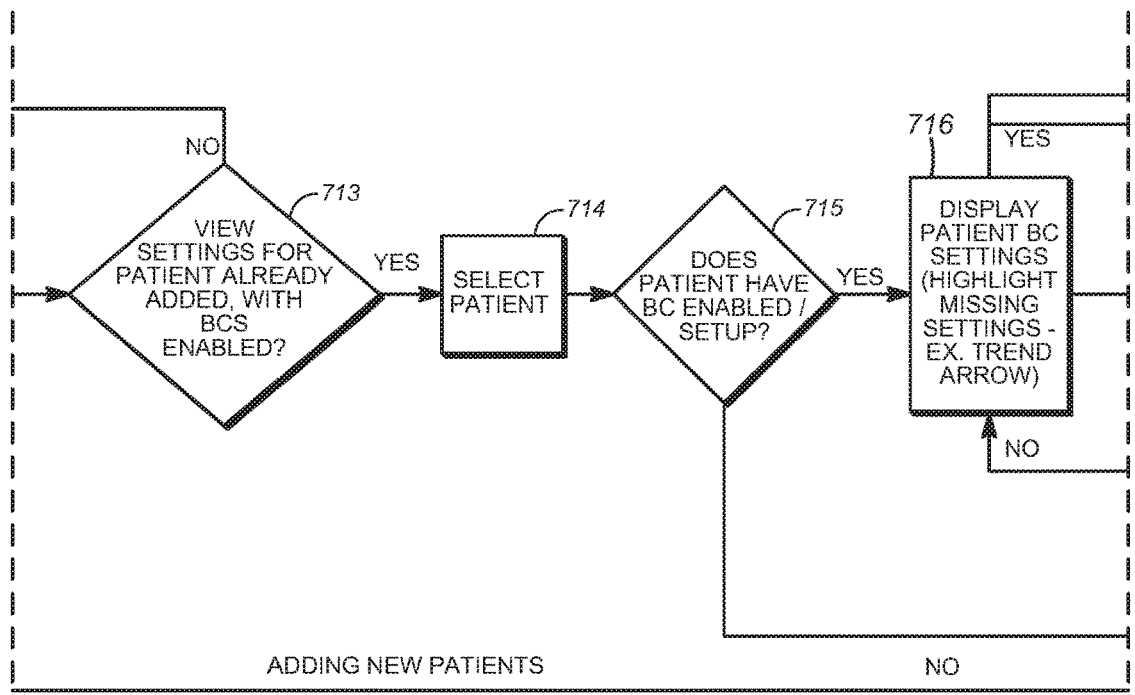
Figure 7B:
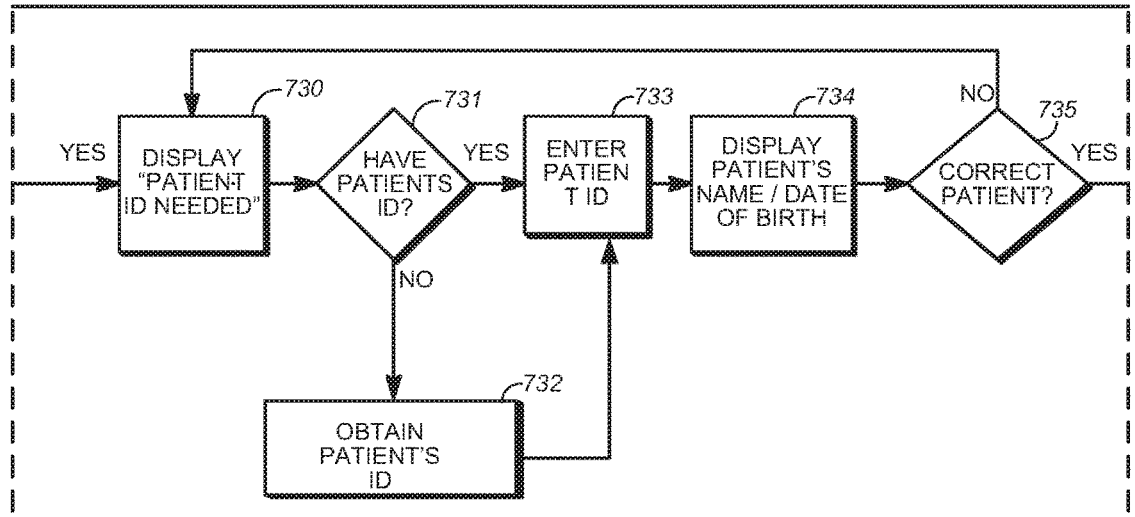
Figure 7C:
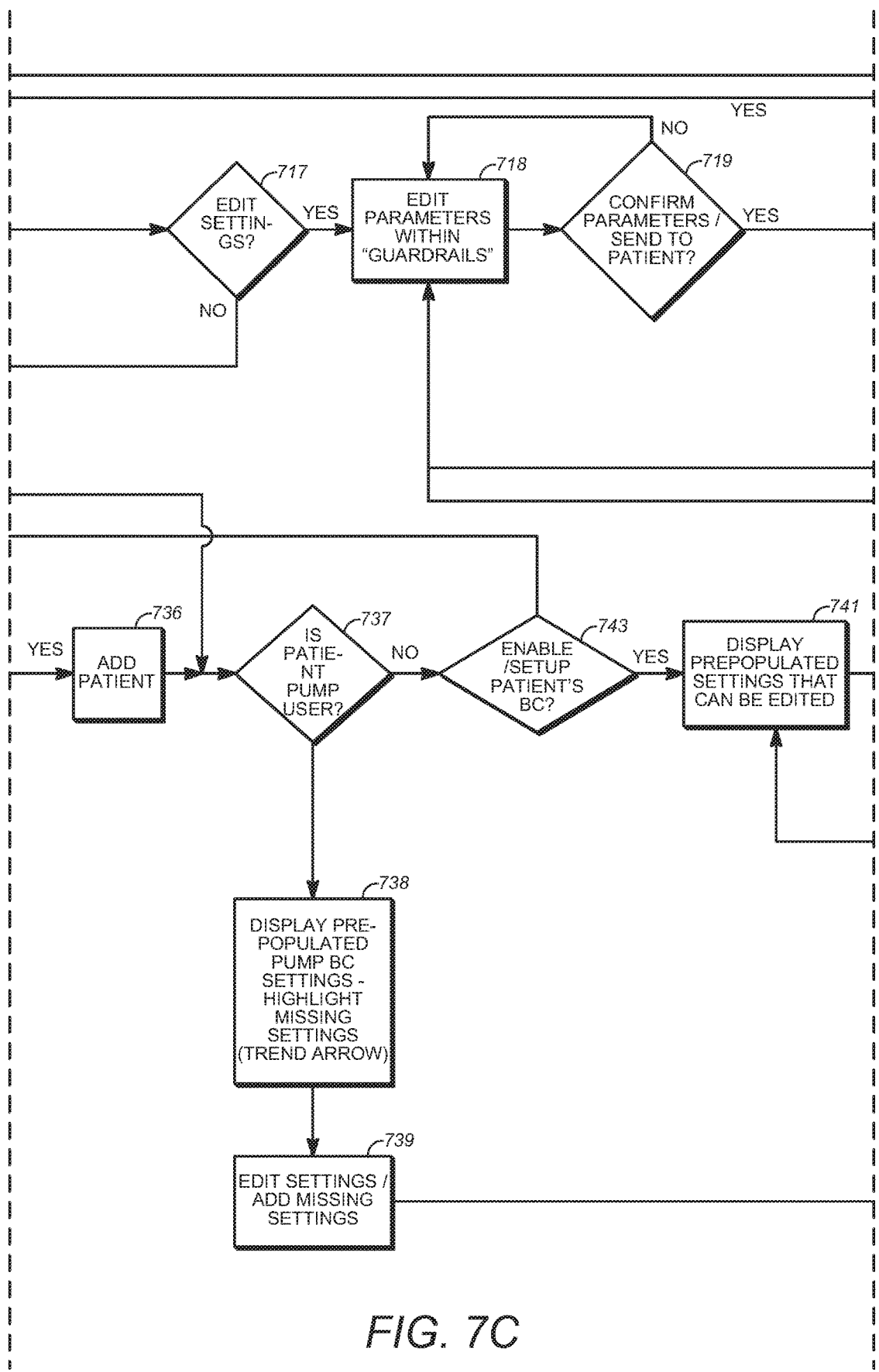
Figure 7D:
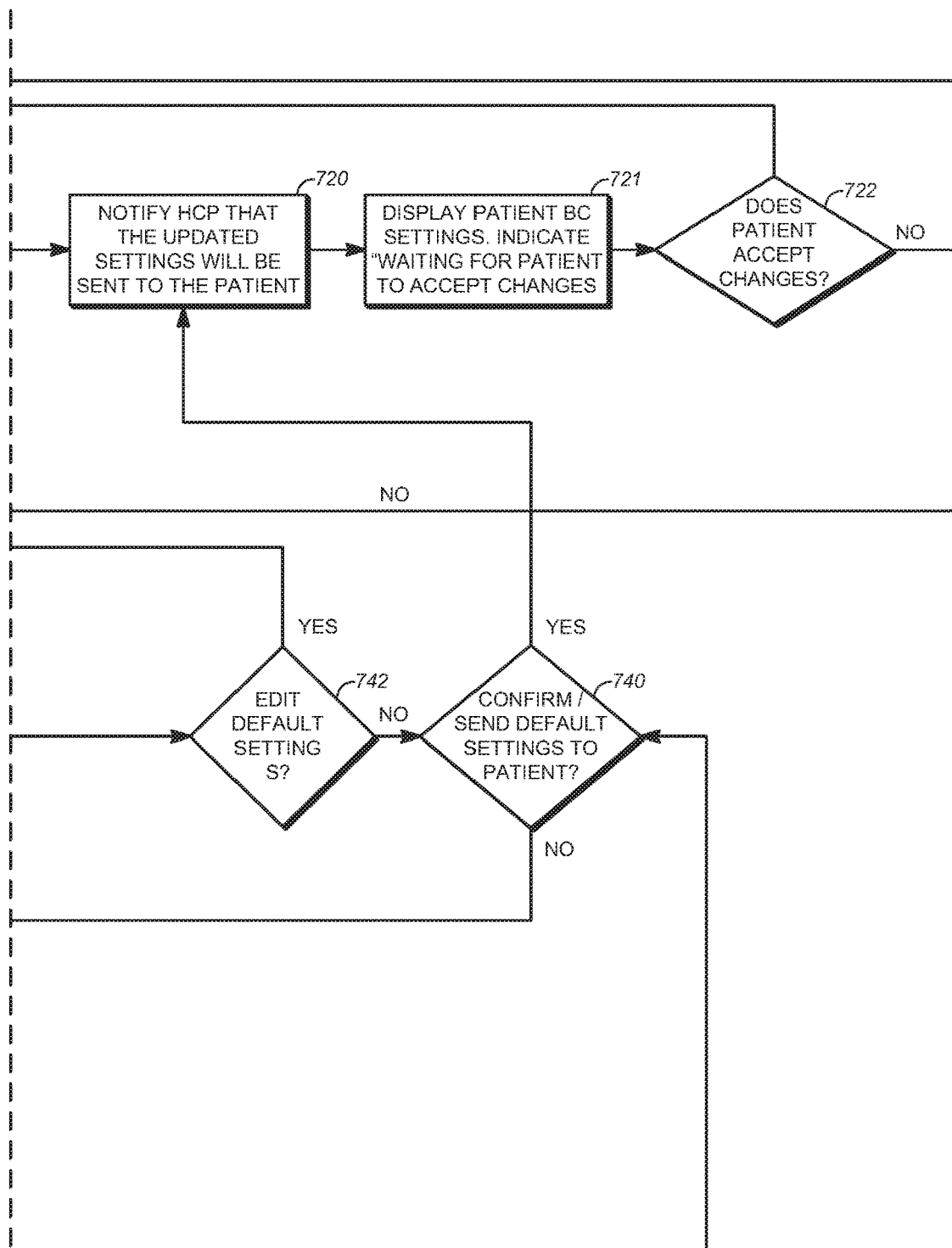
Figure 7E:
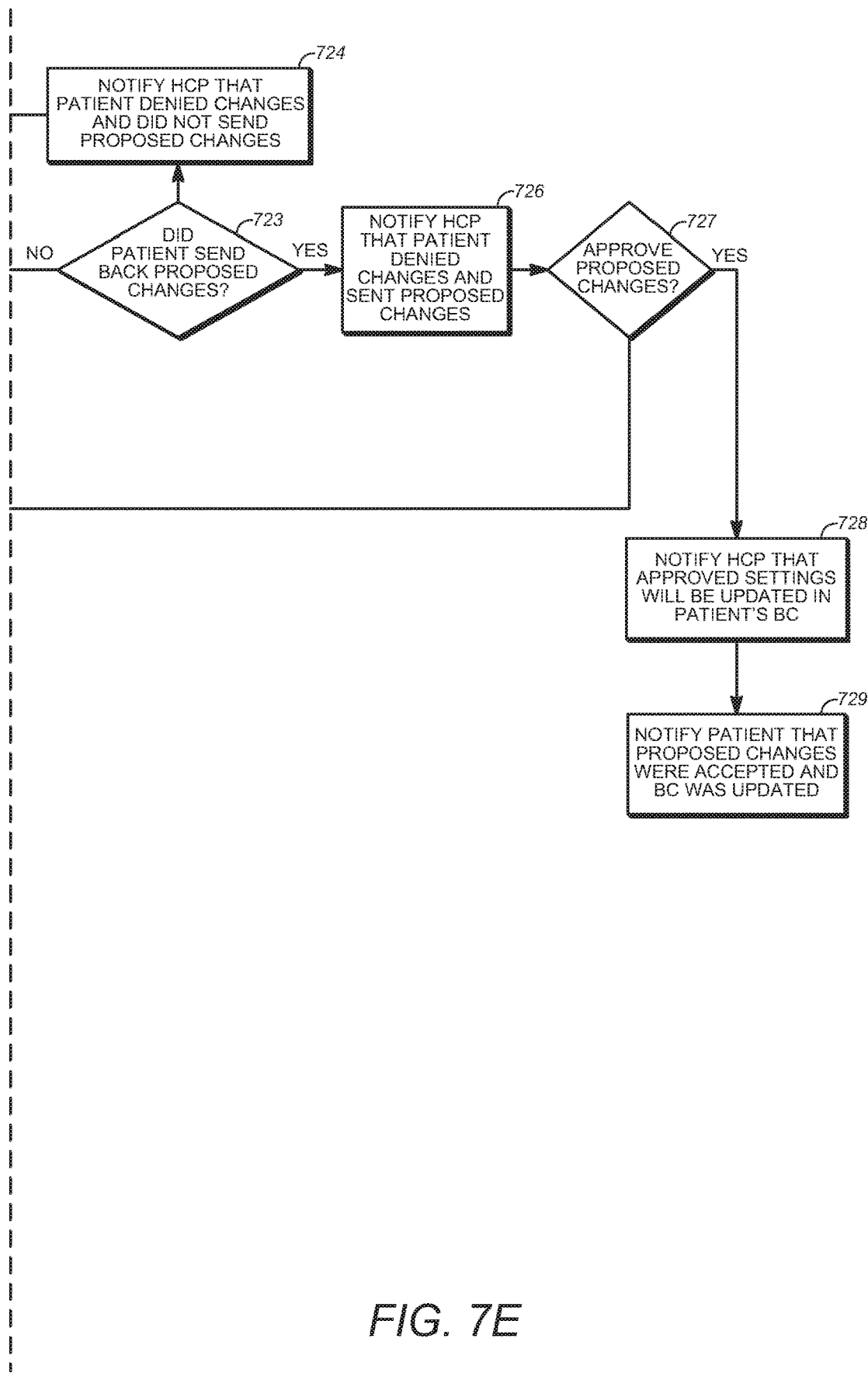
Figure 7F:
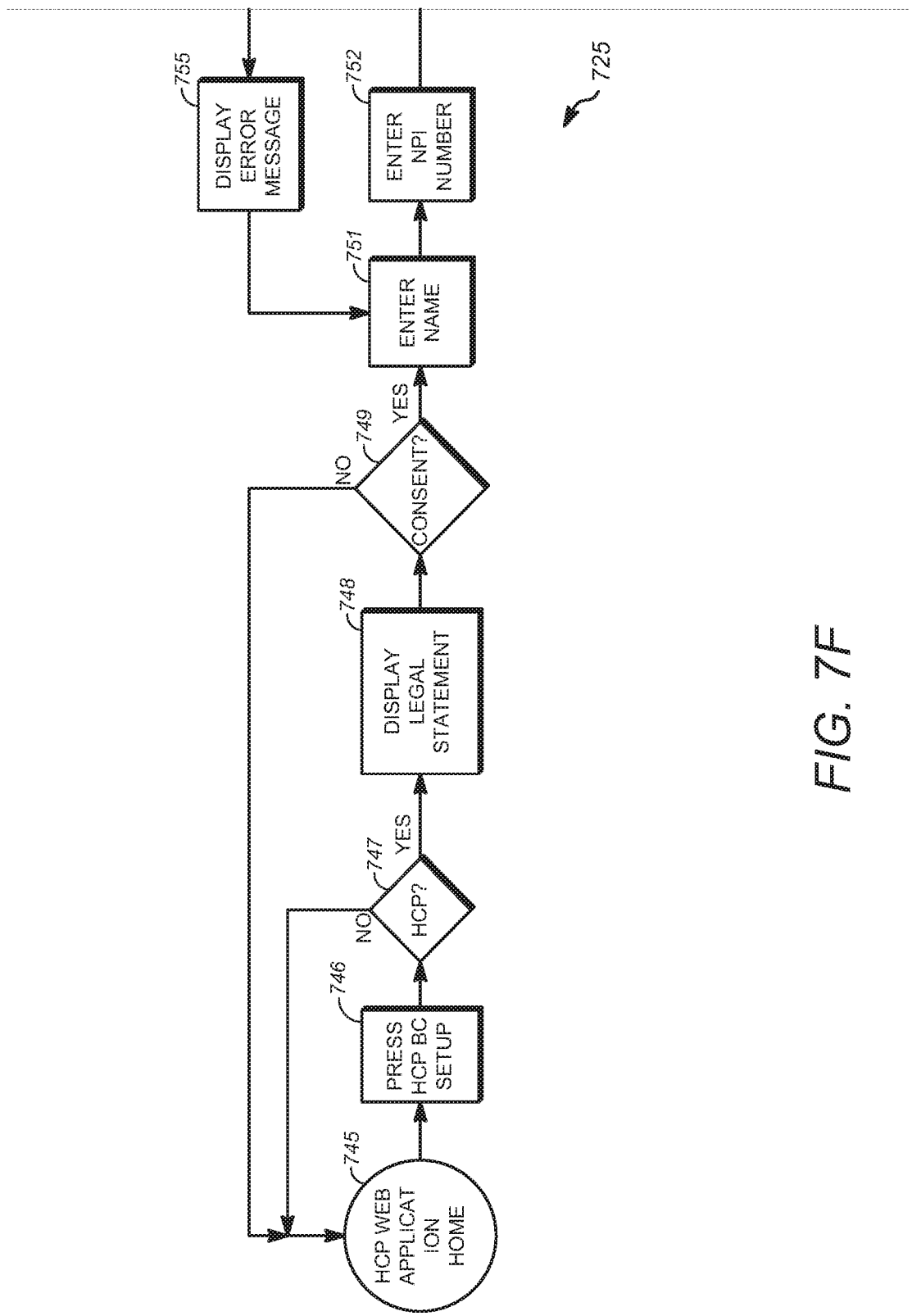
FIGS. 7F-7L illustrate a flowchart of another implementation of a method according to present principles.
Figure 7G:
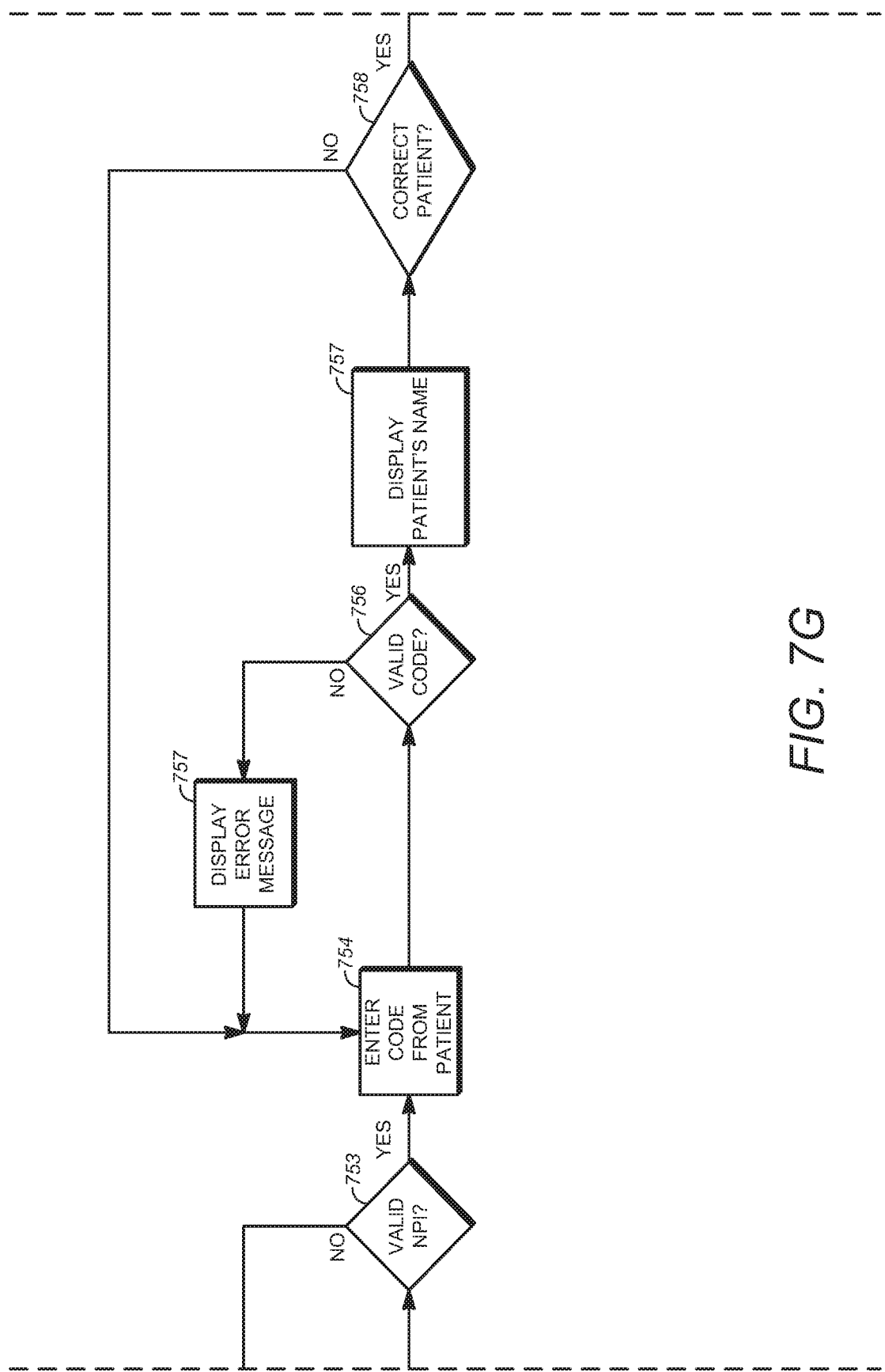
Figure 7H:
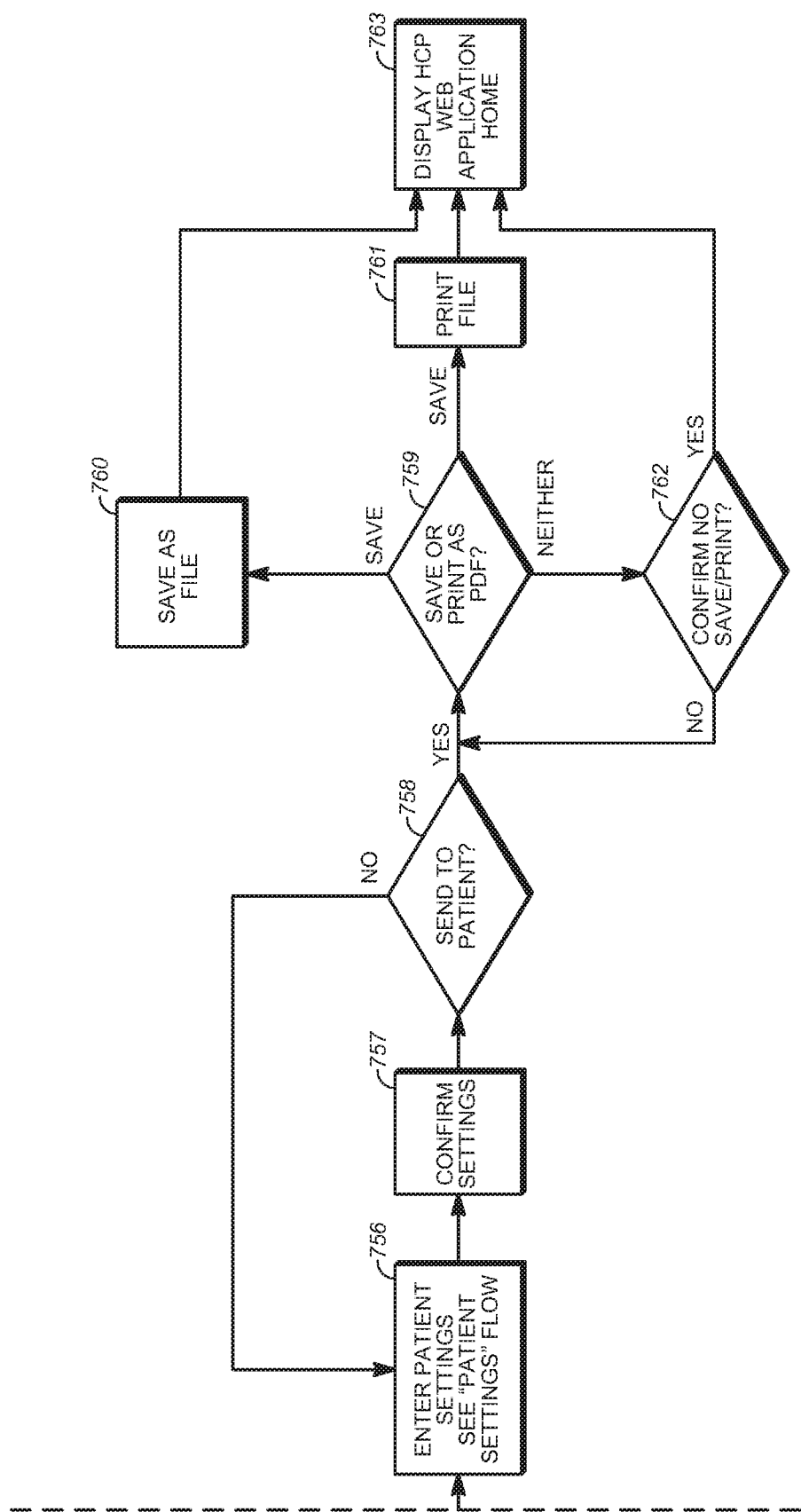
Figure 7I:
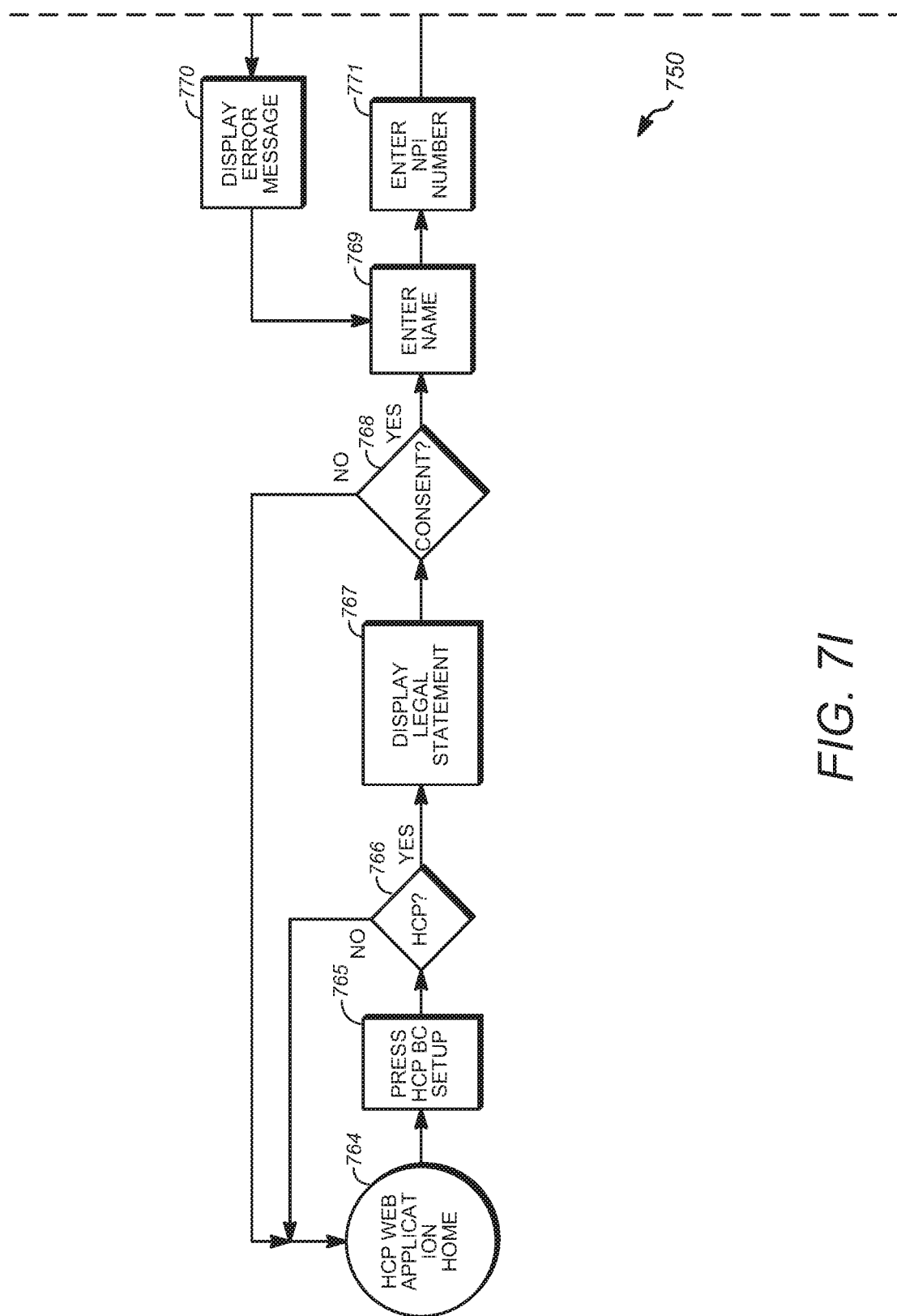
Figure 7J:
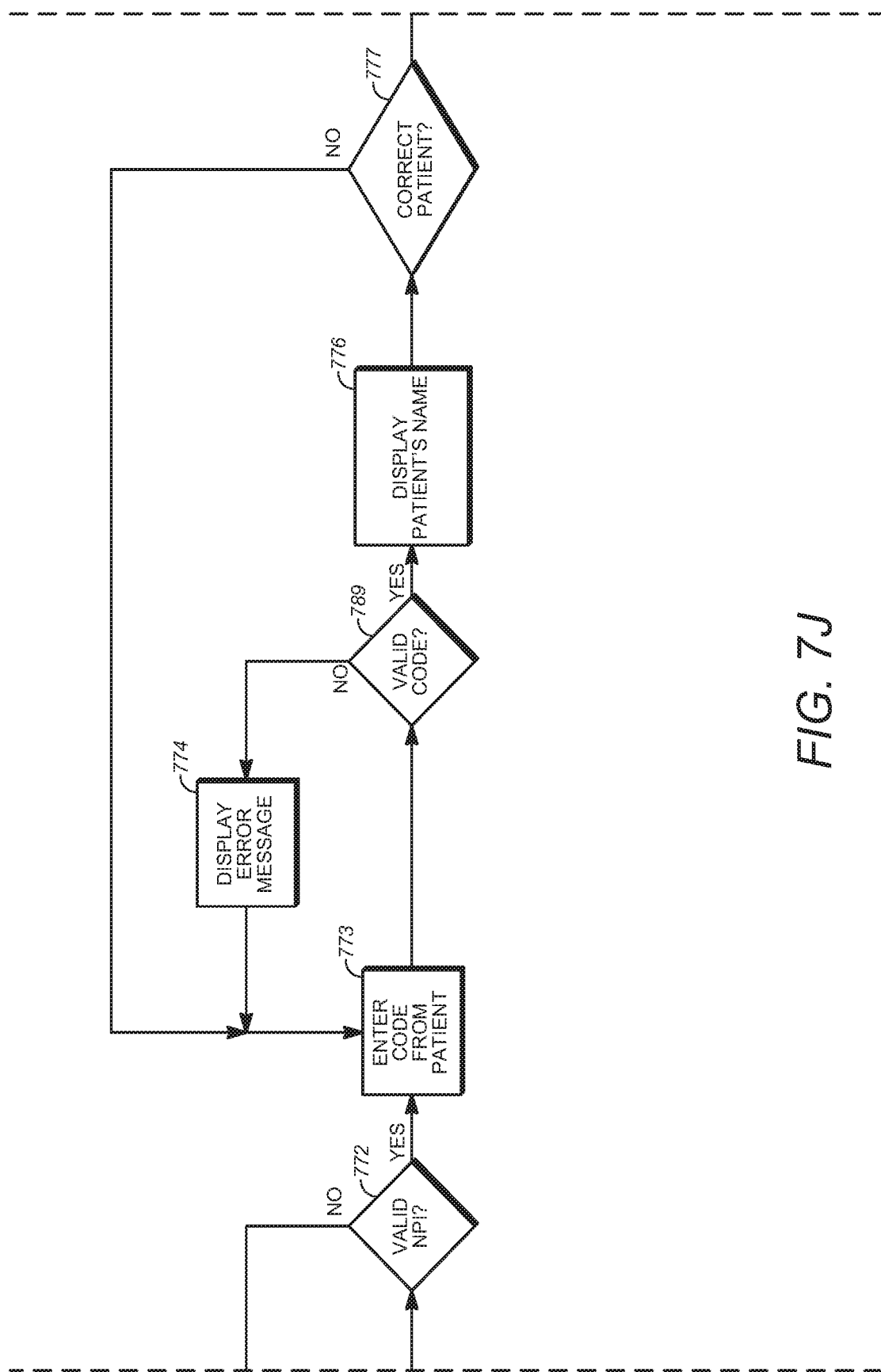
Figure 7K:
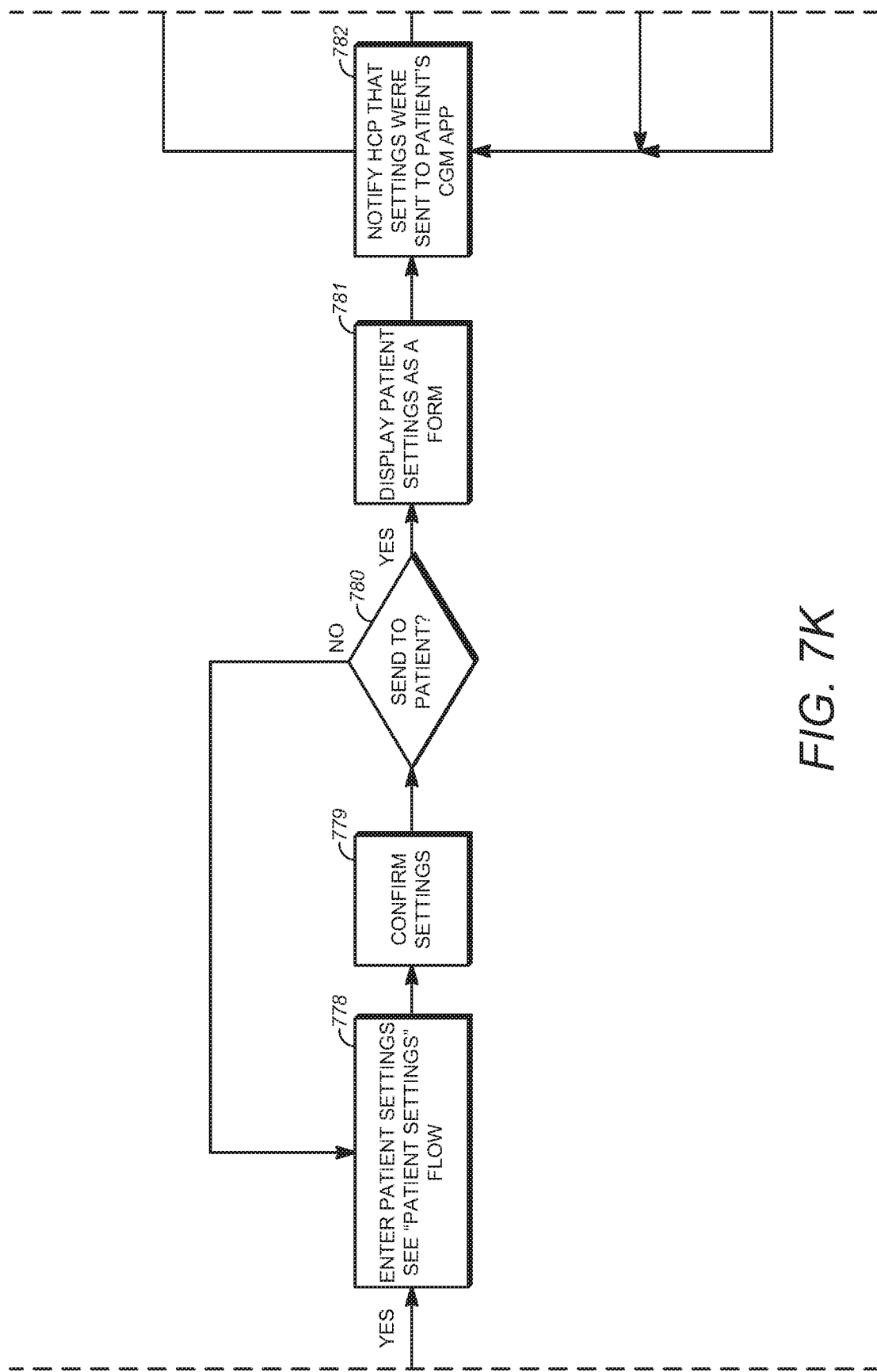
Figure 7L:
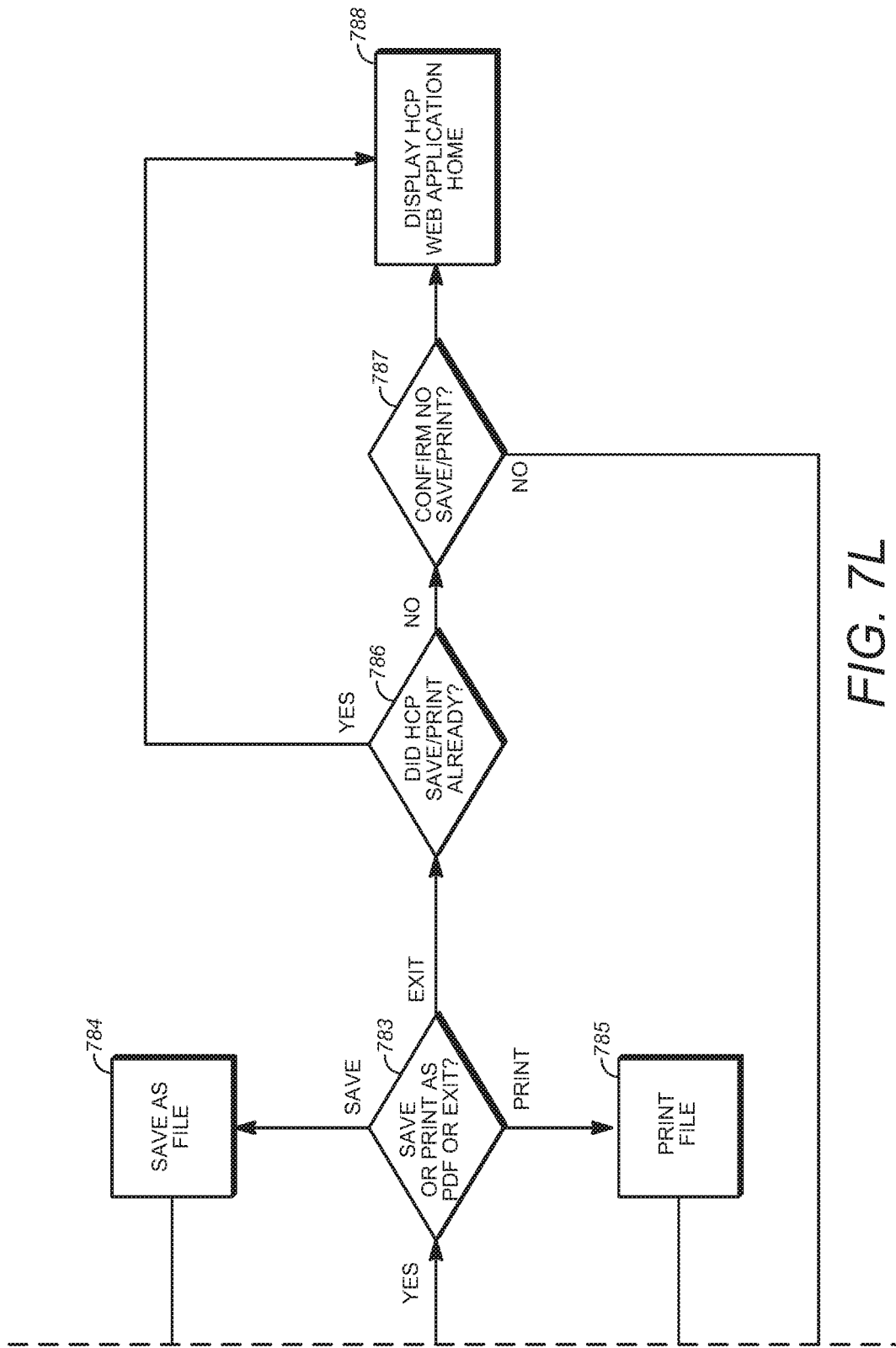
Figure 7M:
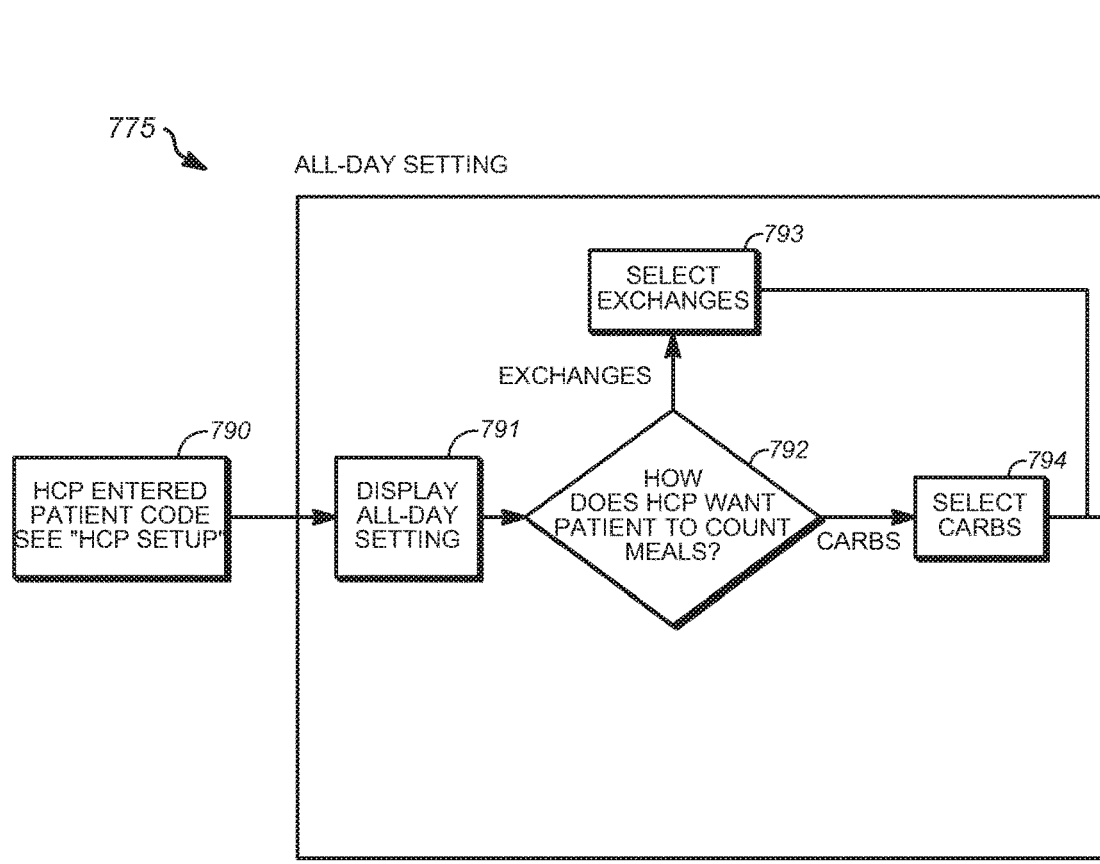
FIGS. 7M-7U illustrate a flowchart of another implementation of a method according to present principles.
Figure 7N:
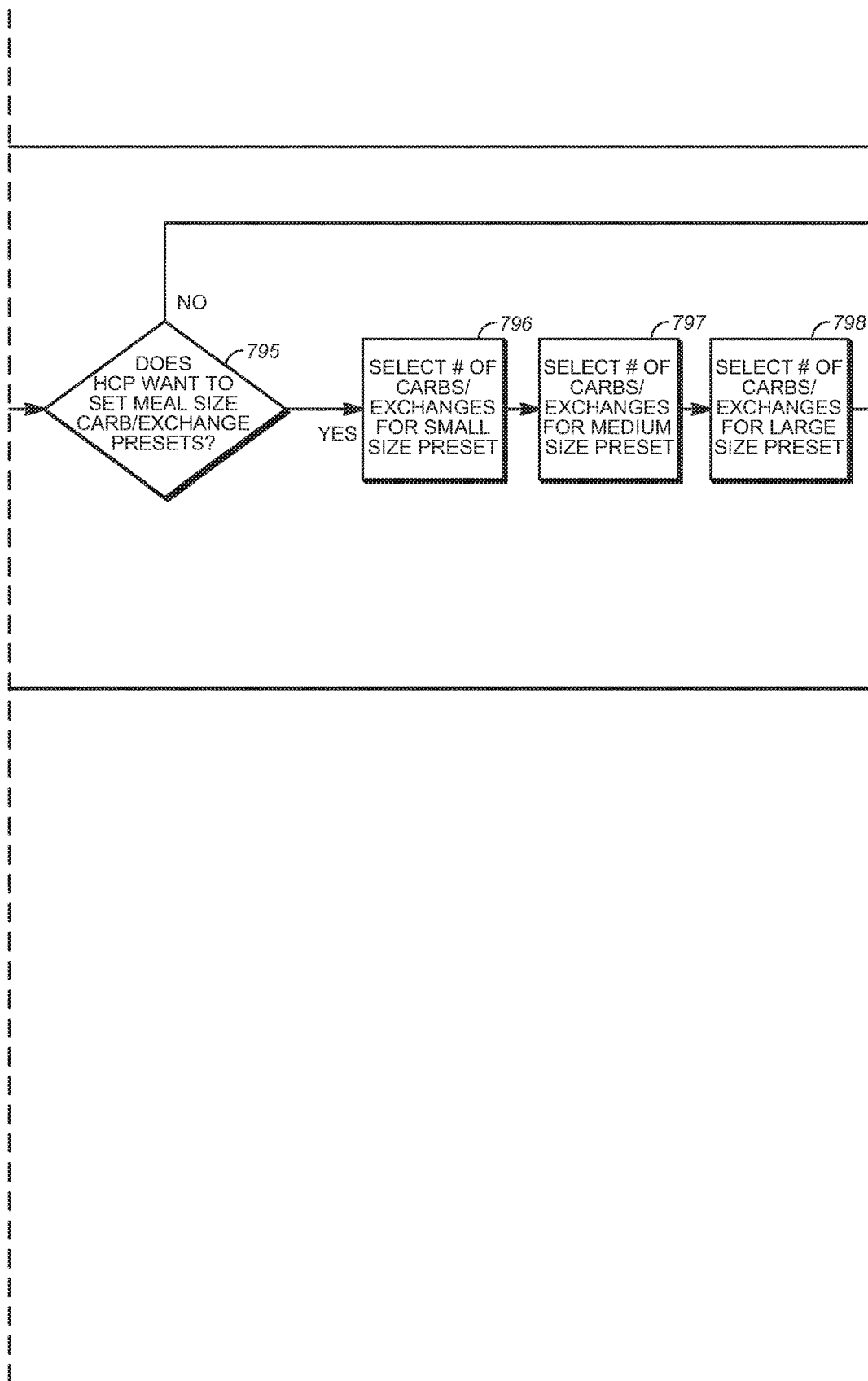
Figure 7O:
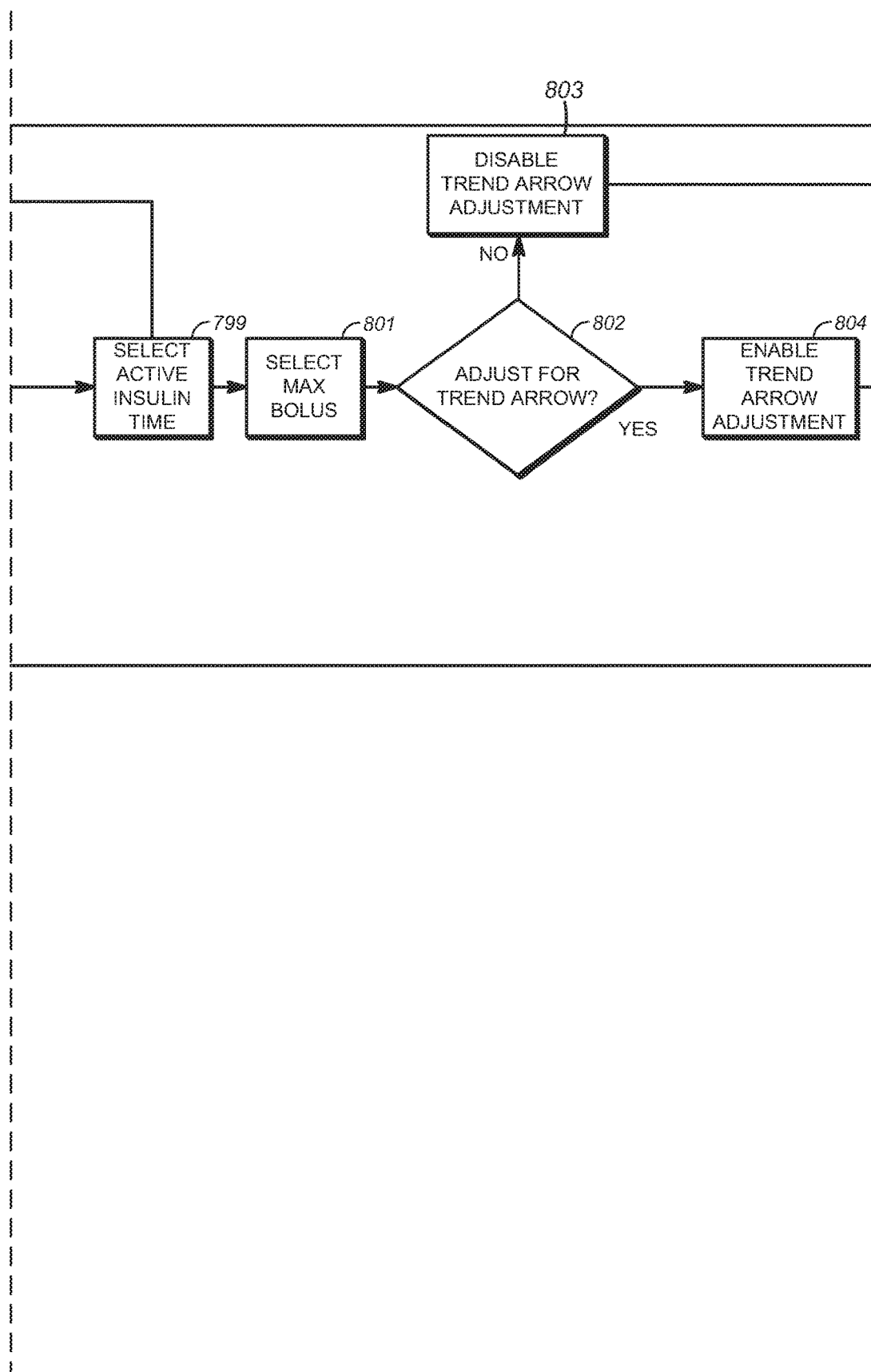
Figure 7P:
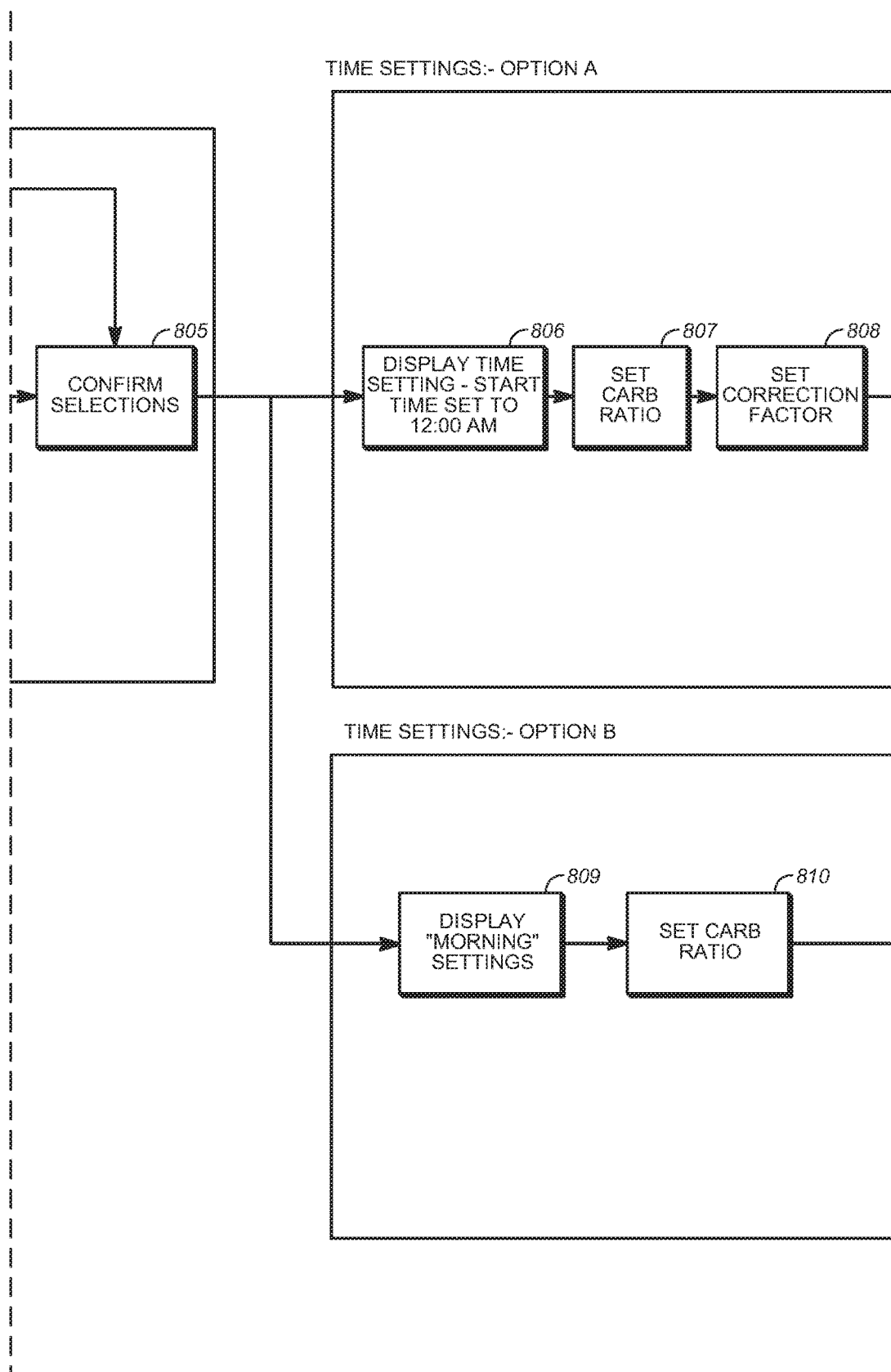
Figure 7Q:
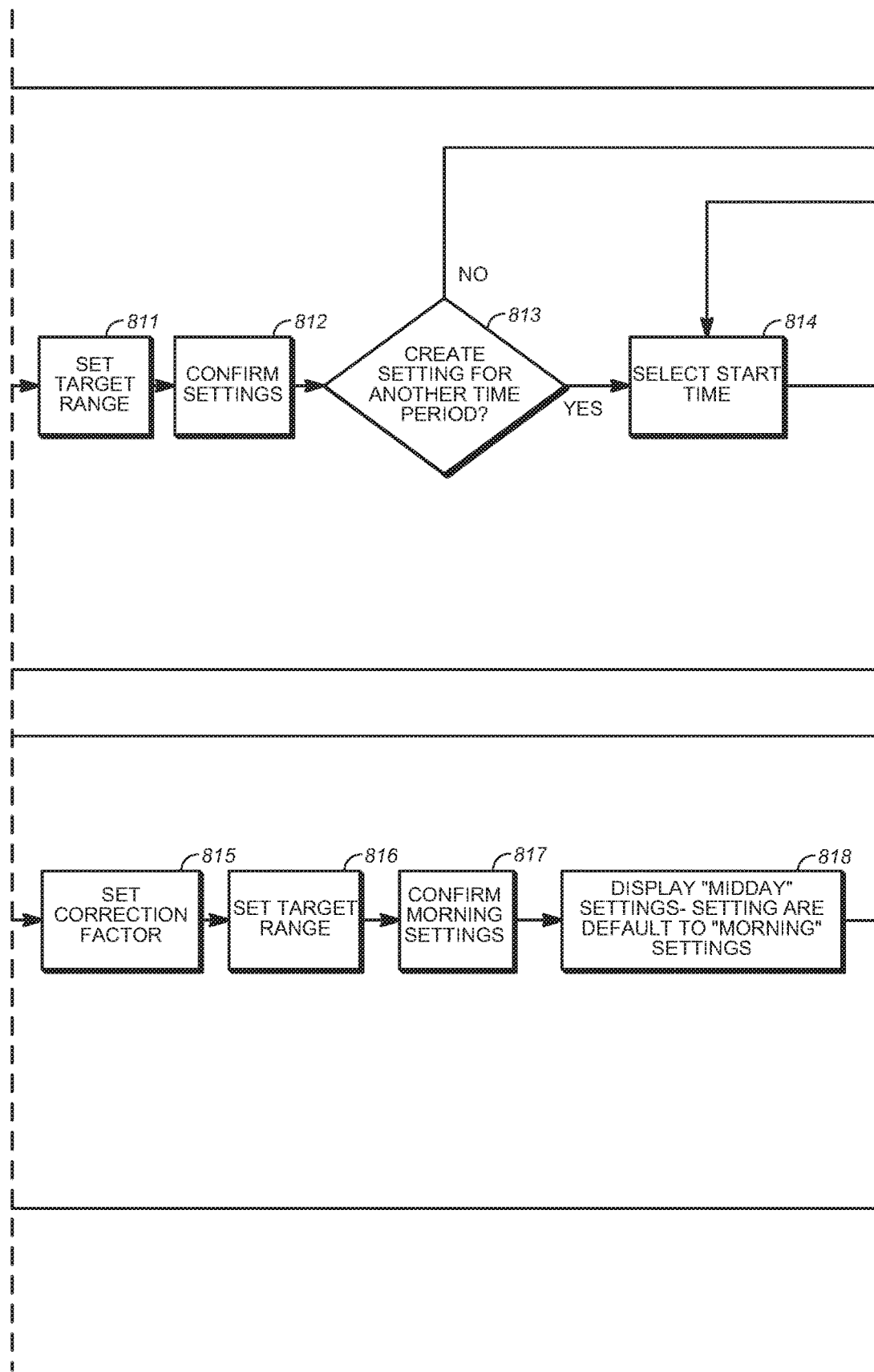
Figure 7R:
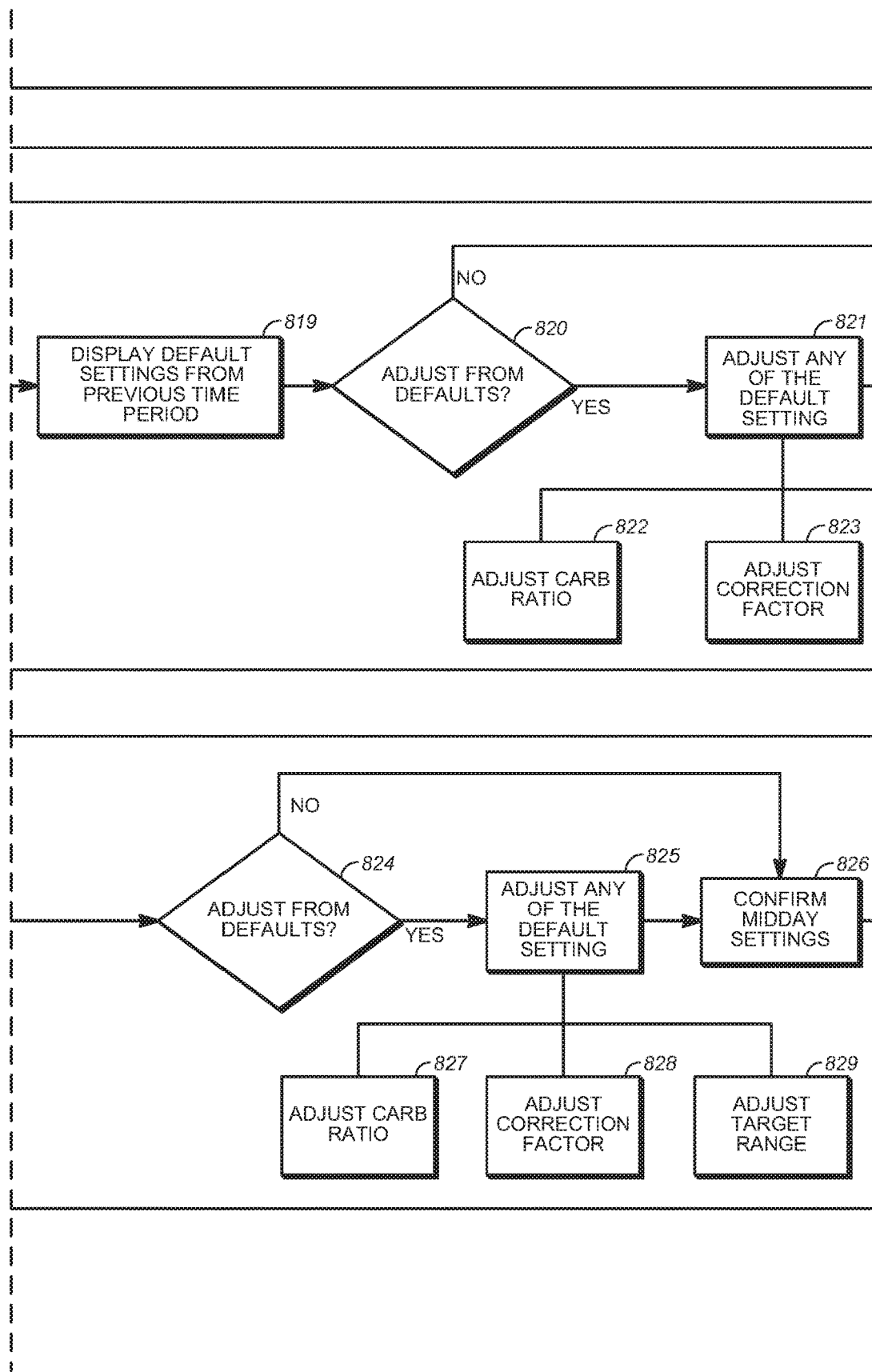
Figure 7S:
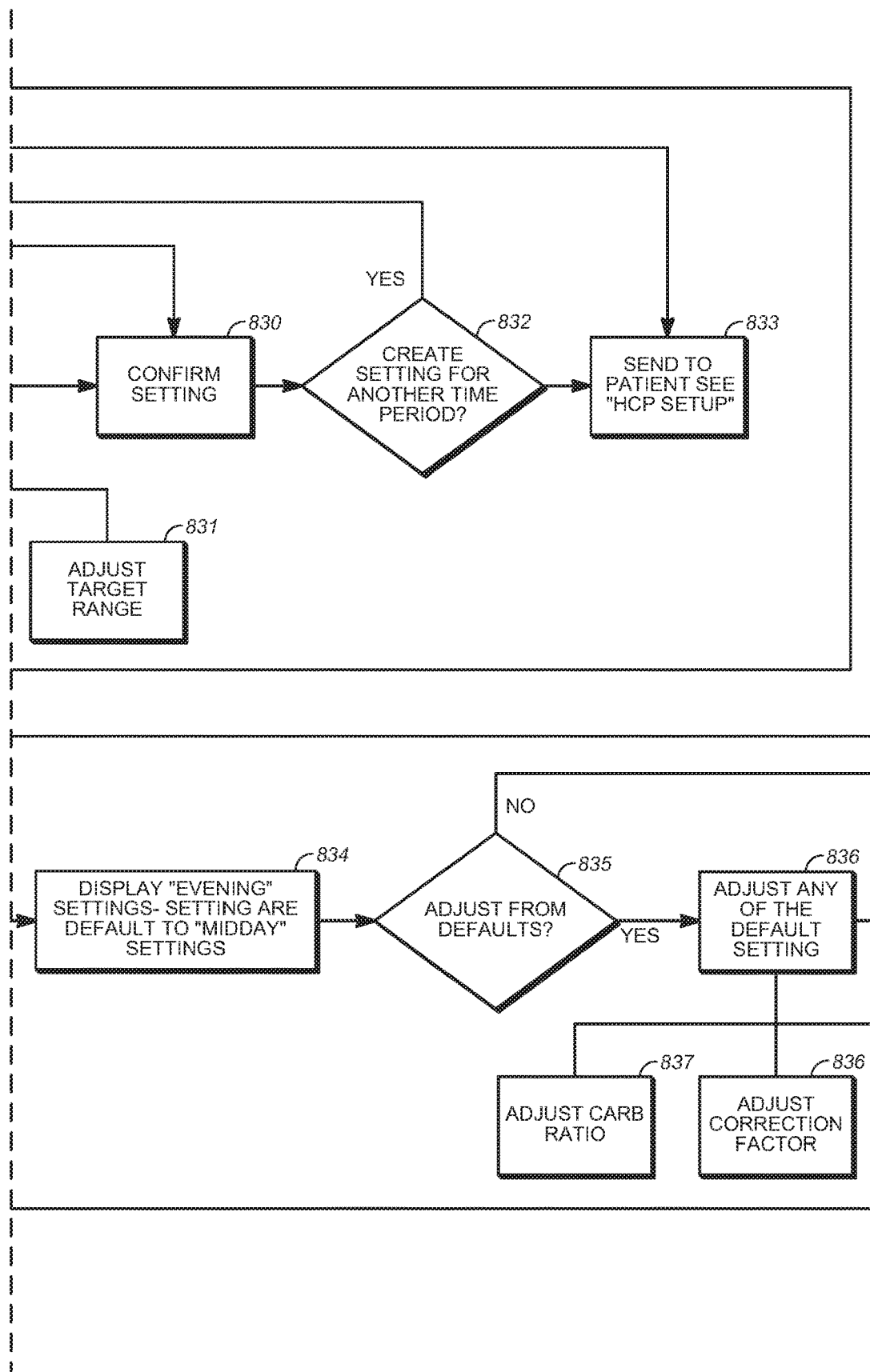
Figure 7T:
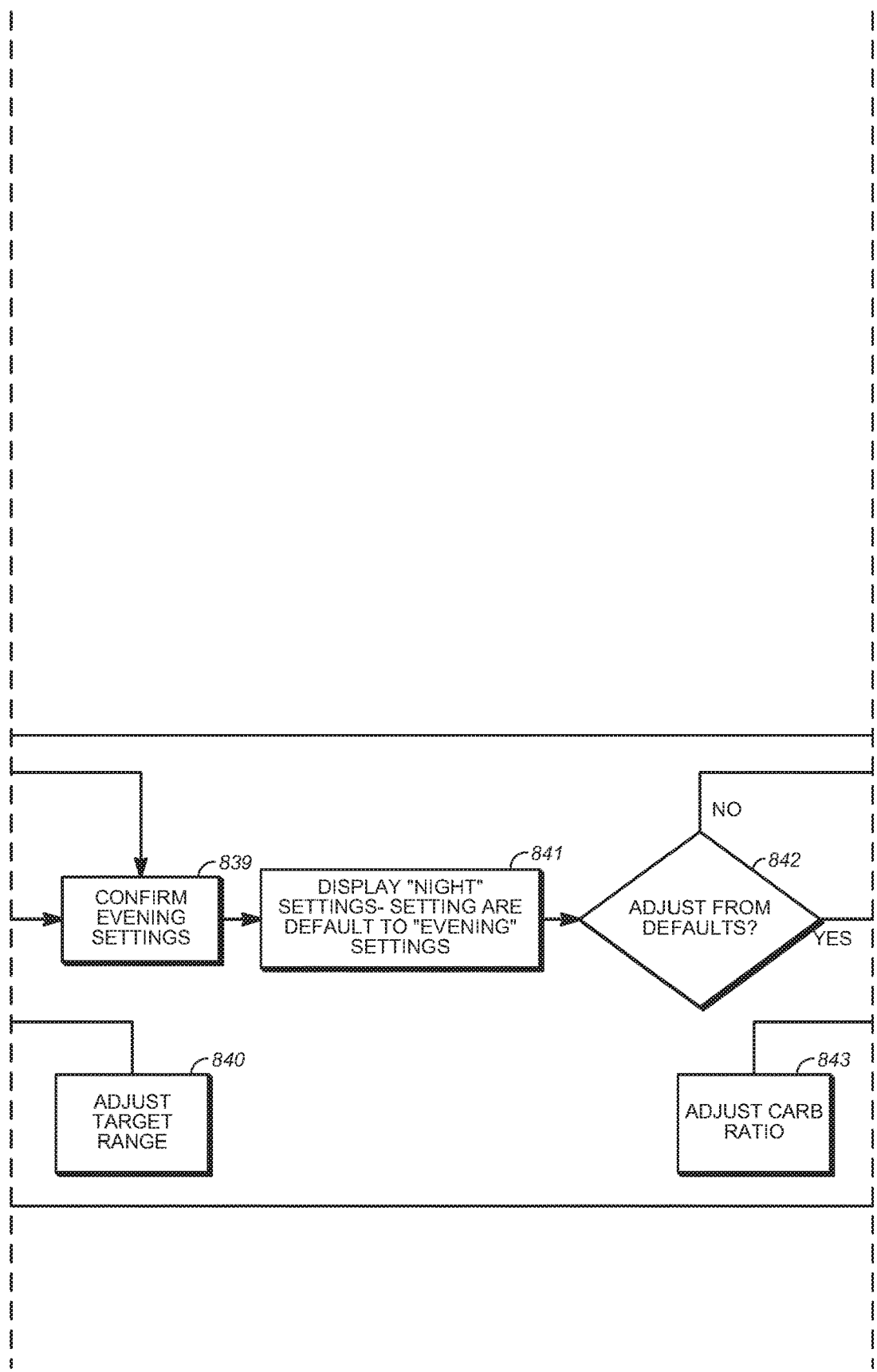
Figure 7U:
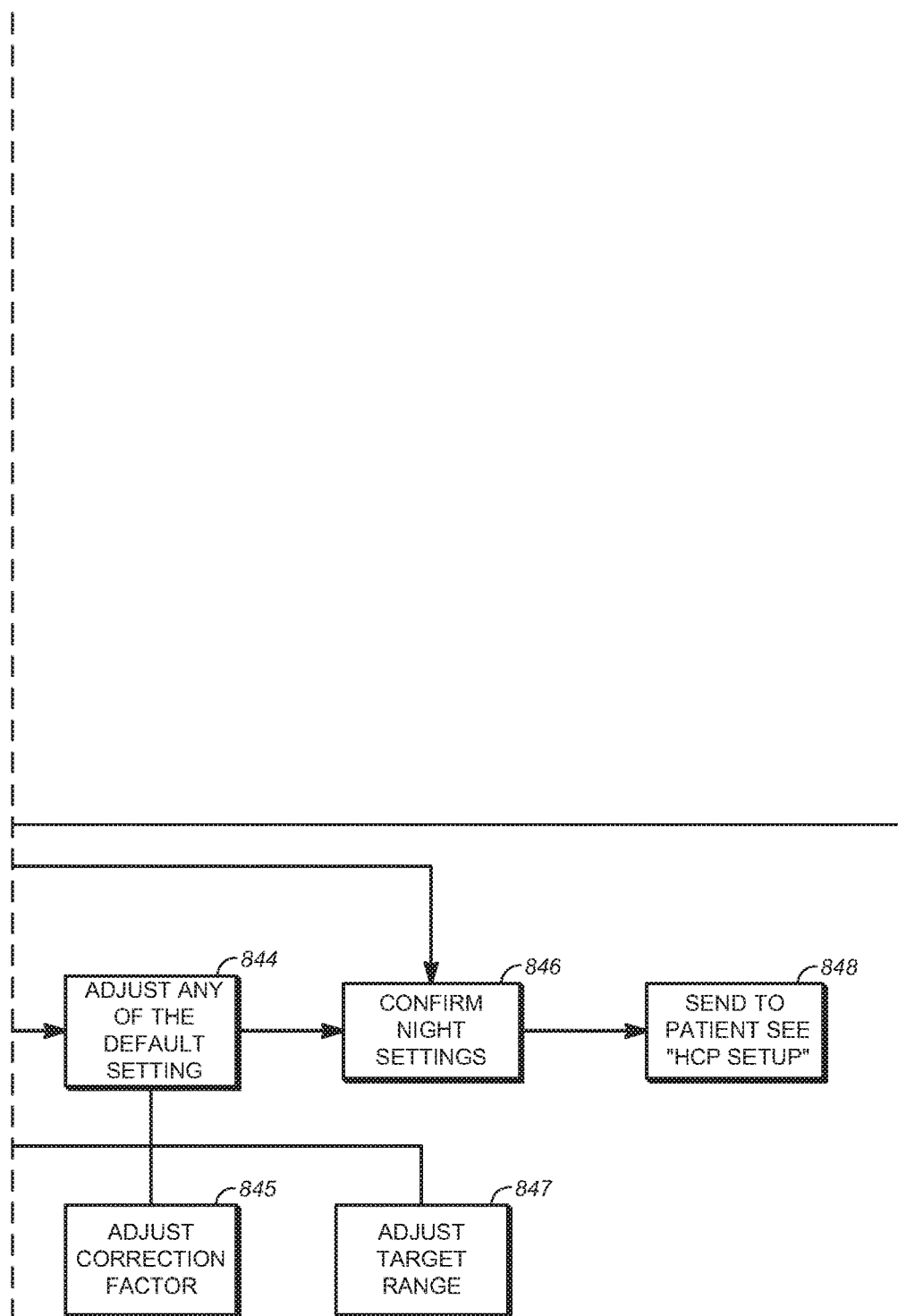

In another implementation, as illustrated in FIGS. 7F-7H, bolus calculator parameters may be automatically set up by an HCP. In particular, in a first step, an HCP may access a web application home page (step 745). The HCP may activate or press an appropriate button for HCP set up (step 746). The HCP may be prompted as to whether they are actually an HCP (step 747). An appropriate authentication procedure as in FIGS. 7A-7E may be performed. If the HCP cannot be appropriately authenticated, control may pass back to the homepage of the web application (step 745). Assuming the HCP is properly authenticated in step 747, a legal statement may be displayed (step 748), and the HCP may be prompted as to whether they consent to the actions of the app, e.g., bolus calculator set up (step 749). If they do not so consent, control may pass again to step 745. If the HCP does consent, they may be prompted to enter their name (step 751) and their NPI number (step 752). The system may check as to whether the NPI is valid (step 753). If the NPI is valid, control may pass to a step of entering a code from the patient (step 754). If the NPI is not valid, an error message may be displayed (step 755), and control may pass again to the name entry (step 751).

The code from the patient may be as described below, e.g., a one time code which is valid for a limited duration, which allows the HCP to access the patient file and provide bolus calculator adjustments. The patient code may be entered first, so that the HCP does not fill out bolus calculator settings without the same being associated with the patient. The code may be checked as to its validity (step 756). If the code is not valid, an error message may be displayed (step 757), and the HCP may be prompted to reenter the code (step 754). However, if the code is valid, the patient's name may be displayed, the name pertaining to and keyed off of the code (step 757).

The HCP may be prompted as to whether the correct patient file is being worked on (step 758). If not, control may pass to step 754. If the correct patient file is being worked on, the HCP may be prompted to enter the patient settings (step 756). Details of entry of specific patient settings may be seen in other flowcharts, including FIGS. 7A-7E. The HCP may be prompted to confirm the settings (step 757), and may further be prompted as to whether the settings are ready to be sent to the patient (step 758). If the settings are not ready to be sent to the patient, then flow may proceed back to step 756, with the patient settings being reentered. If the settings are ready to be sent to the patient, the HCP may be prompted as to whether they wish to save or print the settings file, e.g., as a PDF (step 759). If they choose to save the settings file, the same may be saved (step 760). If they choose to print the settings file, the same may be printed (step 761). If neither is chosen, the HCP may be prompted to confirm that the file will neither be saved nor printed (step 762). If the HCP does not so confirm, flow may proceed back to step 759. If the HCP confirms, then flow may return back to the display of the HCP web application home page (step 763).

FIGS. 7I-7L illustrate another flowchart using which an HCP can take part in bolus calculator set up. In a first step, the HCP accesses a home page of an application, e.g., a web application or website (step 764). While the nature of the web application can differ, a basic requirement is that the same be accessible by the HCP and also be accessible by a user, e.g., either to obtain parameters to manually enter into a bolus calculator or to download parameters directly into the bolus calculator. In the case of the HCP, the HCP may press, select, or otherwise activate a button indicating HCP bolus calculator set up (step 765). The system may ask if the user is an HCP (step 766). If not, the HCP can be taken back to the homepage (step 764).

If the user indicates they are an HCP, flow may pass to, e.g., an optional display of a legal statement (step 767). The legal statement can indicate various provisos and disclaimers for the use of the website in entering bolus calculator parameters. The HCP may be prompted as to whether they consent (step 768). If the HCP does not so consent, flow may pass back to the homepage (step 764). If, however, the HCP indicates consent, the HCP may be prompted to enter their name (step 769) as well as other information, e.g., an NPI number (step 771). The system and method may test if the entered NPI number is a valid NPI number (step 772). If the number is not a valid NPI number, an error message may be displayed (step 770) and flow may pass back to the information input screen(s) of step 769 and/or 771.

Once a valid NPI number is entered, flow may pass to begin a series of prompts for information about the patient. For example, where a patient has provided access to their EMR by use of a code, the HCP may be prompted to enter the code from the patient (step 773). By use of the code from the patient, any settings entered by the HCP will be automatically assigned to the correct patient, thus acting as a security measure. In addition, by use of a code from the patient, certain patient parameters may be pre-populated (if known), limiting data entry burden on the HCP.

The code entered by the HCP may be tested for validity (step 789). If the code is not valid, an error message may be displayed (step 774). Flow may then pass back to the "enter code" screen (step 773), for the HCP to reenter a different code. If the code is determined to be valid, the patient's name may be displayed (step 776). A feedback step may then be implemented, where the HCP is prompted to determine whether or not the correct patient file is being worked on (step 777). This provides confirmation that the HCP will be setting up parameters for the correct patient. If patient information is displayed corresponding to a patient who the HCP is not intending to enter settings for, then flow may pass to the "enter code" screen (step 773), for the HCP to reenter a new code. If, however, the correct patient is indicated in step 777, then the HCP may enter the patient settings (step 778). Details of the entry of patient settings are described in flowcharts above. The HCP may be prompted to confirm the entered settings (step 779).

The HCP may then be prompted as to whether the settings are ready to be sent to the patient (step 780). If not, flow may pass back to the entry of patient settings screen (step 778). If the HCP indicates that the settings are ready to be sent to the patient (as part of step 780), then patient settings may optionally be displayed as a form (step 781). In any case, patient settings may be transmitted to the patient.

The HCP may then be prompted to perform various actions, including saving the settings as a file, printing the settings, e.g., as a PDF, or exiting the web application (step 783). In one case, the HCP chooses to save the settings as a file (step 784). In another case, the HCP may choose to print the file (step 785). It is noted that the steps may also be performed immediately from step 782, namely, the step following HCP notification. In some cases, such options may be provided to the HCP before or in lieu of HCP notification, or before or in lieu of the display of patient settings as a form (step 781).

If the HCP chooses to exit, the system may ask if the HCP has already saved or printed the settings (step 786), and if not, the HCP may be confirmed that no such savings or printing are desired (step 787). If no such savings or printing are desired, or if the HCP has already saved or printed the settings, flow may pass to the display of the HCP web application homepage (step 788). If the HCP does not confirm that they desire no savings/printing, flow may pass back to the notification step (step 782).

In yet another implementation, as shown by the flowchart 775 of FIGS. 7M-7U, a process is shown in which additional details are shown for the set up of patient parameters for a bolus calculator.

In a first portion, an "all day setting" is set up.

A first step is for the HCP to enter a patient code (step 790). The way in which the HCP receives the code may be as described above in prior flowcharts. An all day setting may then be displayed (step 791). The HCP may be prompted to enter how is best appropriate for a particular patient to keep track of meals, e.g., by way of exchanges, carbohydrates, or the like (step 792). In one case, the HCP selects by way of exchanges (step 793). In another case, the HCP selects by way of carbohydrates (step 794).

The HCP may then be prompted as to whether they want to set meal size carbohydrates/exchange presets (step 795). If so, the HCP may be prompted to select the number of carbs/exchanges for a small meal size preset (steps 796), the number of carbs/exchanges for a medium meal size preset (steps 797), and the number of carbs/exchanges for a large meal size preset (steps 798). The HCP may also select an active insulin time (step 799), and may select a maximum bolus size (step 801).

The HCP may then select whether the bolus calculation should be adjusted for a determined glucose trend (step 802). This parameter is generally specific to continuous glucose monitoring, in which a direction and magnitude of a trend arrow may be determined. If the HCP indicates that no trend arrow adjustment is necessary, the trend arrow adjustment may be disabled (step 803). If the trend arrow is used, then the system may enable the trend adjustment (step 804). The HCP may then be prompted to confirm their selections (step 805).

Various time settings may then be indicated by the physician, and the same are noted here as a first option and a second option.

In the first option, a time settings period is prompted for (step 806). For example, the HCP may indicate a nighttime time period of 11 PM-7 AM. The HCP may enter a carb ratio (step 807), a correction factor (step 808), a target range (step 811), and so on. The HCP may be prompted to confirm the settings (step 812). The HCP may then be prompted to create settings for another time period (step 813). If they choose not to, flow may pass to a step of sending the settings to the patient for review (step 833). If the HCP chooses to create settings for another time period, then again a start time may be selected (step 814), and default settings may be displayed from a previous time period (step 819). The default settings may then be adjusted but otherwise used as base values (step 820). If an adjustment is made by the HCP (step 821), then adjustments may be made to the carb ratio (step 822), the correction factor (step 823), or the target range (step 831). As before, the HCP may be prompted to confirm the settings (step 830).

The HCP may be given the option to create settings for another time period (step 832). If they choose to, flow may pass to step 814. If they do not choose to, the settings may be sent to the patient (step 833). The step of sending the settings to the patient, and soliciting patient response, may be as described above.

In the second option, an initial display may be of a particular time period, e.g., a display of "morning" settings (step 809). For these the HCP may set parameters as indicated above, including carb ratio (step 810), correction factor (step 815), and target range (step 816). The HCP may be prompted to confirm these "morning" settings (step 817).

Similarly, another time period setting may be indicated of a particular time period, e.g., a display of "midday" settings. Settings may be defaulted to the "morning" settings, but may be conveniently adjusted. Accordingly, the HCP may be prompted as to whether they wish to adjust the settings from the default values (step 824). If they choose not to, then the midday settings may be confirmed (step 826). If, however, the HCP chooses to adjust from the defaults as part of step 824, then any of the default settings may be adjusted (step 825), including an adjustment of the carb ratio (step 827), an adjustment of the correction factor (step 828), and/or an adjustment of the target range (step 829).

Following the confirmation step 826, a display of "evening" settings may be provided (step 834). Again, the default may be the previously entered midday settings. The HCP may be prompted as to whether they wish to adjust the settings from the default values (step 835). If they choose not to, then the evening settings may be confirmed (step 839). If, however, the HCP chooses to adjust from the default values as part of step 835, then any of the default settings may be adjusted (step 836), including an adjustment of the carb ratio (step 837), an adjustment of the correction factor (step 838), and/or an adjustment of the target range (step 840).

Following the confirmation step 839, a display of "nighttime" settings may be provided (step 841). Again, the default may be the previously-entered evening settings. The HCP may be prompted as to whether they wish to adjust the settings from the default values (step 842). If they choose not to, then the nighttime settings may be confirmed (step 846). If, however, the HCP chooses to adjust from the defaults as part of step 842, then any of the default settings may be adjusted (step 844), including an adjustment of the carb ratio (step 843), an adjustment of the correction factor (step 845), and/or an adjustment of the target range (step 847).

The confirmed settings for the various time periods may then be sent to the patient (step 848). The patient may receive the settings and automatically have the settings downloaded into their bolus calculator, may enter displayed settings manually, patient response may be solicited, or other patient interactions may be performed.

Variations Specific to HCP Setup—Initial Setup and/or Updates

Variations of the above HCP set up systems and methods according to present principles will also be understood. Such variations include provisions for HCP update of already set parameters.

Figure 8:
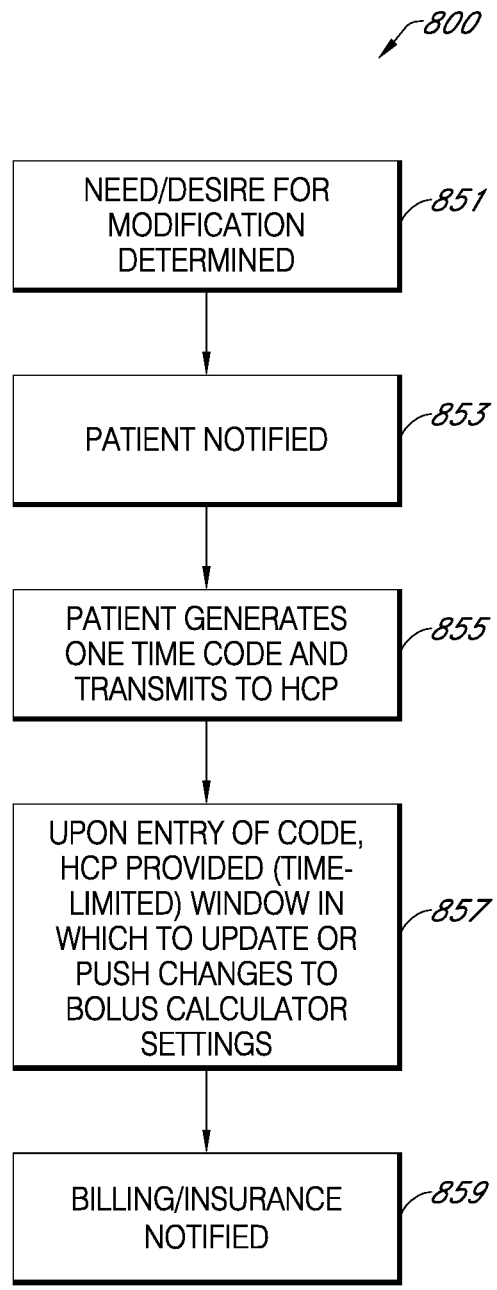
FIG. 8 illustrates a flowchart of another implementation of a method according to present principles.

FIG. 8 is a flowchart 800 indicating a method for updating bolus calculator parameters. In one implementation, the patient may be enabled to generate a one-time upload code, and to transmit the code to the HCP to allow bolus calculator modification.

In more detail, a need or desire for a bolus calculator modification may be determined (step 851), and the patient may be so notified (step 853). For example, pattern recognition or other techniques may be employed to determine that, even with a current set of bolus calculator parameters, a patient is out of a target range an undesirable amount of time, e.g., an undesirable percentage of time. In a particular example, if a patient is out of a target range for a percentage (or other measure) for greater than a certain predetermined threshold criterion amount, then the patient may be notified that a change in bolus calculator parameters may be warranted or desirable. The notification may be by way of HCP action, or may occur automatically, e.g., the previously-noted pattern determination, the recognition of atypical signal responses and behaviors, and so on. The patient may then generate a one time code (as in the manner described above) and transmit the same to the HCP (step 855). In particular, the notification to the patient may provide a link to a URL/URI using which the patient may generate a code. Alternatively, the patient may access a desktop application or smart phone app to generate the same (which may also be used to receive the notification). The code may be of various forms, including QR codes, barcodes, or the like. In one implementation, the code is simply a string of generated alphanumeric characters which may be entered by the HCP on the HCP portal to allow access and modification of a user's bolus calculator parameters. The code may be of various types, but generally a one time code is used, such that the code may be entered one time to allow HCP modification of bolus calculator parameters, and after a specified duration of time, the code no longer works; if additional bolus calculator parameter modifications are desired, a new one time code is required to be generated. Each one time code may work to allow modifications for a specified duration of time, e.g., 10 minutes, 30 minutes, one hour, and so on. That is, the HCP may be provided a time-limited window in which to update or push changes to such bolus calculator settings.

The HCP may enter the one time code into the system and may then be given temporary access to the user's current bolus calculator settings (step 857), e.g., either in real time or by way of construction/modification of a set of bolus calculator parameter settings which are then transmitted to the bolus calculator for installation. Exemplary values which may be modified include, e.g., insulin to carb ratio, insulin action time, and the patient's correction factor. While such codes may also be used in conjunction with HCP accounts, also, by the use of such codes, the HCP may be prevented from having to set up and access an account. Code generation and subsequent parameter modification may even be performed during a phone consultation, and such a consultation may generate a billable event for insurance (step 859).

Some example benefits include the elimination of the necessity of setting up a password and database access for each HCP. Updates may be pushed on the fly and the HCP may be enabled to view, and potentially discuss with the patient, the current real time apps settings. Bidirectional security is provided, as well as compliance with HIPAA. In addition, a brief report may be generated pertaining to the same as evidence of the contact for billing purposes.

In many of the above described implementations, the HCP may initiate the set up, and may set up the patient account online, setting thresholds and other customized settings. The HCP may then send an invitation to the patient, eliminating the need for the patient to enter settings and get access to physician recommendations. In a particular variation of these implementations, once the patient accepts the invitation and starts the sensor session, the HCP may receive electronic information such as data from the patient. In addition, in some implementations, the patient may automatically, or after clicking a button in the app, give the HCP permission to view patient data. In this way, the HCP may be enabled to automatically get access to such data, and the patient is no longer burdened with sending an invitation to the HCP. Such data may be forwarded to an EMR or other such electronic record or database.

Specific functionality that an HCP can set up is described below. In one implementation, a CGM app is set up with a bolus calculator tool for MDI users using a CGM only system configuration. However, some or all of the features may be employed for non-MDI CGM systems, e.g., users with CGM and insulin pumps.

In one implementation, the bolus calculator tool uses user input of insulin doses to determine various factors useful in bolus calculations, e.g., factors such as IOB. Such user input is generally required in such systems, e.g., for MDI users, as there is generally less ability for automatic input of such parameters, in contrast to the case with a connected pump. However, in some cases data may be available from an insulin pen via Bluetooth (or other communication protocols and techniques), thus negating the need for separate user input.

In this implementation (and in others), insulin dose recommendations from the bolus calculator can be accepted or modified, and data about such recommendations, whether they are accepted or rejected or modified, as well as subsequent glucose response data, can be used to inform future IOB determinations.

To enter such data, users may enter insulin boluses, e.g., logging them as an "event", using an event input feature of the CGM app. In some implementations, users can be warned during initial setup that the bolus calculator relies on their insulin bolus inputs for accurate estimates of IOB, and that there is a risk of dangerous insulin recommendations if they do not enter this information, or if they enter incorrect information.

For non-MDI users, e.g., those using an interactive CGM—insulin delivery system configuration or arrangement, the CGM app bolus calculator may provide recommendations that are different from the bolus calculator on an insulin pump. Such differences can arise because of a difference in settings, a difference in IOB calculations, the use (or not) of glucose trend information, and other related factors. And in the same way as MDI users, the CGM app user can be presented with a warning during initial setup of the bolus calculator tool that informs the user of such potential differences between the bolus calculator tool and a bolus calculator associated with an insulin delivery device.

For example, in a connected pump system configuration in which the insulin app provides its own bolus calculator, the CGM app bolus calculator can be deactivated or disabled to avoid user confusion, particularly in the case where the bolus calculator associated with the insulin delivery device is "trusted" and authenticated. In this case, when the user activates the bolus calculator option in the CGM app, the user may be presented with the bolus calculator in the insulin app associated with the insulin delivery device. Such communications between apps, generally by way of appropriately configured APIs, generally invoke security considerations so as to ensure that data received from an app is accurate, trustworthy, and associated with the correct patient.

Various parameters that may be set up are now described. In one example, an HCP may set up a preset meal bolus. In one implementation, the preset meal bolus provides a "fuzzy" meal entry for the bolus calculator. The CGM app can provide preset meal boluses based on a number of factors, including the user's typical intake values for breakfasts, lunches, dinners, and/or snacks. Such may be particularly beneficial for users who do not wish to count carbs but who consistently eat similarly-sized meals each day. For example, the HCP may determine, in consultation with the patient, that patient meals may be entered as inputs into a smart device, and for the sake of user convenience and because of user consistency with regard to such meals, may be more easily entered as fuzzy or within categories, e.g., small, medium, or large, with further categorizations (or "fuzzifications") corresponding to, e.g., relative amounts of carbohydrates/fats/proteins. Similar data may be entered as "crisp" if the user is aware of the number of carbohydrates or other such data. The type of calculation, or confidence of calculation, performed by the bolus calculator may be based at least in part on whether the user provides precise or crisp data, approximate data, fuzzy or categorized data, and so on. For example, the calculation may differ if the user enters "3 carb units" versus "big meal".

The HCP can provide the preset meal boluses during initial setup, and may modify these values according to the update routines subsequently. The bolus calculator then recommends an insulin bolus that also accounts for glucose correction, trend adjustments, and IOB.

In another variation, the HCP can provide basal rates to a CGM app using an EMR system. In more detail, the HCP can enter recommended basal rates into an EMR system, and the EMR system can then transmit the recommended basal rates to the patient's CGM app, e.g., which includes the bolus calculator tool. An appropriate API may be configured to allow communications between the EMR system and the CGM app. The patient can view the recommendation and either confirm or deny the settings. In some cases, a comment field may be provided for the patient to explain why certain actions are being taken, or for the HCP to explain why the change is being suggested. On the HCPs end, the HCP can view if the patient confirmed or denied the basal changes.

In the same way or similar ways, data discussed with an HCP at an appointment can be entered into their data profile through an appropriate UI, and may be then transmitted to the CGM app using an appropriate secure procedure. In some cases, the "data profile" may be the above-noted EMR system, and in other cases it may be a different application, which may or may not be in data communication with the patient's EMR.

In yet another variation, near field communications (NFC) may be employed to communicate data such as settings, configuration parameters, and the like, to the patient's mobile device, e.g., smart phone. In more detail, NFC on a mobile phone can be employed to scan the transmitter, which would then automatically cause the phone and transmitter to set up the system, such as downloading the CGM App on the phone (from the transmitter), pairing the phone and transmitter, and in some implementations even initiating the sensor start up. Such systems and methods according to present principles remove the step of having to enter a code, with the "cost" being that the devices have to be next to each other. However, a significant advantage is that the devices cannot be easily hacked from a distance.

In more detail, in this implementation, the transmitter itself may store the application for various devices, e.g., iOS and Android, and upon the pairing process, the transmitter may transfer the application directly to the smart phone it is being paired with. Such is beneficial as downloading the actual app, e.g., which often requires a strong data connection, may be particularly difficult or challenging in certain situations, and due to privacy issues, the ability of patients to get access to the hospital or doctor's Wi-Fi network may also be challenging. Thus, if the pairing is initiated by a technology like NFC, and if the application is transferred in the same way, such would provide significant benefits to the user. NSF may also be employed to update the application, or the application may be updated when the user is near a strong Wi-Fi connection.

Systems and methods according to present principles may pertain not only to initial setup of a bolus calculator app or functionality, but also to updates of the same, e.g., based on data subsequently learned about the patient and/or sensor, i.e., data learned subsequent to initialization of a sensor session. Such may be particularly important as sensor sessions are generally getting longer, with patients getting more days' use out of a sensor than previously.

Figure 9:
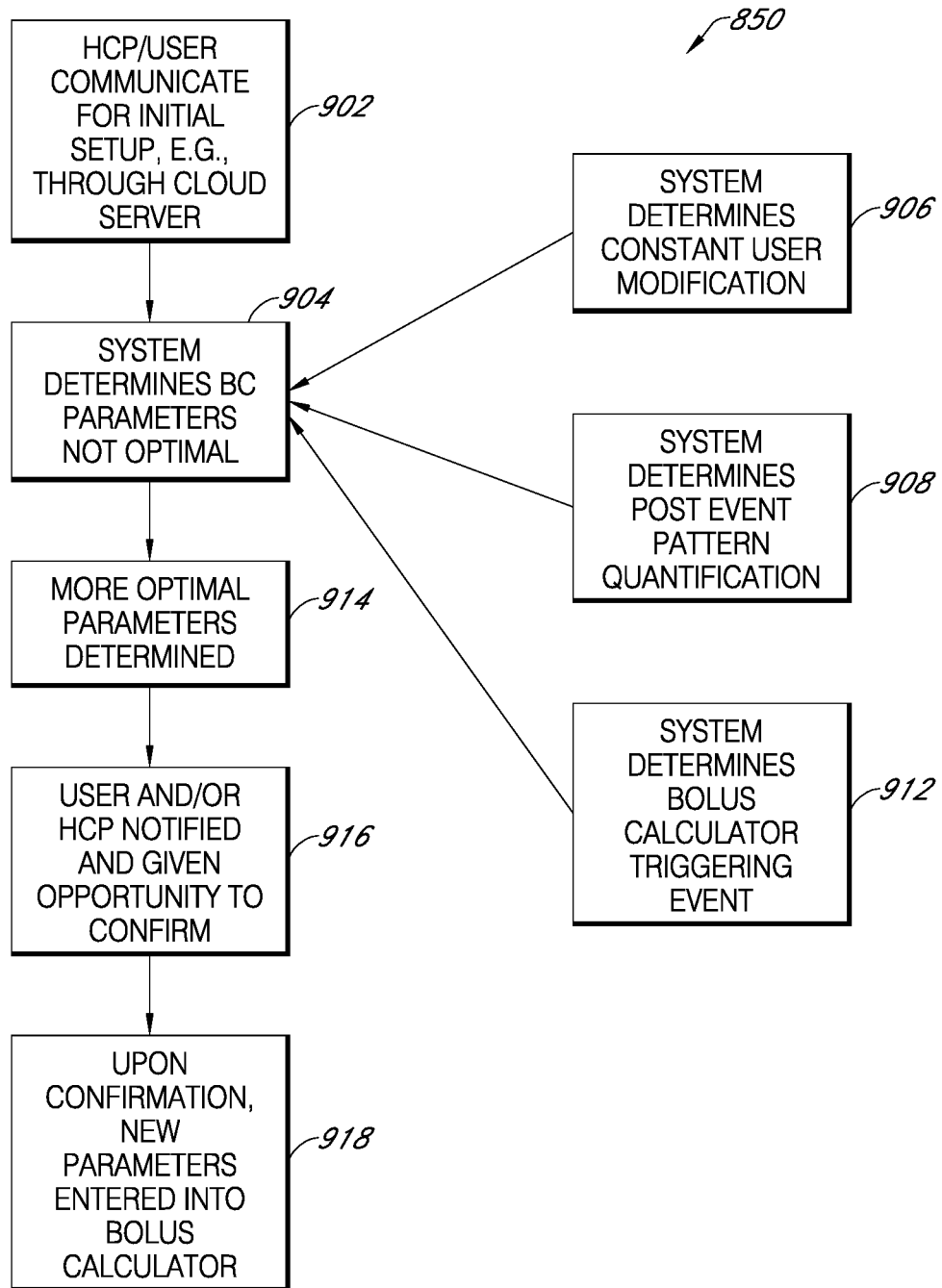
FIG. 9 illustrates a flowchart of another implementation of a method according to present principles.

In one implementation, and referring to the flowchart 850 of FIG. 9, an HCP and a user may communicate for initial setup of a bolus calculator (step 902). Such set up may occur in the fashion noted above, e.g., through a cloud server, peer-to-peer system, or the like. The system may then determine that the bolus calculator parameters are sub optimal or may otherwise be improved (step 904). This determination may be in a number of ways. For example, the system may determine that the user often or always makes a change to their bolus calculator calculation (step 906). For example, the user may consistently add a unit to every bolus. If the user's glucose response is determined to be that too much insulin was delivered, then such may be automatically flagged and used as a discussion point for the next visit between the user and the HCP. However, if by doing so the user keeps their glucose level within target range, then such may indicate a change is needed to the bolus calculator parameters.

In another example, the system may automatically determine a post-event pattern quantification (step 908). In this example, the system may review historical data to determine if patterns are present that can be addressed by a change to bolus calculator parameters. It is noted in this regard that some patterns can be addressed in this way, and others cannot. If a pattern is seen that can be addressed, a suitable change the bolus calculator parameters may be determined and transmitted to the user's bolus calculator app.

More generally, the system may determine a bolus calculator triggering event (step 912). In more detail, the system may detect an event or series of events that can be beneficially and efficaciously addressed by way of a change to bolus calculator parameters. If the system is so triggered, and can uniquely determine a proposed modification solution, then the same may be proposed as a potential change to bolus calculator parameters or settings. In some cases a unique and definite solution will not be immediately calculable, but a qualitative direction of parameter modification may be determined. For example, it may be determinable that bolus is calculated with current parameters are generally too small. In this case, it may be determined to change parameters such that bolus amounts are increased.

However it is determined that the bolus calculator parameters/settings are sub optimal, more optimal or improved parameters may be determined (step 914). As indicated above, in some cases a direction and magnitude of change may be determined, while in other cases only a qualitative direction of change may be capable of being determined, given currently available data. In some cases, a qualitative magnitude of bolus calculator parameters/setting change may be determinable, while in other cases, with more available data, a more quantitative magnitude of change may be capable of being determined.

Once a potential modification is determined, e.g., either qualitative or quantitative, the user and/or the HCP may be notified and given the opportunity to confirm that the modification should actually be attempted (step 916). Upon confirmation, the modified parameters may be entered into the bolus calculator app or functionality (step 918).

It is noted that any number of known data (including deduced quantities such as patterns of data) may be potentially "mined" for data that may be useful in modification of bolus calculator settings and/or control of medicament delivery devices.

For example, in the determination of step 906 above, a pattern may be detected by the system that the user is constantly delivering boluses that are different from those calculated by the bolus calculator. In this example, it is particularly important that the user be notified of changes to bolus calculator settings, because in the absence of such notification, too much insulin may be delivered by the system. The detection of such user departures from calculated values may be by analysis of periodic, occasional, habitual, often, constant, or regular departures from calculated values, where the departures are roughly of the same magnitude, e.g., within a range, and the same sign. For example, the user may occasionally or frequently depart from calculated bolus values by +1 unit, by −1 unit, and so on.

In response to detection and notification of bolus calculator triggering events, an HCP may take various actions. One action is to modify the bolus calculator settings/parameters, and transmit the same back to the patient. Steps of this method may include certain steps described above in connection with FIG. 8, including patient generation and HCP reception of a one time code allowing modifications to bolus calculator parameters. Alternatively, if sufficient encryption and/or a secure communications channel exists between the HCP portal and the patient's bolus calculator, the HCP may be enabled to modify parameters in the absence of a one time code. In general, it is expected that most users would desire to approve bolus calculator modifications, and thus the bolus calculator app (or CGM app with bolus calculator functionality) may be configured to prompt the patient for approval prior to actual modification of bolus calculator parameters, even if the same have already been downloaded into a device. Another action is to provide a notification to the insurance company that a consultation has occurred, and thus a billing event may be present. In this action, if a consultation has occurred between the patient and an HCP, then such may, depending on the consultation, constitute a billing event, and the billing for such an event may be eased or made more convenient by automatic notification to a payor, e.g., insurance company, of the consultation. The consultation may constitute a number of forms, including: (1) a detection of BC triggering event; (2) notification to the patient; (3) patient generation of code and transmittal to HCP; (4) HCP use of code in modification; and (5) patient approval of modification and installation of modified parameters to the bolus calculator app/functionality. Another form the consultation may take includes: (1) a detection of BC triggering event; (2) HCP initiated notification to the patient; (3) patient approval of potential modification and transmittal of approval to HCP; (4) HCP modification of BC parameter and/or transmittal of modification in a secure and/or encrypted fashion to a bolus calculator; and (5) patient approval of modification and installation of modified parameters to the bolus calculator apps/functionality. Other methods will also be understood. In all of these, the way in which the consultation is performed, i.e., using efficiencies and other benefits gained by use of systems and methods according to present principles, can provide significant health benefits to the patient, as modifications are determined to be necessary and made more promptly. The same can further provide significant technical benefits, as the transmissions of short messages between patient devices and HCP devices provide distributed processing and/or peer-to-peer communications that allow modifications to be made without, e.g., a patient having to bring their smart phone into a doctor's office and have the same connected to a clinic computer or the like.

Another action is to notify the patient that a doctor's appointment may be necessary. In this example, an automatic notification to the payor may also be made. This type of action may generally be performed where the physician feels an in office consultation is necessary or desirable.

Another action is to potentially notify the patient of an act to take that does not involve medicament, e.g., to get more sleep or exercise. However, a general commonality in such actions is that they involve a deficiency in bolus calculator parameters/settings that are at least partially remediable by a modification to such parameters or settings. For example, it is not just that a pattern is detected that a user encounters nighttime lows; rather, the system determines that a pattern of nighttime lows is remediable by a modification to parameters or settings of a bolus calculator.

To accommodate the busy schedules of most HCPs, potential bolus calculator modifications of settings/parameters may be grouped such that the HCP receives a grouped set for a particular patient only periodically, e.g., once a week. Additionally, or alternatively, potential modifications may be prioritized or ranked so that the most important ones are addressed first. For example, acts (involving dosing) taken by a patient that result in an undesirable response may be provided with a certain number of points, and once a threshold level of points is reached, either a total number or on a periodic basis, then the act with the threshold exceeded may be flagged for review by the doctor.

In a particular implementation, an automatic review may include having the system review patient meals, not necessarily on a time-based system but rather based on the event of a meal occurring. A period of time after the meal, e.g., four hours, it may be determined if the patient is within a desired target range, or high or low. If a certain threshold number of days out of the week the patient is not in range, then it may be desired that a change be made. For example, if the patient is out of range five out of seven days, a change may be called for. These and other methods may be employed to determine the results or satisfactory (or not) nature of a set of bolus calculator parameters/settings.

In yet another variation, different groups of parameters/settings may be found appropriate for different times of day, or to address particular events, and settings and parameters may be modified according to the system knowledge as to whether such events or times of day are currently taking place. See, e.g., FIGS. 7M-7U above.

Generally, the above systems and methods use historical data, including inferred quantities such as patterns, to inform a real-time present suggestion or change to a parameter or setting of a bolus calculator. While the determination of the change or modification is at least in part automatic, implementation of the change itself may be subject to confirmation by the patient, HCP, or both.

Example Bolus Calculators

A bolus calculator is an important tool for a user to manage their diabetes. Bolus calculators make math considerably easier for the patient, and are less susceptible to human error. Current bolus calculators are generally only available on insulin pumps.

An exemplary calculation may be as follows. In an equation operative for a bolus calculator, an appropriate insulin bolus may be equal to a correction factor plus a factor related to current carbohydrates plus a factor related to IOB. Carbohydrate "coverage" is generally equal to a number of carbohydrates divided by the ICR, and the correction is equal to the current glucose value minus the target value divided by the correction factor. A trend adjustment in one estimation is equal to a rate of glucose change times the time period, e.g., 20 minutes, divided by the correction factor. In essence, the correction and trend adjustment is equivalent to predicting what the glucose level would be 20 minutes from a current time, assuming the current rate of change remains constant, and correcting based on the future glucose level.

In an exemplary calculation without trend adjustment, blood glucose may be 165; a target value may be 100; a number of carbs may be 45; an ISF may be 1:35; and an insulin-to-carb ratio (ICR) may be equal to 1:12. A last bolus taken may be three units, three hours ago. For a particular type of insulin, the duration of insulin action (DIA) may be four hours. The correction is 165-100 or 65. 65 applied to the ISF gives 1.86 units. The carbohydrate value is 45 carbs, which given the insulin-to-carb ratio of 1:12, constitutes 3.75 units. The IOB is three units, which acting over four hours, leave 0.75 units left. Thus, a total dose equals 1.86+3.75-0.75 or 4.86 units. Bolus calculators employing CGM functionality can be even more accurate, as the same use the current CGM glucose value and trend to determine how much insulin is needed for correction. Trend information has been shown to be particularly important, and has been shown to lead to far superior results than when trend is not accounted for.

Figure 10:
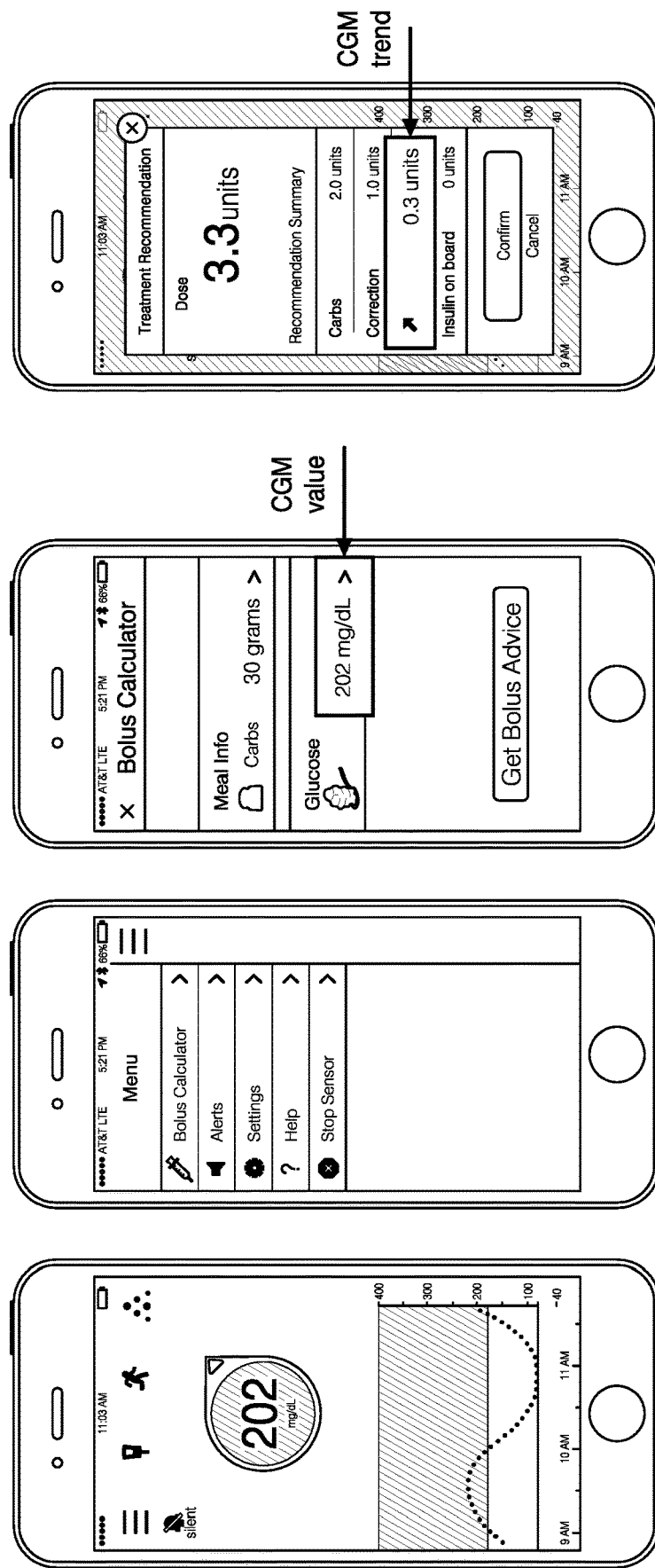
FIG. 10 illustrates an exemplary user flow of a bolus calculator according to present principles.

The bolus calculator as noted above may be an integrated feature in a CGM app or may alternatively be a separate app in communication with the CGM app, and can use both the current CGM glucose value and trend to determine insulin doses. An example user flow for the bolus calculator is shown in FIG. 10. As may be seen, a user can always choose to enter a meter glucose value instead of the CGM value, particularly when CGM values are unavailable. In addition, a trend adjustment is included to take into account where glucose is headed at the time of an insulin bolus, which can influence where glucose stabilizes, relative to target, after a meal. The trend adjustment may be calculated as a current rate of change (mg/dL/min) multiplied by a time factor (e.g., 20 minutes) and divided by the patient's personalized correction factor (mg/dL/units). In one example, the trend adjustment is correcting for the expected glucose change in the next 20 minutes.

Figure 11:
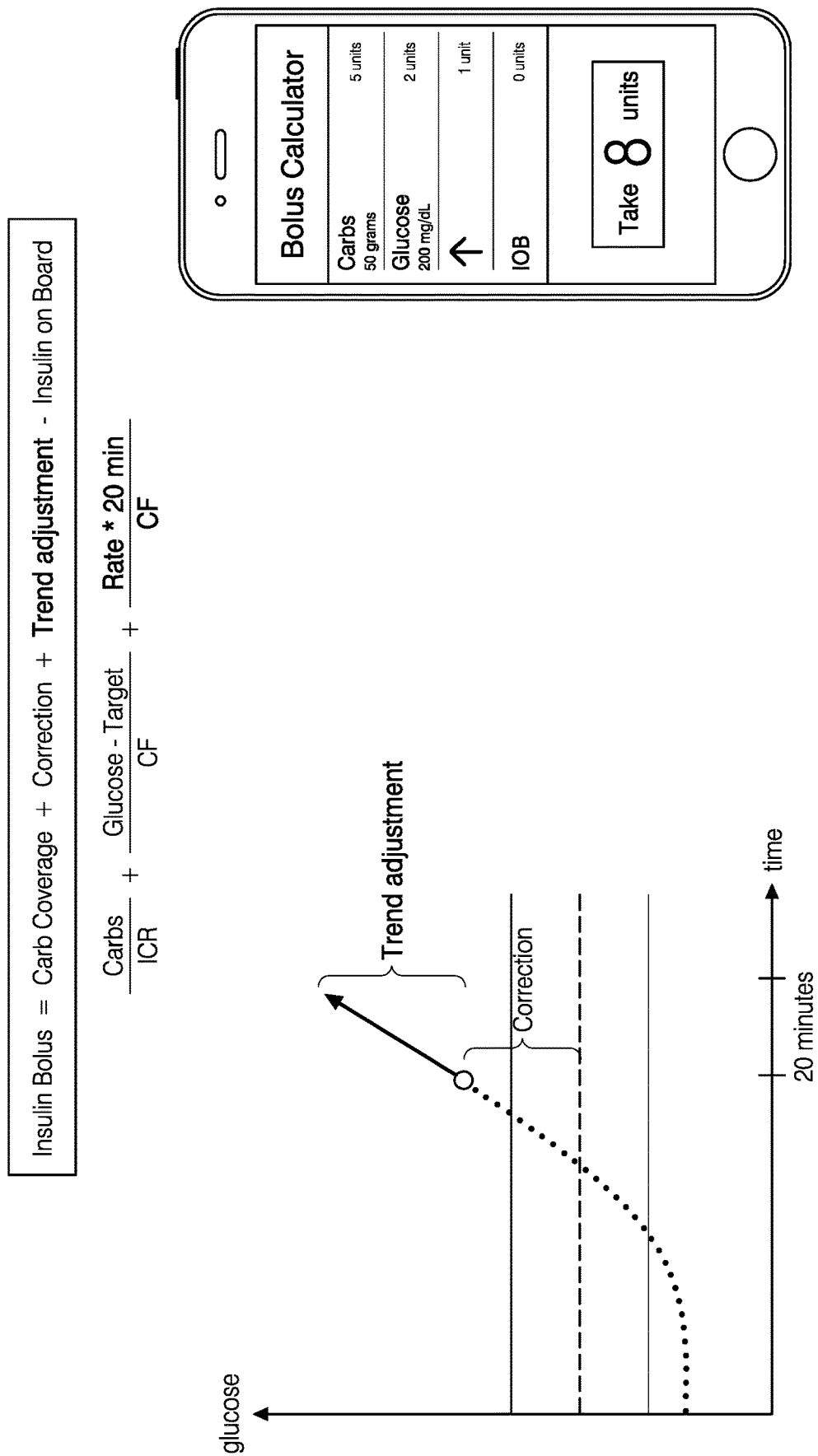
FIG. 11 illustrates aspects of correcting bolus calculator parameters using trend adjustments.

In more detail, an exemplary calculation employing a trend adjustment is indicated in FIG. 11. A trend adjustment is equal to a rate of glucose change times the time period in question, i.e., the time to achieve the target, e.g., 20 minutes, divided by the correction factor. In essence, the correction and trend adjustment is equivalent to predicting what the glucose level would be 20 minutes from now assuming the current rate of change remains constant, and correcting based on the future glucose level.

FIG. 11 further illustrates a graphical indication of an exemplary trend adjustment, i.e., where a trend is taken into account in a bolus calculation. Trend adjustments can be turned off in the bolus calculator settings, but can also be defaulted on. No trend adjustment will generally be made when trend data is unavailable from the CGM app.

The correction factor is a patient-specific value usually estimated with the help of the patient's physician. The correction factor can vary throughout the day, and may change over time. It represents the drop in glucose generated by taking one unit of insulin. So if the patient's blood glucose is 200 and taking one unit of insulin makes their blood glucose drop to 120, their resulting correction factor is 80.

The ICR, like the correction factor, is patient-specific, dependent on physiology, and can change throughout the day and over time. Most patients have three estimates: for breakfast, lunch, and dinner. What this parameter should reflect is the number of carbohydrates covered by 1 unit of insulin. So, if a patient has an ICR of 15, that means that eating 15 g of carbs and taking 1 unit of insulin would lead to their blood glucose eventually returning to its current value at the end of the insulin action time, e.g., approximately four hours.

In certain implementations of the bolus calculator functionality, during real-time use of the bolus calculator, the user may be shown their last insulin dose, which can be updated if it is incorrect.

For MDI users, bolus calculations involving IOB, which is the amount of a rapid acting insulin bolus still acting in a user's body several hours after taking it, can be calculated from insulin event entries made by such users. The bolus calculator can further take into account insulin action time (IAT), which is the total time insulin is still active in the user system after a bolus. IAT varies by person and situation. While for shorthand purposes linear IOB curves are easier for patients to understand, curvilinear IOB curves better approximate the pharmacokinetic actions of insulin. Recent studies have shown that even more accurate results may be obtained by using log normal distributions as insulin action profiles. IOB may follow a cumulative distribution function, and the remaining IOB at any point in time may be determined from the cumulative distribution function of the lognormal distribution, i.e., IOB=1−CDF. Lognormal distributions have generally very long tails and thus the IOB does not drop to zero at end of the insulin action time, but generally maintains a steady level, e.g., 19%. A user generally expects to have no insulin active in their system after the insulin action time has ended, and thus to adjust the IOB to fall smoothly to zero at the insulin action time, a linear adjustment may be subtracted at every point in time. The top equation in FIG. 11 shows such a subtraction of the JOB. In making trend adjustments, no adjustment will generally be made when the trend is flat, and adjustments may be limited such that a maximum trend adjustment is provided for, e.g., additional adjustments may not be made for more than 60 mg/dL predicted rise or fall (3 mg/dL/min rate).

Benefits of using trend adjustments are manifold. For example, for most users, there is an approximately two hour "blind spot" post meal where carbs and insulin are active in their system. During this time, it is generally considered best to cover additional carbohydrates, but not to apply corrections. Pump bolus calculators do this by not subtracting IOB from the carb portion, only the correction portion, but this has the effect of recommending too much insulin for meals out of the blind spot.

Thus, when a bolus is computed within the last two hours, i.e., in the post meal blind spot, carb coverage is computed, but not a correction bolus or trend adjustment. IOB is only subtracted from the carb coverage if the predicted glucose is below the target range, e.g., the current glucose value is 80 and the rate is −2 mg/dL/min.

Research has shown that, by inclusion of trend information in bolus calculators, increased time is achieved within target ranges, and less hypoglycemia is seen, as compared to the case of no adjustments for trend.

Transmission Details

Transmissions of bolus calculator settings and parameters may be made from HCPs through the cloud to CGM apps of a patient (and thus bolus calculator apps/functionality) through the use of real-time services that can be implemented, e.g., in the cloud. Such services may include real-time event reporting, which may be extended to include not only the reporting of events but also transmission (in the opposite direction) of bolus calculator settings and parameters. Some data paths may be used that are persistent, and others that are temporary.

In one variation, followers, e.g., parents, may be informed when the sharer, e.g., child, boluses, and may further be informed as to whether the child bolused the calculated amount or a different amount. Such may allow future discussion, potential bolus calculator modification, and/or the building of confidence in the bolus calculator performance. For example, upon the calculation of a bolus value, a message may be sent to one or more followers, e.g., via text message, app, or the like. Such may indicate to the follower that the patient may be bolusing or has already bolused where such data is available. Where the bolus calculation is performed on a medicament delivery device in communication with a monitoring device, e.g., a smart phone, the smart phone functionality may be leveraged to provide a message to one or more followers based on the action that occurred in the medicament delivery device. For example, if the medicament delivery device was employed to deliver a bolus of insulin to a user, a smart phone may be employed to send out messages to followers.

In more detailed implementations, bolus information may be transmitted to followers, and where available, the effect of the bolus may be transmitted as well. For example, bolus information may be transmitted at the time of delivery. In addition, several hours after the bolus was delivered, the bolus information may be repeated along with a chart indicating the patient's subsequent glucose values. In this way, the effect of the bolus may be seen and reviewed by the follower. In some cases, more summary information than a chart may be provided, e.g., an indication of a percentage of time in a target range.

In yet other implementations, if a follower reviews the transmitted data and desires to communicate a potential modification to bolus calculator parameters, functionality may be provided such that the follower can transmit the suggestion to the patient. Alternatively, the follower could transmit the notification of a potential bolus calculator modification to the HCP directly. Such functionality may be particularly useful in cases where one HCP is communicating suggestions to another HCP.

As another benefit, if a follower reviews the transmitted data and notices that the patient is spending considerably more time within a target range than previously, e.g., with use of other bolus calculator methodologies, then follower confidence in the bolus calculator will increase, leading to even further increased usage and subsequent health benefits.

Additional details of transmissions of messages for purposes of sharing and following may be found in U.S. Patent Publication Nos. 2014/0184422 and 2014/0187889, all of which are incorporated herein by reference in their entirety, describe systems and methods for remote monitoring of analyte measurements that can be implemented with embodiments disclosed herein.

Such systems and methods may also provide notification from HCP to HCP. In one example, an endocrinologist may be informed of what general practice physicians are prescribing as far as bolus calculator settings, and in the same way certified diabetic educators may be informed about the patients under their care. Other HCP's associated with the user may be similarly informed, and the data delivered may be specific and tailored, either in content, format or both, to that HCP.

Use of a server in HCP involvement in bolus calculator parameter setting provides certain benefits. For example, the server can provide messaging/emailing services to the HCP and back again to the patient. The messaging/emailing may be triggered by a bolus change, for example, as well as a potential modification.

As a particular example, notifications, e.g., alerts, could be set up to notify an HCP about a patient's glucose levels, particularly in response to insulin dosing based on use of the bolus calculator. Such alerts may include when the patient's glucose levels are outside of certain ranges, particularly if close to bolus events. Based on alerts, the HCP could check patient data via a Share-like system and modify/update the bolus calculator settings. Where the HCP modifies the bolus calculator settings, as noted above, the system can configure a file that will get sent through the cloud in an encrypted fashion to the mobile device running the bolus calculator app. Reports may be generated in response, such reports being appropriately formatted for the recipient, and sent to the recipient in a secure manner.

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g., smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e., transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

In this document, the terms "computer program medium" and "computer usable medium" and "computer readable medium", as well as variations thereof, are used to generally refer to transitory or non-transitory media such as, for example, main memory, storage unit interface, removable storage media, and/or channel. These and other various forms of computer program media or computer usable/readable media may be involved in carrying one or more sequences of one or more instructions to a processing device for execution. Such instructions embodied on the medium, may generally be referred to as "computer program code" or a "computer program product" or "instructions" (which may be grouped in the form of computer programs or other groupings). When executed, such instructions may enable the computing module or a processor thereof or connected thereto to perform features or functions of the present disclosure as discussed herein.

Various embodiments have been described with reference to specific example features thereof. It will, however, be evident that various modifications and changes may be made thereto without departing from the broader spirit and scope of the various embodiments as set forth in the appended claims. The specification and figures are, accordingly, to be regarded in an illustrative rather than a restrictive sense.

Although described above in terms of various example embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described example embodiments.

Terms and phrases used in the present application, and variations thereof, unless otherwise expressly stated, should be construed as open ended as opposed to limiting. As examples of the foregoing: the term "including" should be read as meaning "including, without limitation" or the like; the term "example" is used to provide illustrative instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed in multiple groupings or packages or across multiple locations.

Additionally, the various embodiments set forth herein are described in terms of example block diagrams, flow charts, and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for continuous analyte monitoring, configured for interoperability with one or more third party applications, comprising:
   a. running a continuous glucose monitoring (CGM) app on a first device, the CGM app in communications with a CGM sensor through sensor electronics, the sensor electronics coupled to the CGM sensor and transmitting real-time data to the first device, the real-time data comprising continuous glucose measurements from the CGM sensor;
   b. receiving data in the CGM app, the data comprising third party data processed or stored by another app comprising a third party application running independently from the CGM app, the data received through an API, the received data operable to generate, in real-time, a bolus calculation that indicates a bolus value, the received data operable to generate the bolus calculation when used in combination with the real-time data from the CGM sensor in the generating of the bolus calculation; and
   c. prior to using the received data, authenticating the received data based on the data being processed or stored independently from the CGM app by the other app comprising the third party application, and if the authentication is successful, using the received data in combination with the real-time data to generate the bolus calculation and provide the bolus calculation to a user for viewing, and if the authentication is not successful, then not using the received data to generate the bolus calculation, and wherein authenticating the received data comprises determining whether the other app is a trusted app.

2. The method of claim 1, wherein the first device is a smart phone or a dedicated continuous glucose monitor.

3. The method of claim 1, wherein the other app is running on a second device.

4. The method of claim 3, wherein the second device is a medicament delivery device including a pump or pen.

5. The method of claim 3, wherein the second device is a wearable fitness sensor.

6. The method of claim 3, wherein the second device is a medical device, and further comprising controlling the medical device at least in part with data from the bolus calculation.

7. The method of claim 6, wherein the medical device is a medicament delivery device, and further comprising controlling medicament delivery of the medicament delivery device at least in part with data from the bolus calculation.

8. The method of claim 1, wherein the authenticating includes comparing a certificate associated with the other app to a list of trusted certificates stored on the first device.

9. The method of claim 1, wherein the received data includes exercise data or meal data or population data from a database.

10. The method of claim 1, further comprising, and prior to using the received data, displaying the received data for confirmation by a user on a user interface of the first device, and upon successful confirmation, using the received data in the bolus calculation.

11. The method of claim 1, wherein the CGM app includes bolus calculator functionality, and wherein the other app is running on a medicament delivery device incorporating the bolus calculator functionality, and further comprising automatically disabling the bolus calculator functionality in the CGM app upon detecting that the other app incorporates the bolus calculator functionality.

12. The method of claim 1, wherein the authentication includes determining a first identification of a user associated with the CGM app, and determining a second identification of a user associated with the other app, and determining if the first and second identifications pertain to the same user.

13. A computing system, comprising:
a memory comprising executable instructions; and
a processor in data communication with the memory and configured to execute the instructions to cause the computing system to:
a. run a continuous glucose monitoring (CGM) app on a first device, the CGM app in communications with a CGM sensor through sensor electronics, the sensor electronics coupled to the CGM sensor and transmitting real-time data to the first device, the real-time data comprising continuous glucose measurements from the CGM sensor;
b. receive data in the CGM app, the data comprising third party data processed or stored by another app comprising a third party application running independently from the CGM app, the data received through an API, the received data operable to generate a bolus calculation that indicates a bolus value, the received data operable to generate the bolus calculation when used in combination with the real-time data from the CGM sensor in the generating of the bolus calculation; and
c. prior to using the received data, authenticate the received data based on the data being processed or stored independently from the CGM app by the other app comprising the third party application, and if the authentication is successful, use the received data in combination with the real-time data to generate the bolus calculation and provide the bolus calculation to a user for viewing, and if the authentication is not successful, then not using the received data to generate the bolus calculation, and wherein the computing system being caused by the processor to authenticate the received data comprises the computing system being caused by the processor to determine whether the other app.

14. The computing system of claim 13, wherein the first device is a smart phone or a dedicated continuous glucose monitor.

15. The computing system of claim 13, wherein the other app is running on a second device.

16. The computing system of claim 15, wherein the second device is a medicament delivery device including a pump or pen.

17. The computing system of claim 15, wherein the second device is a wearable fitness sensor.

18. The computing system of claim 15, wherein the second device is a medical device, and wherein the processor is further configured to cause the computing system to control the medical device at least in part with data from the bolus calculation.

19. The computing system of claim 18, wherein the medical device is a medicament delivery device, and wherein the processor is further configured to cause the computing system to control medicament delivery of the medicament delivery device at least in part with data from the bolus calculation.

20. The computing system of claim 13, wherein the authenticating includes determining if the other app is a trusted app by comparing a certificate associated with the other app to a list of trusted certificates stored on the first device.

21. The computing system of claim 13, wherein the received data includes exercise data or meal data or population data from a database.

22. The computing system of claim 13, wherein prior to using the received data, the processor is further configured to cause the computing system to display the received data for confirmation by a user on a user interface of the first device, and upon successful confirmation, use the received data in the bolus calculation.

23. The computing system of claim 13, wherein the CGM app includes bolus calculator functionality, wherein the other app is running on a medicament delivery device incorporating the bolus calculator functionality, and wherein the processor is further configured to cause the computing system to automatically disable the bolus calculator functionality in the CGM app upon detecting that the other app incorporates the bolus calculator functionality.

24. The computing system of claim 13, wherein the authenticating includes determining a first identification of a user associated with the CGM app, and determining a second identification of a user associated with the other app, and determining if the first and second identifications pertain to the same user.

25. The method of claim 1, wherein the authenticating includes comparing a timestamp on the received data to a timestamp on the real-time data, or comparing the timestamp on the received data to a time of receiving the received data according to a clock on the first device.

* * * * *